United States Patent
Metcalf, III et al.

(10) Patent No.: US 7,019,139 B2
(45) Date of Patent: *Mar. 28, 2006

(54) QUINOLINONES AND USES THEREOF

(75) Inventors: Chester A. Metcalf, III, Needham, MA (US); William C. Shakespeare, Southborough, MA (US); Tomi K. Sawyer, Southborough, MA (US); Yihan Wang, Newton, MA (US); Regine Bohacek, Boston, MA (US); Rajeswari Sundaramoorthi, Watertown, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/715,794

(22) Filed: Nov. 17, 2003

(65) Prior Publication Data

US 2004/0167101 A1    Aug. 26, 2004

Related U.S. Application Data

(63) Continuation of application No. 10/177,500, filed on Jun. 21, 2002, now Pat. No. 6,713,462.

(60) Provisional application No. 60/299,936, filed on Jun. 21, 2001.

(51) Int. Cl.
*C07D 221/18* (2006.01)
*C07D 215/16* (2006.01)

(52) U.S. Cl. .................. 546/23; 546/153; 546/155; 546/157; 546/158

(58) Field of Classification Search ............ 546/23, 546/153, 155, 157, 158
See application file for complete search history.

(56) References Cited

U.S. PATENT DOCUMENTS

| | | | |
|---|---|---|---|
| 6,002,008 A | 12/1999 | Wissner | |
| 6,037,350 A | 3/2000 | Venet et al. | 514/312 |
| 6,150,377 A | 11/2000 | Lyssikatos et al. | 514/312 |
| 6,169,096 B1 | 1/2001 | Venet et al. | 514/312 |
| 6,713,462 B1 * | 3/2004 | Metcalf et al. | 514/82 |

FOREIGN PATENT DOCUMENTS

| | | |
|---|---|---|
| WO | WO 97/21701 | 6/1997 |
| WO | WO 98/55124 | 12/1998 |
| WO | WO 99/20612 | 4/1999 |
| WO | WO 00/01386 | 1/2000 |
| WO | WO 00/01411 | 1/2000 |
| WO | WO 00/12498 | 3/2000 |
| WO | WO 00/12499 | 3/2000 |
| WO | WO 02/24682 | 3/2002 |
| WO | WO 02/24683 | 3/2002 |
| WO | WO 02/24686 | 3/2002 |
| WO | WO 02/24687 | 3/2002 |

OTHER PUBLICATIONS

Boschelli, D.H. Et al. Synthesis and Src Kinase Inhibitory Activity of a Series of 4-phenylamino-3-quinolinecarbonitriles. J. Med.Chem. Jan. 2001, vol. 44, pp. 822-833.

Database CA on STN, Chemical Abstracts, (Columbus, OH, USA), No. 134:100834, Wang, Y.D. "Inhibitors of Src tyrosine kinase: the preparation and structure-activity relationship of 4-anilino-3-cyanoquinolines and 4-anilinoquinazolines," abstract, Bioorganic & Medicinal Chemistry Letters, 2000, vol. 10, No. 21, pp. 2477-2480.

Database CA on STN, Chemical Abstracts, (Columbus, OH, USA), No. 129:302564, Wissner, A. "Preparation of substituted 3-cyanoquinolines as inhibitors of protein tyrosine kinase," abstract WO9843960, Oct. 1998, p. 223.

* cited by examiner

*Primary Examiner*—D. Margaret Seaman
(74) *Attorney, Agent, or Firm*—David L. Berstein

(57) ABSTRACT

The invention relates to compounds of the general formula (and pharmaceutically acceptable derivatives thereof):

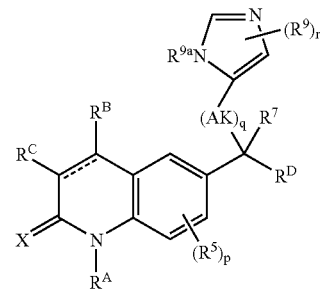

in which $R^A$, $R^B$, $R^C$, $R^D$, $R^5$, $R^7$, $R^9$, $R^{9a}$, AK, p, q, r and X are as defined herein, and to their preparation and use.

6 Claims, No Drawings

QUINOLINONES AND USES THEREOF

PRIORITY INFORMATION

The present application is a continuation of U.S. patent application Ser. No. 10/177,500, filed Jun. 21, 2002 now U.S. Pat. No. 6,713,462 and claims priority under 35 U.S.C. §119(e) to U.S. Provisional Patent Application No. 60/299,936, filed Jun. 21, 2001, the entire contents of each of these applications are hereby incorporated by reference.

BACKGROUND OF THE INVENTION

The need to treat elusive and debilitating disorders such as cancer, osteoporosis and other diseases involving untoward bone resorption (e.g., Paget's Disease, primary and secondary hyperparathyroidism, humoral hypercalcemia of malignancy, various cancers where resorption is increased, and rheumatoid arthritis), and disorders involving increased vascular permeability, to name a few, has led to extensive research on the mechanisms involved in disease initiation and/or progression and on the identification of new drugs which might interfere with those mechanisms.

One approach, for example, for treating bone disorders is inhibition of the osteoclast proton pump. See e.g., Blair et al., *Science* 1989, 245, 855–857; Finbow et al., *Biochem. J.* 1997, 324, 697–712; Forgac, M. *Soc. Gen. Physiol. Ser.* 1996, 51, 121–132; Baron et al., *J. Cell. Biol.* 1985, 101, 2210–2222; Farina et al., *Exp. Opin. Ther. Patents* 1999, 9, 157–168; and David, P. and Baron, R. "The Vacuolar $H^+$-ATPase: A Potential Target for Drug Development in Bone Diseases" *Exp. Opin. Invest. Drugs* 1995, 4, 725–740.

Another approach to drug discovery for treating bone-related (and other) diseases involves the control of cellular signal transduction. See, for example, Missbach et al., "A Novel Inhibitor of the Tyrosine Kinase Src Suppresses Phosphorylation of Its Major Cellular Substrates and Reduces Bone Resorption In Vitro and in Rodent Models In Vivo." *Bone* 1999, 24, 437–449; Connolly et al., *Bioorg. & Med. Chem. Lett.* 1997, 7, 2415–2420; Trump-Kallmeyer et al., *J. Med. Chem.* 1998, 41, 1752–1763; Klutchko et al., *J. Med. Chem.* 1998, 41, 3276–3292; Legraverend et al., *Bioorg. & Med. Chem.* 1999, 7, 1281–1293; Chang et al., *Chem. & Biol.* 1999, 6, 361–375; Lev et al. *Nature* 1995, 376, 737–784; Palmer et al., *J. Med. Chem.* 1997, 40, 1519–1529.

Some approaches for the treatment of bone disorders such as osteoporosis include, for example, estrogens, bisphosphonates, calcitonin, flavonoids, and selective estrogen receptor modulators. Other approaches include peptides from the parathyroid hormone family, strontium ranelate, and growth hormone and insulin-like growth response (see, for example, Reginster et al. "Promising New Agents in Osteoporosis," *Drugs R &D* 1999, 3, 195–201). Unfortunately, these therapeutic agents still have significant shortcomings.

The variety of different approaches represented by the therapeutic agents currently available or under study evidence the variety of biological factors influencing the competing processes of bone production and resorption. Although progress has been made towards developing therapeutic agents for osteoporosis and other bone disorders, there remains a need to develop new therapeutic agents which have an improved therapeutic index, which may be given to patients who cannot well tolerate or do not respond to existing therapies, and/or which may be used in conjunction with other therapies.

Protein kinases, specifically Src protein kinases, have been shown to play a crucial role in osteoclast function and thus in the resorption of bone and the progression of the osteoporosis. In addition, cellular signal transduction mediated by kinases like Src is believed to play a key role in other diseases, for example cancer and diseases involving increased vascular permeability. Though the exact mechanisms of signal transduction is still unclear, tyrosine kinases have been shown to be important contributing factors in cell proliferation, carcinogenesis and cell differentiation.

Several families of protein tyrosine kinases have been implicated in human cancer, including, but not limited to Src, Abl, Jak, Ack, Csk, Fak, Fes, Frk, Tec, and Syk, to name a few. For a detailed review of the role of oncogenic kinase signalling see, Blume-Jensen et al. *Nature,* 2001, 411, 355, and references cited therein.

Furthermore, certain kinases are believed to mediate signaling activity in response to a variety of growth factors, including VEGF, vascular endothelial growth factor, (see, Schlessinger, *J. Cell* 2000, 100, 293; Lowell et al. *Genes Dev.* 1996, 10, 1845), which is an angiogenic factor that promotes vascular permeability. The ability to control (and/or diminish) increased vascular permeability by suppression of a signalling pathway would be useful for the treatment of patients suffering from diseases and conditions related to increases in vascular permeability (e.g., edema, hemorrhage, cancer, vasular leaks, and the like). For a review of antiangiogenic agents (including those agents having antitumor activity), see Klohs et al., *Curr. Opin. Biotechnol.* 1999, 10, 544.

Although some progress has been made in the treatment of certain debilitating diseases and disorders mentioned herein, there remains a need to develop new therapeutic agents which have an improved therapeutic index, which may be given to patients who cannot well tolerate or do not respond to existing therapies, and/or which may be used in conjunction with other therapies. Thus, new, selective inhibitors of osteoclast activity and promoters of osteoblast activity as well as therapeutic agents that can regulate a variety of other signal transduction pathways would be desirable. Such compounds may then be used to inhibit or promote complex biological processes in order to treat and/or prevent diseases associated with signalling (e.g., osteoporosis, cancer and edema, to name a few).

DESCRIPTION OF THE INVENTION

As discussed in more detail herein, there remains a need for the development of novel therapeutics useful for the treatment of bone related disorders, cancer, and signalling disorders generally. There is also a particular need for the development of selective therapeutic agents (e.g. those that can selectively target bone, or that can selectively inhibit or promote cellular signaling pathways).

1. General Description of Compounds of the Invention:

In recognition of the need to develop more selective and potent therapeutic agents, the present invention provides a novel family of quinolinones that have a broad range of useful biological and pharmacological properties.

These include compounds having the general formula I (and pharmaceutically acceptable derivatives thereof):

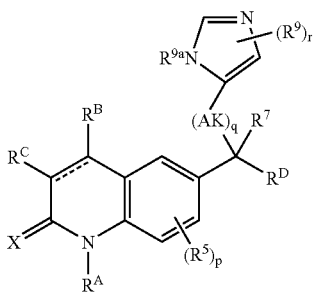

Formula I wherein the dotted line represents an optional bond;

X is O, S or $NR^H$;

$R^A$ is hydrogen, oxygen, or an aliphatic, heteroaliphatic, aryl or heteroaryl moiety;

$R^B$ is an aliphatic, heteroaliphatic, aryl or heteroaryl moiety;

$R^C$ is hydrogen; aliphatic; heteroaliphatic; aryl; heteroaryl; halogen; cyano; alkyloxycarbonyl; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO($NOR^L$)$R^M$, —CH=$NOR^J$, —$NR^LR^M$, —S(O)$_2R^L$, P(O)(OR$^L$)$R^M$, or an aliphatic, heteroaliphatic, aryl or heteroaryl moiety, and wherein each occurrence of $R^L$ and $R^M$ is independently hydrogen, or an aliphatic, heteroaliphatic, aryl or heteroaryl moiety;

$R^D$ is an aryl or heteroaryl moiety;

each occurrence of $R^9$ and $R^5$ is independently hydrogen; aliphatic; heteroaliphatic; aryl; heteroaryl; cyano; —C(O)$R^J$; —C(O)OR$^J$; —$NR^JC(O)OR^K$; —OC(O)$R^J$; —$NR^JSO_2R^K$; —$SO_2NR^JR^K$; —$NR^JC(O)R^K$; —C(O)$NR^JR^K$; —CH=$NOR^J$; —S(O)$_nR^J$, wherein n is an integer from 0 to 2; —(CR$^LCR^M$)$_u$—C_CR$^J$; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO($NOR^L$)$R^M$, —CH=$NOR^J$, —$NR^LR^M$, —S(O)$_2R^L$, —P(O)(OR$^L$)$R^M$, or an aliphatic, heteroaliphatic, aryl or heteroaryl moiety;

$R^7$ is hydrogen; aliphatic; heteroaliphatic; aryl; heteroaryl; cyano; —C(O)$R^J$; —C(O)OR$^J$; —$NR^JC(O)OR^K$; —OC(O)$R^J$; —$NR^JSO_2R^K$; —$SO_2NR^JR^K$; —$NR^JC(O)R^K$; —C(O)$NR^JR^K$; —CH=$NOR^J$; —S(O)$_nR^J$, wherein n is an integer from 0 to 2; —(CR$^LCR^M$)$_u$—C_CR$^J$; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO($NOR^L$)$R^M$, —CH=$NOR^J$, —$NR^LR^M$, —S(O)$_2R^L$, —P(O)(OR$^L$)$R^M$, or an aliphatic, heteroaliphatic, aryl or heteroaryl moiety;

u is an integer from 0–6;

AK is (CR$^PCR^Q$);

each occurrence of $R^P$ and $R^Q$ is independently hydrogen or an aliphatic moiety;

q is an integer from 0 to 5;

p is an integer from 0–3;

r is an integer from 0–2;

$R^{9a}$ is hydrogen; or an aliphatic or heteroaliphatic moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and at least one of $R^B$ or $R^D$ as defined above, comprises a phosphorus-containing moiety.

In certain embodiments, compounds described generally above have the limitation that:

(1) if q is 0; and $R^B$ comprises the only phosphorus-containing moiety PCM and PCM is —P(=O)OR'R", or if $R^{9a}$ is —C$_{1-6}$alkylP(=O)OR'OR"; wherein R' and R" are independently hydrogen, C$_{1-6}$alkyl, —(CR$_xR_y$)$_\omega$—C$_{3-10}$cycloalkyl or arylC$_{1-6}$alkyl; wherein w is an integer from 0–5 and R$_x$ and R$_y$ are independently hydrogen or C$_{1-6}$alkyl; then $R^B$ is not phenyl; and (2) if q is 0; and $R^B$ and $R^D$ are each phenyl, then neither $R^B$ nor $R^D$ is substituted with —P(=O)OR'R"; and $R^{9a}$ is not —C$_{1-6}$alkylP(=O)OR'OR"; wherein R' and R" are independently hydrogen, C$_{1-6}$alkyl, —(CR$_xR_y$)$_\omega$—C$_{3-10}$cycloalkyl or arylC$_{1-6}$alkyl; wherein w is an integer from 0–5 and R$_x$ and R$_y$ are independently hydrogen or C$_{1-6}$alkyl.

It will be appreciated that the compounds of the present invention are intended to encompass structures having a variety of phosphorus-containing moieties; however, in certain embodiments, one or more of $R^B$-$R^D$, as defined above or herein, are substituted with one or more phosphorus moieties each independently a group having a structure from Series I below:

Series I

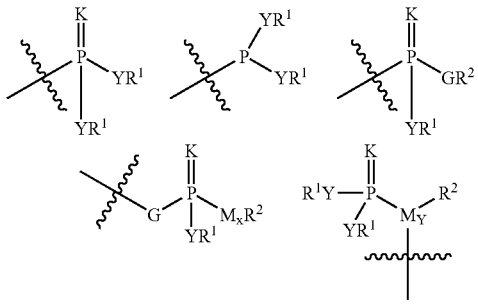

wherein each occurrence of K is independently O or S;

each occurrence of Y is independently —O—, —S—, —NH—, —NR$^1$—, or a chemical bond linking R$^1$ to P;

each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H;

each occurrence of R$^2$ is independently R$^1$, —PK(YR$^1$)(YR$^1$), —SO$_2$(YR$^1$) or —C(O)(YR$^1$);

each occurrence of G is independently absent, or is —O—, —S—, —NR$^1$— or (M)$_x$;

each occurrence of M is independently a substituted or unsubstituted methylene moiety, and any M-M' moiety may be electronically saturated or unsaturated;

each occurrence of x is independently an integer from 0–6; and each occurrence of M$_Y$ is independently a methine group or a lower alkyl moiety which contains a methine group and optionally may be further substituted;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

In certain embodiments, M is —$CR_xR_y$—, wherein each occurrence of $R_x$ and $R_y$ is independently hydrogen, halogen, alkyl, heteroalkyl, $OR^L$ or $NR^LR^M$; wherein each occurrence of $R^L$ and $R^M$ is independently hydrogen, or an alkyl, heteroalkyl, aryl or heteroaryl moiety. In certain exemplary embodiments, $R^1$ is hydrogen or lower alkyl and M is —$CH_2$—, —CH(OH)—, —$CH(NH_2)$—, —C(alkyl)(OH)—, —C(alkyl)($NH_2$)—, —CH(halo)- or —C(halo)$_2$-.

Exemplary phosphorus-containing moieties are further illustrated by the groups of Series Ia and Ib below:

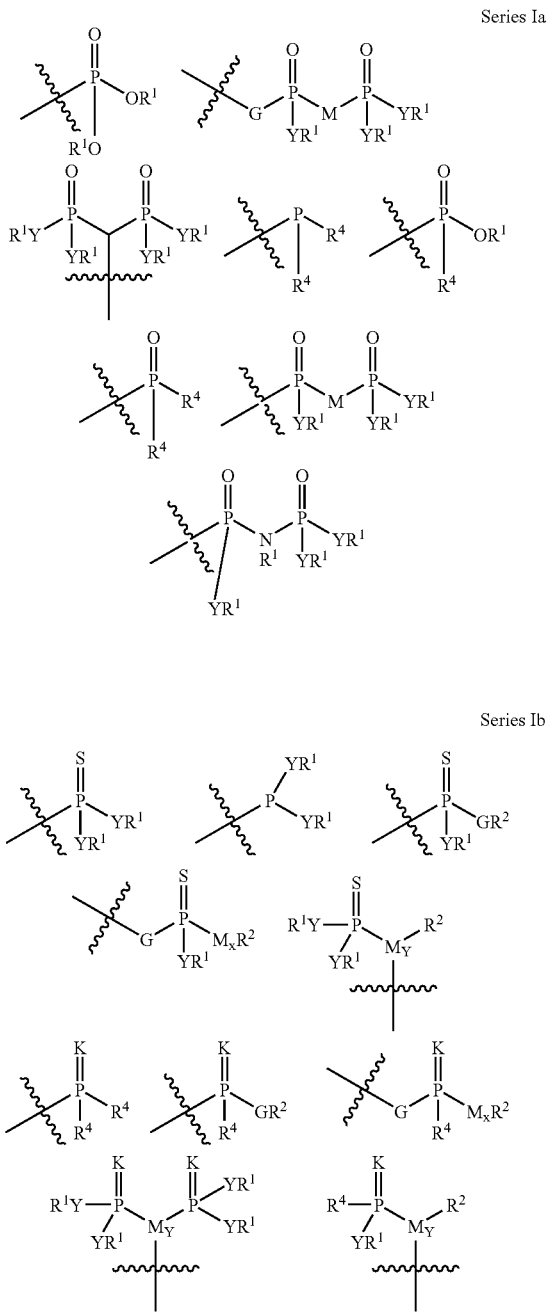

wherein each occurrence of K is independently O or S;

each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —$PK(YR^1)(YR^1)$, —$SO_2(YR^1)$ or —$(CO)(YR^1)$;

each occurrence of G is independently absent, or is —O—, —S—, —$NR^1$— or $(M)_x$;

each occurrence of M is independently a substituted or unsubstituted methylene moiety, and any M-M' moiety may be electronically saturated or unsaturated;

each occurrence of x is independently an integer from 0–6; and each occurrence of $M_Y$ is independently a methine group or a lower alkyl moiety which contains a methine group and optionally may be further substituted; and each occurrence of $R^4$ is independently an aliphatic, heteroaliphatic, aryl or heteroaryl moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

Exemplary phosphorus-containing moieties are further illustrated by Series Ic depicted below:

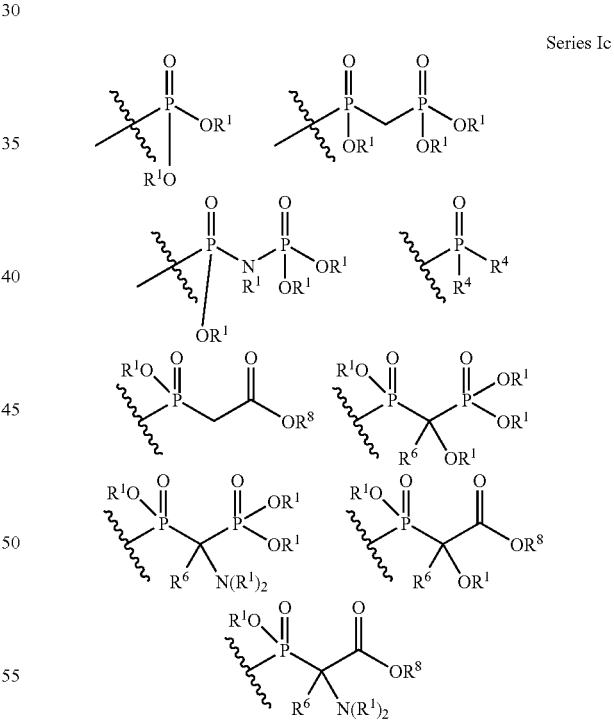

wherein each occurrence of $R^1$ is independently hydrogen, alkyl or aryl;

each occurrence of $R^4$ is independently alkyl or aryl;

each occurrence of $R^6$ is independently hydrogen, alkyl, heteroalkyl, aryl or heteroaryl; and each occurrence of $R^8$ is independently hydrogen, alkyl, heteroalkyl, aryl or heteroaryl, or a prodrug moiety;

wherein in each of the foregoing groups each alkyl or heteroalkyl moiety may be branched or unbranched, cyclic or acyclic and substituted or unsubstituted, and may contain one or more electronically unsaturated bonds, and each aryl and heteroaryl moiety may be substituted or unsubstituted.

Exemplary phosphorus-containing moieties are further illustrated by Series II depicted below:

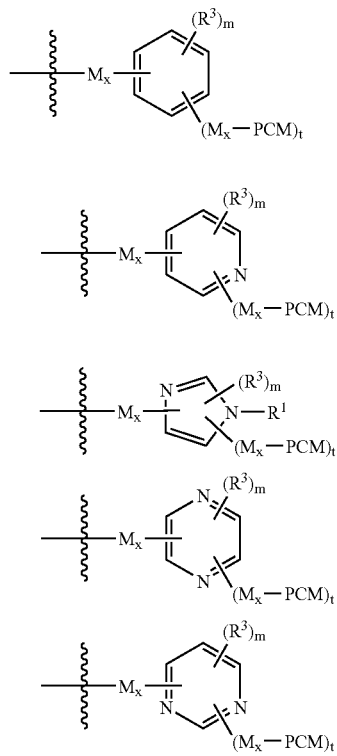

Series II wherein each occurrence of $R^3$ is independently hydrogen; halogen; —CN; $NO_2$; $N_3$; $R^1$; —$GR^1$; —CO(Y'$R^1$); —$NR^1$(Y'$R^1$); $S(O)_2$(Y'$R^1$); wherein each occurrence of Y' is independently —O—, —S—, —$NR^1$—, —C(O)—, —COO— or $S(O)_2$; and each occurrence of G is independently absent, or is —O—, —S—, —$NR^1$—, $S(O)_2$, or $(M)_x$;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

PCM is a phosphorus-containing moiety of Series I, Series Ia, Series Ib; or Series Ic, and m is an integer from 0–3, t is an integer from 1–3, and the sum of m+t is an integer from 1–5;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

Exemplary phosphorus-containing moieties are further illustrated by Series IIa below:

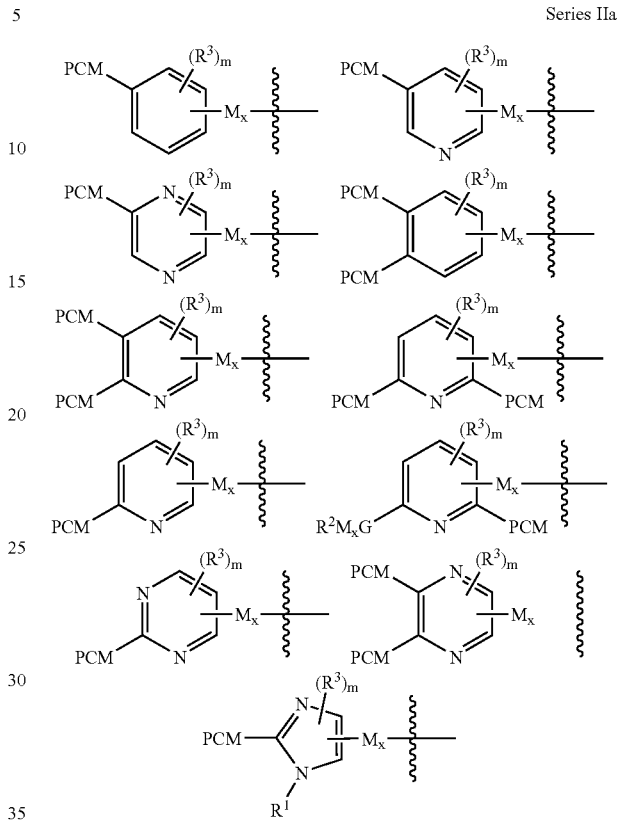

Series IIa wherein each occurrence of $R^3$ is independently hydrogen; halogen; —CN; $NO_2$; $N_3$; $R^1$; —$GR^1$; —CO(Y'$R^1$); —$NR^1$(Y'$R^1$); $S(O)_2$(Y'$R^1$); wherein each occurrence of Y' is independently —O—, —S—, —$NR^1$—, —C(O)—, —COO— or $S(O)_2$;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —PK($YR^1$)($YR^1$), —$SO_2$($YR^1$) or —C(O)($YR^1$); wherein each occurrence of Y is independently —O—, —S—, —NH—, —$NR^1$—, or a chemical bond linking $R^1$ to P;

each occurrence of G is independently absent, or is —O—, —S—, —$NR^1$, $S(O)_2$, or $(M)_x$;

each occurrence of M is independently a substituted or unsubstituted methylene moiety, and any M-M' moiety may be electronically saturated or unsaturated;

each occurrence of x is independently an integer from 0–6;

m is an integer from 0–3; and

PCM is a phosphorus-containing moiety of Series I, Series Ia, Series Ib or Series Ic;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

Exemplary phosphorus-containing moieties are further illustrated by Series IIb below:

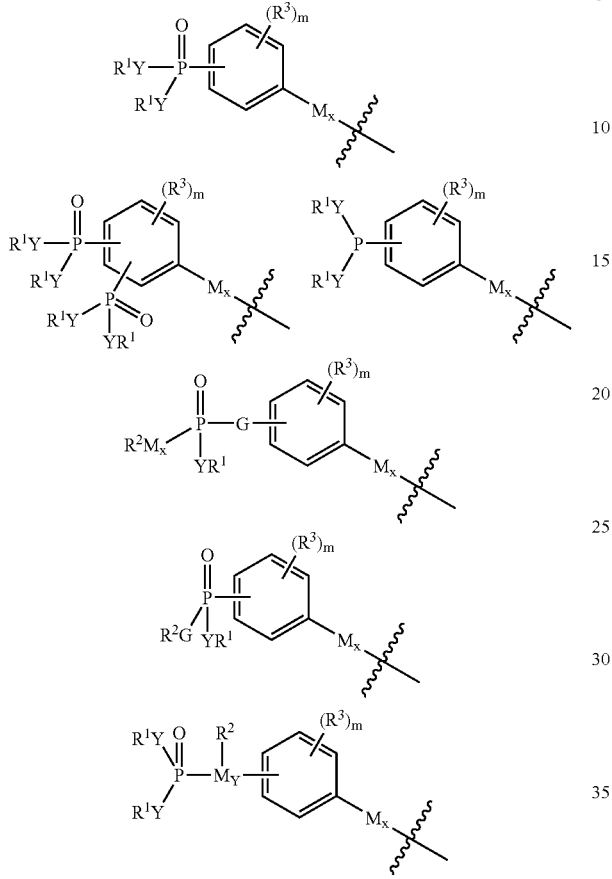

Series IIb wherein each occurrence of $R^3$ is independently hydrogen; halogen; —CN; $NO_2$; $N_3$; $R^1$; —$GR^1$; —CO(Y'R$^1$); —NR$^1$(Y'R$^1$); S(O)$_2$(Y'R$^1$); wherein each occurrence of Y' is independently —O—, —S—, —NR$^1$—, —C(O)—, —COO— or S(O)$_2$;

each occurrence of $R^2$ is independently $R^1$, —PK(YR$^1$)(YR$^1$), —SO$_2$(YR$^1$) or —C(O)(YR$^1$);

each occurrence of Y is independently —O—, —S—, —NH—, —NR$^1$—, or a chemical bond linking $R^1$ to P;

each occurrence of $R^1$ is independently a substituted or unsubstituted aliphatic, heteroaliphatic, aryl or heteroaryl moiety, or, except in YR$^1$ moieties in which Y is a covalent bond, $R^1$ may also be H;

each occurrence of G is independently absent, or is —O—, —S—, —NR$^1$—, S(O)$_2$, or (M)$_x$;

each occurrence of $M_Y$ is independently a methine group or a lower alkyl moiety which contains a methine group and optionally may be further substituted;

each occurrence of M is independently a substituted or unsubstituted methylene moiety, and any M-M' moiety may be electronically saturated or unsaturated;

each occurrence of x is independently an integer from 0–6; and m is an integer from 0–3;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

Exemplary phosphorus-containing moieties are further illustrated by Series III below:

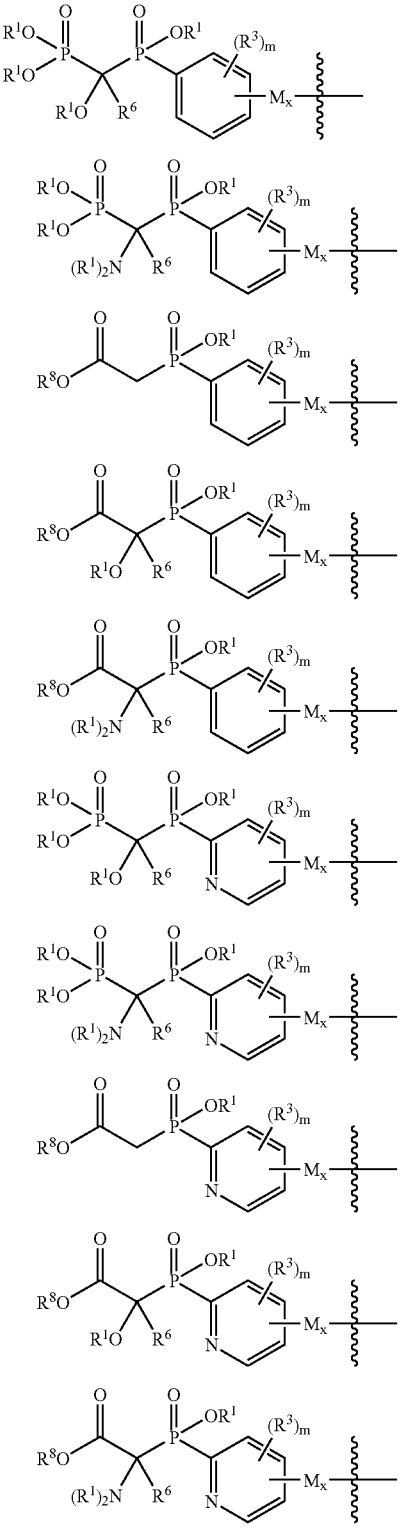

Series III

-continued

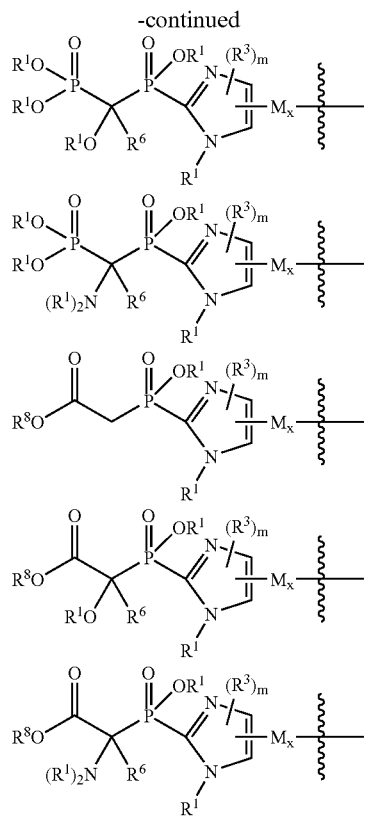

wherein each occurrence of R³ is independently hydrogen; halogen; —CN; NO₂; N₃; R¹; —GR¹; —CO(Y'R¹); —NR¹(Y'R¹); S(O)₂(Y'R¹); wherein each occurrence of Y' is independently —O—, —S—, —NR¹—, —C(O)—, —COO— or S(O)₂; each occurrence of G is independently absent, or is —O—, —S—, —NR¹—, S(O)₂, or (M)ₓ; and m is an integer from 0–4;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of M is independently a substituted or unsubstituted methylene moiety, and any M-M' moiety may be electronically saturated or unsaturated;

each occurrence of x is independently an integer from 0–6;

each occurrence of R⁶ is independently hydrogen, aliphatic, heteroaliphatic, aryl or heteroaryl moiety; and each occurrence of R⁸ is independently hydrogen, an aliphatic, heteroaliphatic, aryl or heteroaryl moiety, or a prodrug moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

Certain exemplary embodiments are described in more detail below and in the examples; however, it will be appreciated that the compounds of the invention are not limited by these examples.

2. Certain Featured Classes of Compounds of the Invention:

As discussed above, any one or more of $R^A$-$R^B$ or $R^D$, as defined herein, comprise or are substituted with one or more phosphorus-containing moieties.

It will be appreciated that in certain embodiments, $R^A$ is hydrogen or lower alkyl and $R^B$, independently for each occurrence is an aliphatic, heteroaliphatic, aryl or heteroaryl moiety and comprises or is substituted with at least one of the phosphorus-containing moieties in Series I depicted below:

Series I

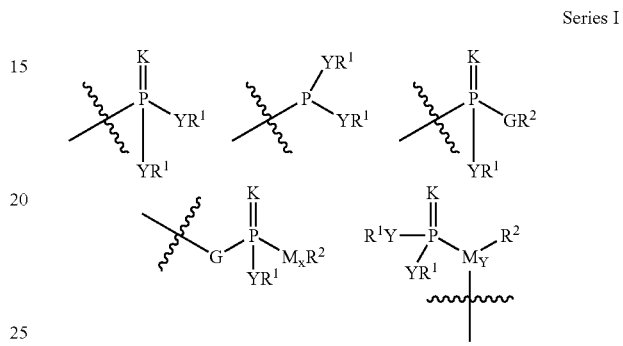

wherein each occurrence of K is independently O or S;

each occurrence of Y is independently —O—, —S—, —NH—, —NR1—, or a chemical bond linking R1 to P;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of R² is independently R¹, —PK(YR¹)(YR¹), —SO₂(YR¹) or —C(O)(YR¹);

each occurrence of G is independently absent, or is —O—, —S—, —NR¹— or (M)ₓ;

each occurrence of M is independently a substituted or unsubstituted methylene moiety, and any M-M' moiety may be electronically saturated or unsaturated;

each occurrence of x is independently an integer from 0–6; and each occurrence of $M_Y$ is independently a methine group or a lower alkyl moiety which contains a methine group and optionally may be further substituted.

In certain embodiments, compounds described generally above have the limitation that:

(1) if q is 0; and $R^B$ comprises the only phosphorus-containing moiety PCM and PCM is —P(=O)OR'R", or if $R^{9a}$ is —C₁₋₆alkylP(=O)OR'OR"; wherein R' and R" are independently hydrogen, C₁₋₆alkyl, —(CRₓRᵧ)ω—C₃₋₁₀cycloalkyl or arylC₁₋₆alkyl; wherein w is an integer from 0–5 and Rₓ and Rᵧ are independently hydrogen or C₁₋₆alkyl; then $R^B$ is not phenyl; and (2) if q is 0; and $R^B$ and $R^D$ are each phenyl, then neither $R^B$ nor $R^D$ is substituted with —P(=O)OR'R"; and $R^{9a}$ is not —C₁₋₆alkylP(=O)OR'OR"; wherein R' and R" are independently hydrogen, C₁₋₆alkyl, —(CRₓRᵧ)ω—C₃₋₁₀cycloalkyl or arylC₁₋₆alkyl; wherein w is an integer from 0–5 and Rₓ and Rᵧ are independently hydrogen or C₁₋₆alkyl.

It will be appreciated that in certain other embodiments, $R^A$ is hydrogen or lower alkyl and $R^D$ is aryl or heteroaryl moiety and comprises or is substituted with at least one of the phosphorus-containing moieties in Series I depicted below:

Series I

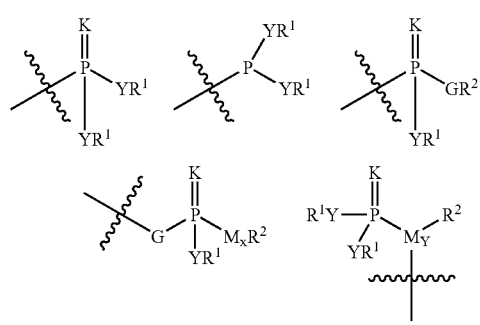

wherein each occurrence of K is independently O or S;

each occurrence of Y is independently —O—, —S—, —NH—, —NR$^1$—, or a chemical bond linking R$^1$ to P;

each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H;

each occurrence of R$^2$ is independently R$^1$, —PK(YR$^1$)(YR$^1$), —SO$_2$(YR$^1$) or —C(O)(YR$^1$);

each occurrence of G is independently absent, or is —O—, —S—, —NR$^1$— or (M)$_x$;

each occurrence of M is independently a substituted or unsubstituted methylene moiety, and any M-M' moiety may be electronically saturated or unsaturated;

each occurrence of x is independently an integer from 0–6; and each occurrence of M$_Y$ is independently a methine group or a lower alkyl moiety which contains a methine group and optionally may be further substituted.

In certain other embodiments, compounds as described generically above and as described in certain subsets herein, R$^A$ is hydrogen or lower alkyl and either or both of R$^B$ and R$^D$ comprises or is substituted with one or more of the following phosphorus-containing moieties of Series Ia or Ib depicted below:

Series Ia

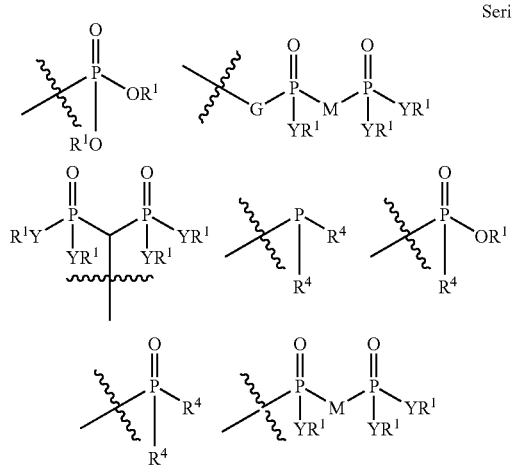

Series Ib

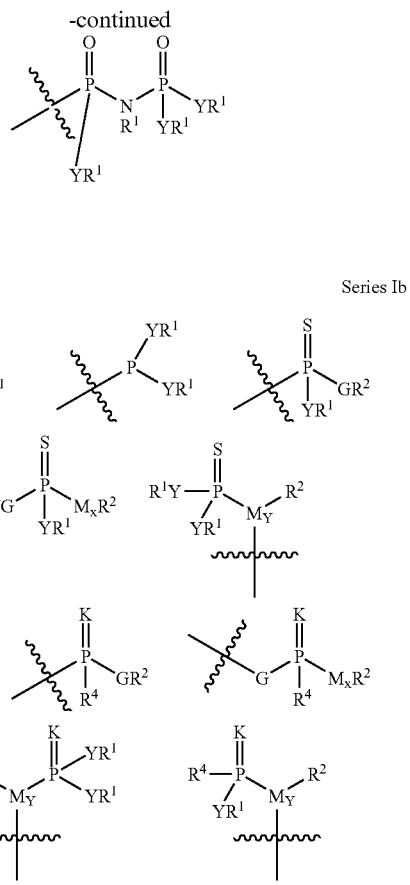

wherein each occurrence of K is independently O or S;

each occurrence of Y is independently —O—, —S—, —NH—, —NR$^1$—, or a chemical bond linking R$^1$ to P;

each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H;

each occurrence of R$^2$ is independently R$^1$, —PK(YR$^1$)(YR$^1$), —SO$_2$(YR$^1$) or C(O)(YR$^1$);

each occurrence of G is independently absent, or is —O—, —S—, —NR$^1$— or (M)$_x$;

each occurrence of M is independently a substituted or unsubstituted methylene moiety, and any M-M' moiety may be electronically saturated or unsaturated;

each occurrence of x is independently an integer from 0–6;

each occurrence of M$_Y$ is independently a methine group or a lower alkyl moiety which contains a methine group and optionally may be further substituted; and each occurrence of R$^4$ is independently an aliphatic, heteroaliphatic, aryl or heteroaryl moiety. In certain embodiments, M is —CR$_x$R$_y$, wherein each occurrence of R$_x$ and R$_y$ is independently hydrogen, halogen, alkyl, heteroalkyl, OR$^L$ or NR$^L$R$^M$; wherein each occurrence of R$^L$ and R$^M$ is independently hydrogen, or an alkyl, heteroalkyl, aryl or heteroaryl moiety. In certain exemplary embodiments, M is —CH$_2$—, —CH(OH)—, —CH(NH$_2$)—, —C(alkyl)(OH)—, —C(alkyl)(NH$_2$)—, —CH(halo)— or —C(halo)$_2$—.

In still other embodiments, R$^A$ is hydrogen or lower alkyl and either or both of R$^B$ and R$^D$, as described directly above, comprises or is substituted with at least one of the phosphorus-containing moieties in Series Ic depicted below:

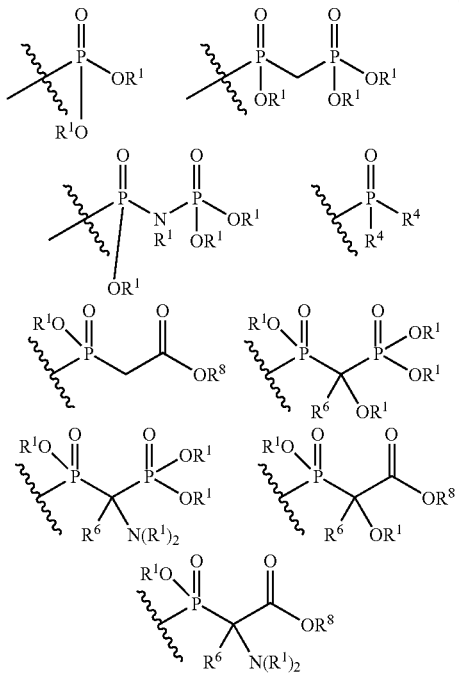

Series Ic wherein each occurrence of $R^1$ is independently hydrogen, alkyl or aryl;

each occurrence of $R^4$ is independently alkyl or aryl;

each occurrence of $R^6$ is independently hydrogen, alkyl, heteroalkyl, aryl or heteroaryl; and each occurrence of $R^8$ is independently hydrogen, alkyl, heteroalkyl, aryl or heteroaryl, or a prodrug moiety.

In certain embodiments, $R^6$ is hydrogen, lower alkyl, $OR^L$ or $NR^L R^M$; wherein each occurrence of $R^L$ and $R^M$ is independently hydrogen, or an alkyl, heteroalkyl, aryl or heteroaryl moiety. In certain other embodiments, $R^6$ is hydrogen, methyl, ethyl, OH or $NH_2$. In certain embodiments, $R^8$ is hydrogen, lower alkyl, lower heteroalkyl, aryl, heteroaryl or a prodrug moiety. In still other embodiments, $R^8$ is hydrogen, methyl, ethyl, or a prodrug moiety.

It will be appreciated that, in certain embodiments, $R^A$ is hydrogen or lower alkyl and either or both of $R^B$ or $R^D$ comprises or is substituted with any one of the phosphorus-containing aryl of heteroaryl moieties of Series II:

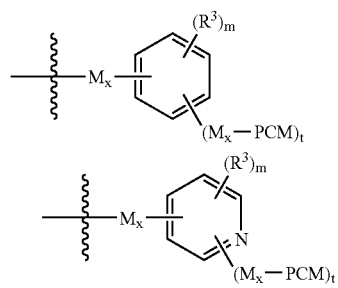

Series II

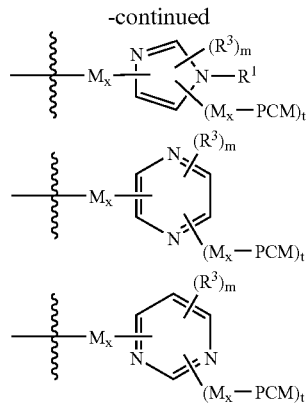

wherein each occurrence of $R^3$ is independently hydrogen; halogen; —CN; $NO_2$; $N_3$; $R^1$; —$GR^1$; —CO(Y'R$^1$); —NR$^1$(Y'R$^1$); S(O)$_2$(Y'R$^1$); wherein each occurrence of Y' is independently —O—, —S—, —NR$^1$—, —C(O)—, —COO— or S(O)$_2$; and each occurrence of G is independently absent, or is —O—, —S—, —NR$^1$—, S(O)$_2$, or (M)$_x$;

each occurrence of $R^1$ is independently a substituted or unsubstituted aliphatic, heteroaliphatic, aryl or heteroaryl moiety, or, except in YR$^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

PCM is a phosphorus-containing moiety of Series I, Series Ia, Series Ib; or Series Ic, and m is an integer from 0–3, t is an integer from 1–3, and the sum of m+t is an integer from 1–5.

In still other embodiments $R^A$ is hydrogen or lower alkyl and either or both of $R^B$ and $R^D$, as described directly above, comprises or is substituted with a phosphorus-containing moiety of Series IIa depicted below:

Series IIa

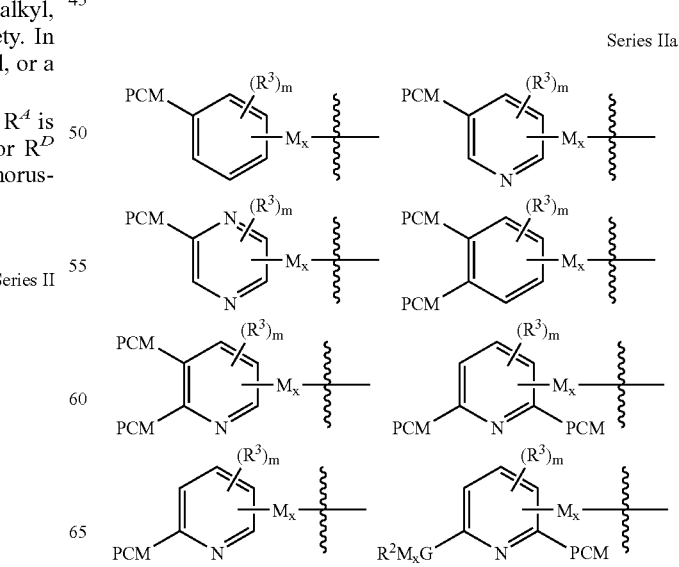

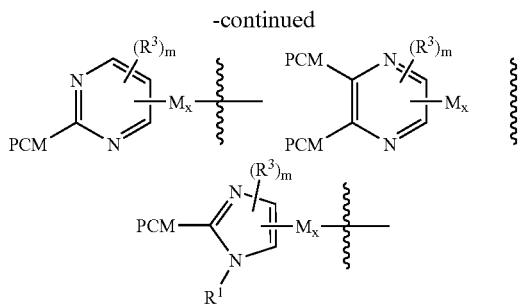

wherein each occurrence of $R^3$ is independently hydrogen; halogen; —CN; $NO_2$; $N_3$; $R^1$; —$GR^1$; —CO(Y'$R^1$); —$NR^1$(Y'$R^1$); $S(O)_2$(Y'$R^1$); wherein each occurrence of Y' is independently —O—, —S—, —$NR^1$—, —C(O)—, —COO— or $S(O)_2$;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —PK($YR^1$)($YR^1$), —$SO_2$($YR^1$) or —C(O)($YR^1$); wherein each occurrence of Y is independently —O—, —S—, —NH—, —$NR^1$—, or a chemical bond linking $R^1$ to P;

each occurrence of G is independently absent, or is —O—, —S—, —$NR^1$—, $S(O)_2$, or $(M)_x$;

each occurrence of M is independently a substituted or unsubstituted methylene moiety, and any M-M' moiety may be electronically saturated or unsaturated;

each occurrence of x is independently an integer from 0–6;

m is an integer from 0–3; and

PCM is a phosphorus-containing moiety of Series I, Series Ia, Series Ib or Series Ic.

In still other embodiments $R^A$ is hydrogen or lower alkyl and either or both of $R^B$ and $R^D$, as described directly above, comprises or is substituted with a phosphorus-containing moiety of Series IIb depicted below:

Series IIb

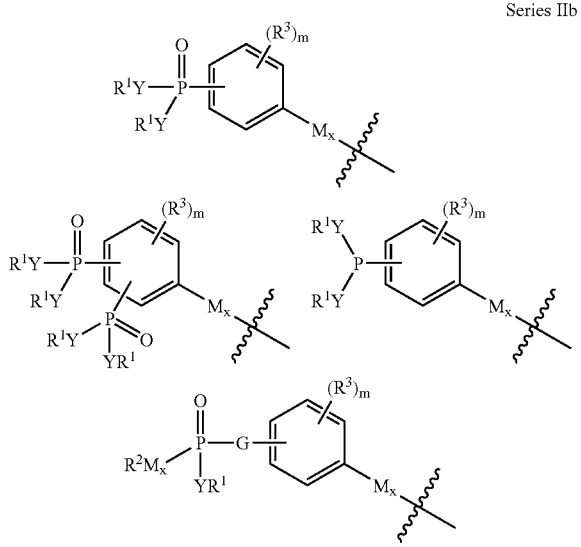

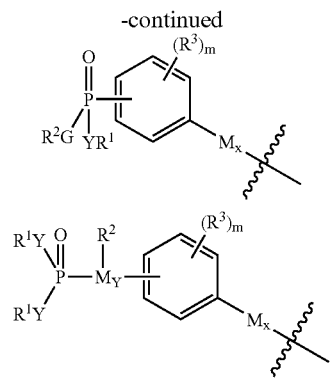

wherein each occurrence of $R^3$ is independently hydrogen; halogen; —CN; $NO_2$; $N_3$; $R^1$; —$GR^1$; —CO(Y'$R^1$); —$NR^1$(Y'$R^1$); $S(O)_2$(Y'$R^1$); wherein each occurrence of Y' is independently —O—, —S—, —$NR^1$—, —C(O)—, —COO— or $S(O)_2$;

each occurrence of $R^2$ is independently $R^1$, —PK($YR^1$)($YR^1$), —$SO_2$($YR^1$) or —C(O)($YR^1$);

each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of G is independently absent, or is —O—, —S—, —$NR^1$—, $S(O)_2$, or $(M)_x$;

each occurrence of $M_Y$ is independently a methine group or a lower alkyl moiety which contains a methine group and optionally may be further substituted;

each occurrence of M is independently a substituted or unsubstituted methylene moiety, and any M-M' moiety may be electronically saturated or unsaturated;

each occurrence of x is independently an integer from 0–6; and m is an integer from 0–3.

In still other embodiments $R^A$ is hydrogen or lower alkyl and either or both of $R^B$ and $R^D$, as described directly above, comprises or is substituted with a phosphorus-containing moiety of Series III depicted below:

Series III

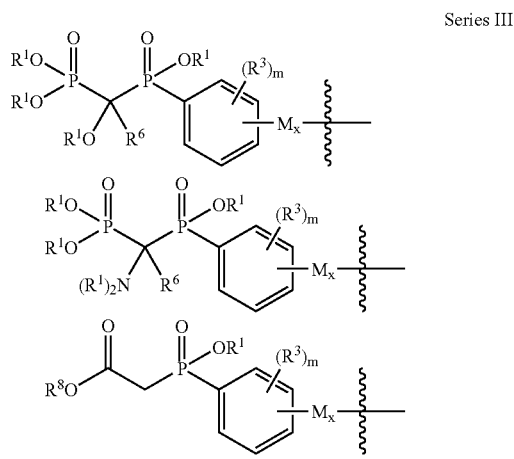

-continued

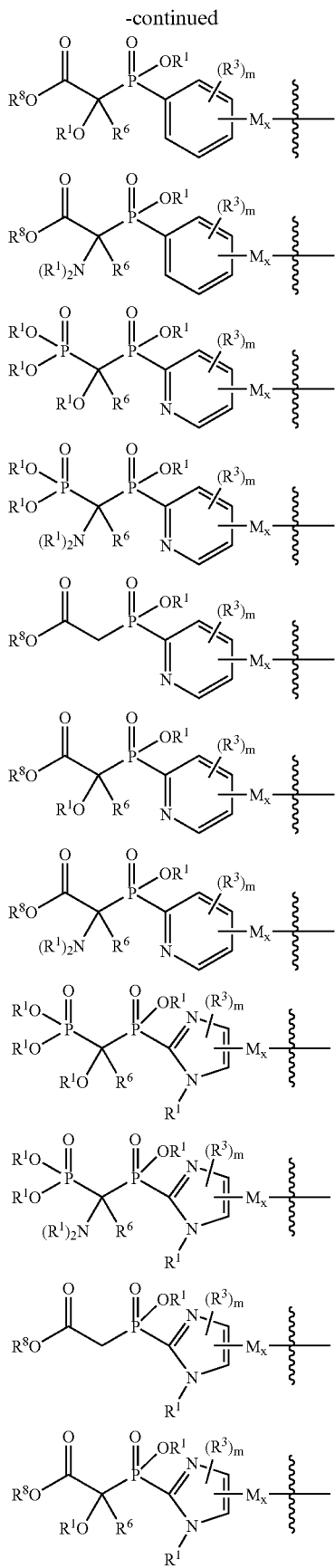

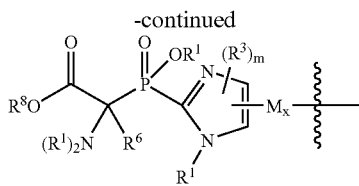

wherein each occurrence of $R^3$ is independently hydrogen; halogen; —CN; $NO_2$; $N_3$; $R^1$; —$GR^1$; —CO(Y'$R^1$); —$NR^1$(Y'$R^1$); S(O)$_2$(Y'$R^1$); wherein each occurrence of Y' is independently —O—, —S—, —$NR^1$—, —C(O)—, —COO— or S(O)$_2$; each occurrence of G is independently absent, or is —O—, —S—, —$NR^1$—, S(O)$_2$, or (M)$_x$; and m is an integer from 0–4;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

each occurrence of $R^6$ is independently hydrogen, aliphatic, heteroaliphatic, aryl or heteroaryl moiety; and each occurrence of $R^8$ is independently hydrogen, an aliphatic, heteroaliphatic, aryl or heteroaryl moiety, or a prodrug moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

It will be appreciated that, for each of the classes of compounds described above, in certain embodiments, if q is 0; and $R^B$ comprises the only phosphorus-containing moiety PCM and PCM is —P(=O)OR'R", or if $R^{9a}$ is —$C_{1-6}$alkylP(=O)OR'OR"; wherein R' and R" are independently hydrogen, $C_{1-6}$alkyl, —(CR$_x$R$_y$)$_\omega$—$C_{3-10}$cycloalkyl or aryl$C_{1-6}$alkyl; wherein w is an integer from 0–5 and $R^X$ and $R_y$ are independently hydrogen or $C_{1-6}$alkyl; then $R^B$ is not phenyl; and It will also be appreciated that for each of the classes of compounds described above, in certain exemplary embodiments, if q is 0; and $R^B$ and $R^D$ are each phenyl, then neither $R^B$ nor $R^D$ is substituted with —P(=O)OR'R"; and $R^{9a}$ is not —$C_{1-6}$alkylP(=O)OR'OR"; wherein R' and R" are independently hydrogen, $C_{1-6}$alkyl, —(CR$_x$R$_y$)$_\omega$—$C_{3-10}$cycloalkyl or aryl$C_{1-6}$alkyl; wherein w is an integer from 0–5 and $R^x$ and $R_y$ are independently hydrogen or $C_{1-6}$alkyl.

In certain embodiments, for each of the compounds as described above and herein, Y is a chemical bond linking the phosphorus atom to $R^1$. In certain other embodiments Y is an oxygen atom. In still other embodiments, Y is a chemical bond linking the phosphorus atom to $R^1$ and $R^1$ is a lower alkyl group having 1–6 carbon atoms. In yet other subsets of the compounds as generally described above, $R^A$ is hydrogen or an aliphatic or heteroaliphatic moiety and $R^D$ is hydrogen. In still other subsets X is oxygen. In yet other embodiments, $R^E$ is hydrogen.

In certain embodiments, for each of the compounds as described above and herein, Y is a chemical bond linking the phosphorus atom to $R^1$. In certain other embodiments Y is an oxygen atom. In still other embodiments, Y is a chemical bond linking the phosphorus atom to $R^1$ and $R^1$ is an alkyl group having 1–6 carbon atoms. In yet other subsets of the compounds as generally described above, $R^4$ is hydrogen or a lower alkyl moiety. In still other subsets X is oxygen. In yet other embodiments, $R^E$ is hydrogen. In still other embodiments K is oxygen.

The following structures illustrate several exemplary types of compounds of the classes and subclasses as described above and herein. Other types will be readily apparent to the reader.

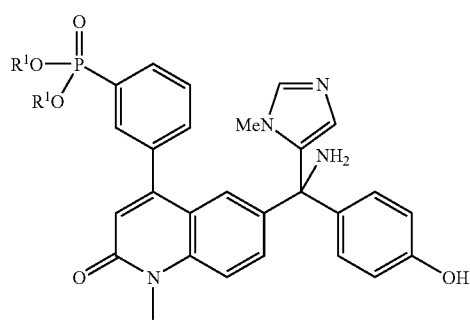

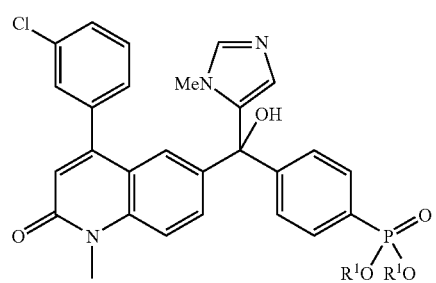

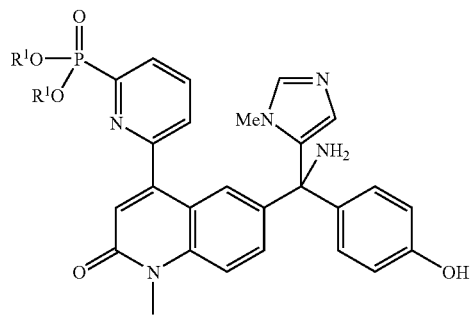

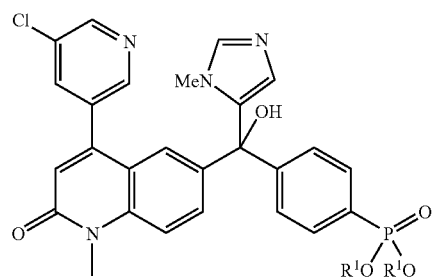

-continued

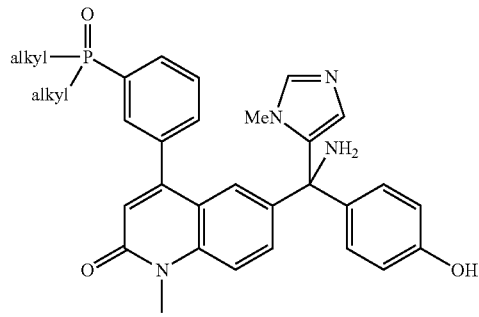

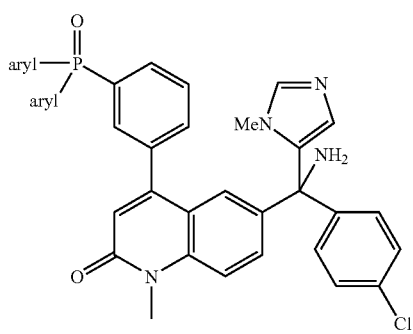

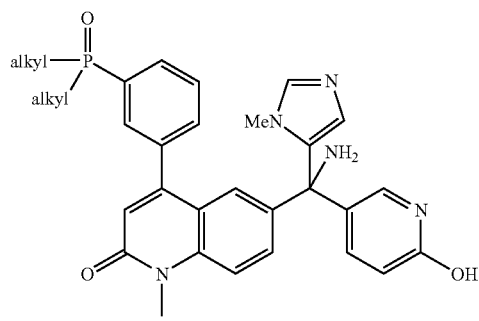

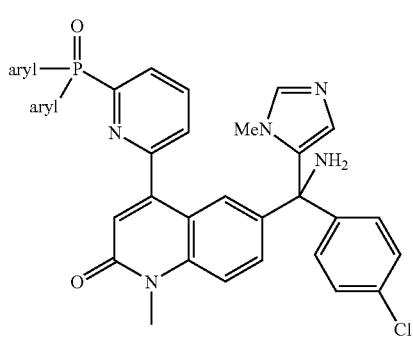

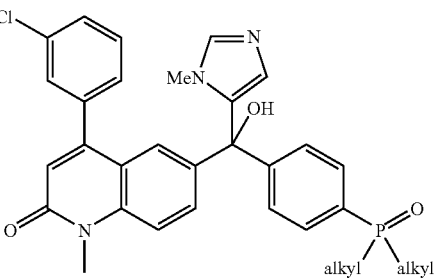

-continued

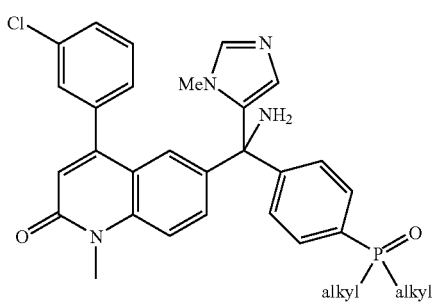

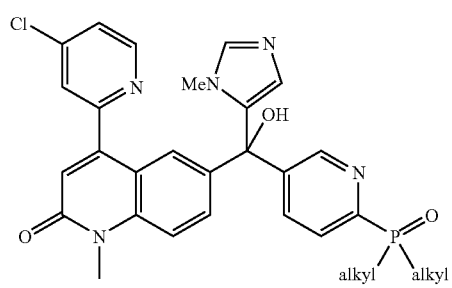

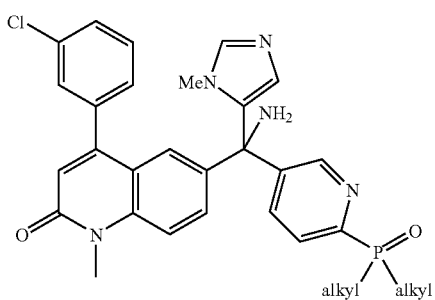

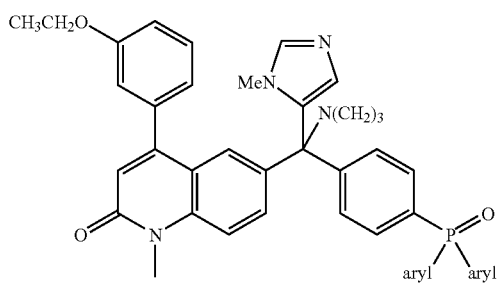

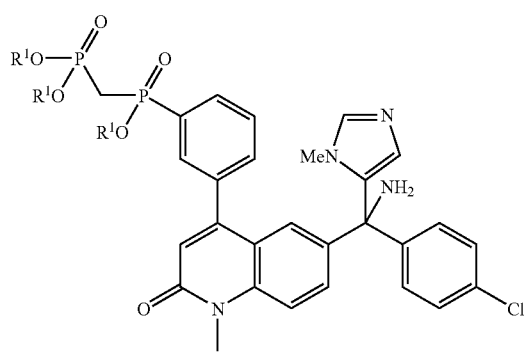

-continued

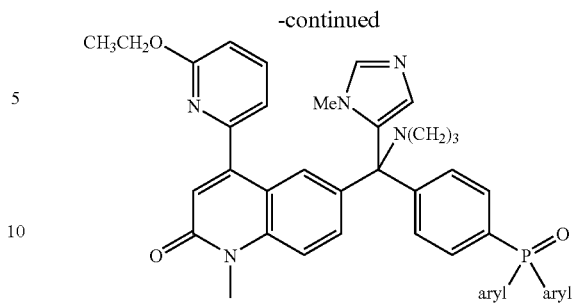

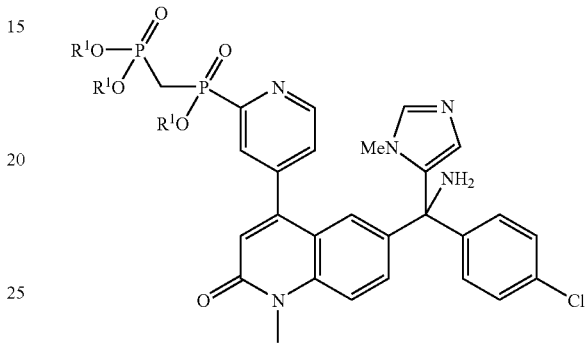

In addition to the classes of compounds described above, a class of compounds of special interest consists of compounds having the structure of Formula Ia (and pharmaceutically acceptable derivatives thereof):

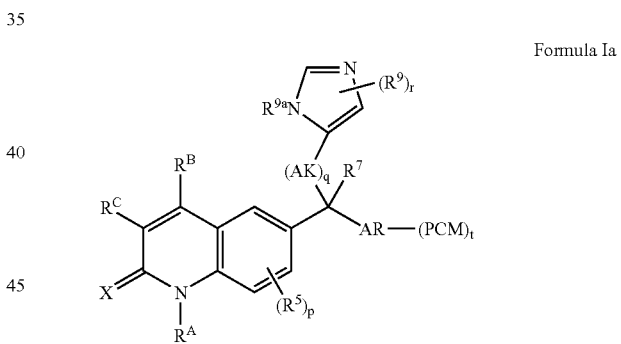

Formula Ia wherein AR is an aryl or heteroaryl moiety;
X is oxygen or sulfur;
$R^A$ is hydrogen, aliphatic, heteroaliphatic, aryl or heteroaryl moiety;
$R^B$ is an aliphatic, heteroaliphatic, aryl or heteroaryl moiety;
$R^C$ is hydrogen; aliphatic; heteroaliphatic; aryl; heteroaryl; halogen; cyano; alkyloxycarbonyl; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety, and wherein each occurrence of $R^L$ and $R^M$ is independently hydrogen, or an aliphatic, heteroaliphatic, aryl or heteroaryl moiety;

each occurrence of $R^9$ and $R^5$ is independently hydrogen; aliphatic; heteroaliphatic; aryl; heteroaryl; cyano; —C(O)$R^J$; —C(O)O$R^J$; —$NR^J$C(O)O$R^K$; —OC(O)$R^J$; —$NR^J$SO$_2R^K$; —SO$_2NR^JR^K$; —$NR^J$C(O)$R^K$; —C(O)$NR^J R^K$; —CH=NO$R^J$; —S(O)$_n R^J$, wherein n is an integer from 0 to 2; —(CR$^L$CR$^M$)$_u$—C_CR$^J$; or —Z$R^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L R^M$, —CO(NOR$^L$)R$^M$, —CH=NOR$^J$, —NR$^L R^M$, —S(O)$_2 R^L$, —P(O)(OR$^L$)R$^M$, or an aliphatic, heteroaliphatic, aryl or heteroaryl moiety;

$R^7$ is hydrogen; aliphatic; heteroaliphatic; aryl; heteroaryl; cyano; —C(O)$R^J$; —C(O)O$R^J$; —NR$^J$C(O)OR$^K$; —OC(O)R$^J$; —NR$^J$SO$_2 R^K$; —SO$_2$NR$^J R^K$; —NR$^J$C(O)R$^K$; —C(O)NR$^J R^K$; —CH=NOR$^J$; —S(O)$_n R^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L R^M$, —CO(NOR$^L$)R$^M$, —CH=NOR$^J$, —NR$^L R^M$, —S(O)$_2 R^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of R$^P$ and R$^Q$ is independently hydrogen or an aliphatic moiety; each occurrence of n is independently 0–3;

q is an integer from 0 to 5;

p is an integer from 0–3;

r is an integer from 0–2;

R$^{9a}$ is hydrogen; or an aliphatic or heteroaliphatic moiety;

each occurrence of PCM is independently a phosphorus-containing moiety;

t is an integer from 1–3;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and R$^B$ optionally additionally comprises a phosphorus-containing moiety.

Another class of compounds of interest include those compounds of the structure of Formula Ib (and pharmaceutically acceptable derivatives thereof):

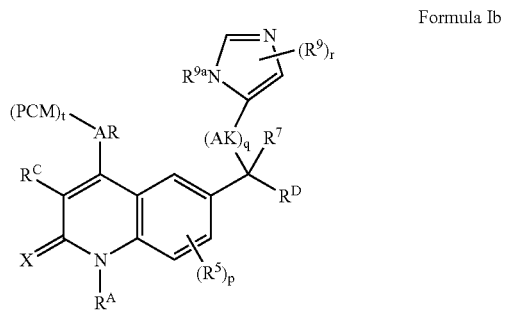

Formula Ib wherein AR is an aryl or heteroaryl moiety;

X is oxygen or sulfur;

R$^A$ is hydrogen, aliphatic, heteroaliphatic, aryl or heteroaryl moiety;

R$^C$ is hydrogen; aliphatic; heteroaliphatic; aryl; heteroaryl; halogen; cyano; alkyloxycarbonyl; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L R^M$, —CO(NOR$^L$)R$^M$, —CH=NOR$^J$, —NR$^L R^M$, —S(O)$_2 R^L$, —P(O)(OR$^L$)R$^M$, or an aliphatic, heteroaliphatic, aryl or heteroaryl moiety, and wherein each occurrence of R$^L$ and R$^M$ is independently hydrogen, or an aliphatic, heteroaliphatic, aryl or heteroaryl moiety;

R$^D$ is an aryl or heteroaryl moiety;

each occurrence of R$^9$ and R$^5$ is independently hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2 R^K$; —SO$_2$NR$^J R^K$; —NR$^J$C(O)R$^K$; —C(O)NR$^J R^K$; —CH=NOR$^J$; —S(O)$_n R^J$, wherein n is an integer from 0 to 2; —(CR$^L$CR$_M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L R^M$, —CO(NOR$^L$)R$^M$, —CH=NOR$^J$, —NR$^L R^M$, —S(O)$_2 R^L$, —P(O)(OR$^L$)R$^M$; or an aliphatic, heteroaliphatic, aryl or heteroaryl moiety;

R$^7$ is hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2 R^K$; —SO$_2$NR$^J R^K$; —NR$^J$C(O)R$^K$; —C(O)NR$^J R^K$; —CH=NOR$^J$; —S(O)$_n R^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L R^M$, —CO(NOR$^L$)R$^M$, —CH=NOR$^J$, —NR$^L R^M$, —S(O)$_2 R^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of R$^P$ and R$^Q$ is independently hydrogen or an aliphatic moiety; each occurrence of n is independently 0–3;

q is an integer from 0 to 5;

p is an integer from 0–3;

r is an integer from 0–2;

R$^{9a}$ is hydrogen; or an aliphatic or heteroaliphatic moiety;

each occurrence of PCM is independently a phosphorus-containing moiety;

t is an integer from 1–3;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and R$^D$ optionally additionally comprises a phosphorus-containing moiety.

Another class of compounds of interest include those compounds of the structure of Formula Ic (and pharmaceutically acceptable derivatives thereof):

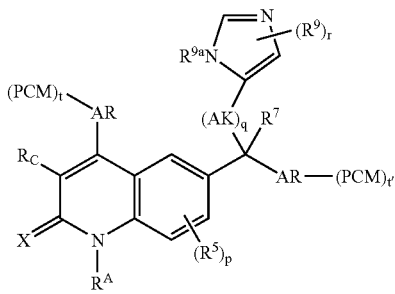

Formula Ic wherein each occurrence of AR is independently an aryl or heteroaryl moiety;

X is oxygen or sulfur;

$R^A$ is hydrogen, aliphatic, heteroaliphatic, aryl or heteroaryl moiety;

$R^C$ is hydrogen; aliphatic; heteroaliphatic; aryl; heteroaryl; halogen; cyano; alkyloxycarbonyl; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO(NOR$^L$)$R^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety, and wherein each occurrence of $R^L$ and $R^M$ is independently hydrogen, or an aliphatic, heteroaliphatic, aryl or heteroaryl moiety;

each occurrence of $R^9$ and $R^5$ is independently hydrogen; aliphatic; heteroaliphatic; aryl; heteroaryl; cyano; —C(O)$R^J$; —C(O)O$R^J$; —N$R^J$C(O)O$R^K$; —OC(O)$R^J$; —N$R^J$SO$_2$R$^K$; —SO$_2$N$R^J$R$^K$; —N$R^J$C(O)$R^K$; —C(O)N$R^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of $R^J$ and $R^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

$R^7$ is hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of R$^P$ and R$^Q$ is independently hydrogen or an aliphatic moiety; each occurrence of n is independently 0–3;

q is an integer from 0 to 5;

p is an integer from 0–3;

r is an integer from 0–2;

R$^{9a}$ is hydrogen; or an aliphatic or heteroaliphatic moiety;

PCM, for each occurrence, is independently a phosphorus-containing moiety;

t and t' are each independently an integer from 0–3;

wherein the sum t+t' is at least 1;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

In certain other subsets of interest for compounds as described in Formulas Ia–Ic above, AR is an aryl or heteroaryl moiety selected from phenyl, pyridyl, pyrrole, furan, thiophene, imidazole, oxazole, thiazole, pyrazole and pyrimidine, optionally further substituted with one or more occurrences of R$^3$, as defined herein.

A subclass of special interest of compounds of Formula Ia described above, consists of compounds having the structure of Formula Id (and pharmaceutically acceptable derivatives thereof) in which AR is a phenyl moiety substituted with a phosphorus-containing moiety:

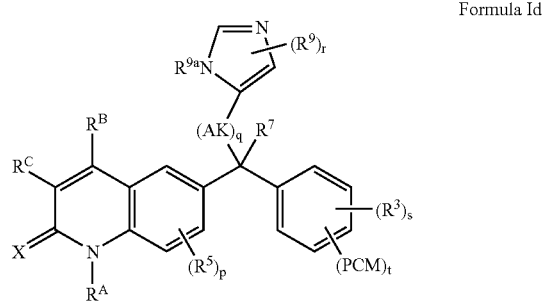

Formula Id

X is oxygen or sulfur;

R$^A$ is hydrogen, aliphatic, heteroaliphatic, aryl or heteroaryl moiety;

R$^B$ is an aliphatic, heteroaliphatic, aryl or heteroaryl moiety;

R$^C$ is hydrogen; aliphatic; heteroaliphatic; aryl; heteroaryl; halogen; cyano; alkyloxycarbonyl; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety, and wherein each occurrence of R$^L$ and R$^M$ is independently hydrogen, or an aliphatic, heteroaliphatic, aryl or heteroaryl moiety;

each occurrence of R$^9$ and R$^5$ is independently hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

R$^7$ is hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of R$^P$ and R$^Q$ is independently hydrogen or an aliphatic moiety; each occurrence of n is independently 0–3;

q is an integer from 0 to 5;

p is an integer from 0–3;

r is an integer from 0–2;

R$^{9a}$ is hydrogen; or an aliphatic or heteroaliphatic moiety;

each occurrence of R$^3$ is independently hydrogen; halogen; R$^1$; —GR$^1$; —CO(Y'R$^1$); acylamino, amido, amidino, cyano, nitro, azido, sulfonyl, sulfoxido, sulfate, sulfonate, sulfamoyl, or sulfonamido; wherein each occurrence of Y' is independently —O—, —S—, —NR$^1$—, —C(O)—, —COO— or S(O)$_2$; each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H; each occurrence of G is independently absent, or is —O—, —S—, —NR$^1$— or (M)$_x$; each occurrence of M is independently a substituted or unsubstituted methylene moiety, and any M-M' moiety may be electronically saturated or unsaturated; and each occurrence of x is independently an integer from 0–6;

s is an integer from 0–3;

each occurrence of PCM is independently a phosphorus-containing moiety;

t is an integer from 1–3;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and R$^B$ optionally additionally comprises a phosphorus-containing moiety.

A subclass of special interest of compounds of Formula Ib described above, consists of compounds having the structure of Formula Ie (and pharmaceutically acceptable derivatives thereof) in which AR is a phenyl moiety substituted with a phosphorus-containing moiety:

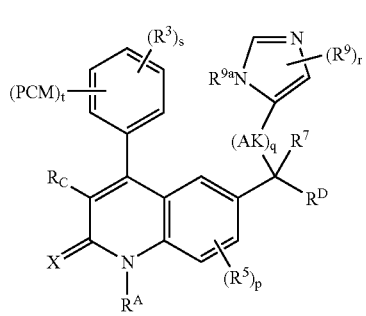

Formula Ie wherein X is oxygen or sulfur;

R$^A$ is hydrogen, aliphatic, heteroaliphatic, aryl or heteroaryl moiety;

R$^C$ is hydrogen; aliphatic; heteroaliphatic; aryl; heteroaryl; halogen; cyano; alkyloxycarbonyl; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety, and wherein each occurrence of R$^L$ and R$^M$ is independently hydrogen, or an aliphatic, heteroaliphatic, aryl or heteroaryl moiety;

each occurrence of R$^9$ and R$^5$ is independently hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, P(O)(OR$^L$)R$^M$, or an aliphatic, heteroaliphatic, aryl or heteroaryl moiety;

R$^7$ is hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^1$, wherein each occurrence of Z is independently —O—, —S—, NR$^K$, —C(O)—, —S(O)$_2$—, or —COO—, wherein each occurrence of R$^J$ and R$^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of R$^P$ and R$^Q$ is independently hydrogen or an aliphatic moiety; each occurrence of n is independently 0–3;

q is an integer from 0 to 5;

p is an integer from 0–3;

r is an integer from 0–2;

R$^{9a}$ is hydrogen; or an aliphatic or heteroaliphatic moiety;

each occurrence of R$^3$ is independently hydrogen; halogen; R$^1$; —GR$^1$; —CO(Y'R$^1$); acylamino, amido, amidino, cyano, nitro, azido, sulfonyl, sulfoxido, sulfate, sulfonate, sulfamoyl, or sulfoynamido; wherein each occurrence of Y' is independently —O—, —S—, —NR$^1$—, —C(O)—, —COO— or S(O)$_2$; each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H; each occurrence of G is independently absent, or is —O—, —S—, —NR$^1$— or (M)$_x$; each occurrence of M is independently a substituted or unsubstituted methylene moiety, and any M-M' moiety may be electronically saturated or unsaturated; and each occurrence of x is independently an integer from 0–6;

s is an integer from 0–3;

PCM is a phosphorus-containing moiety;

t is an integer from 1–3;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and R$^D$ optionally additionally comprises a phosphorus-containing moiety.

A subclass of special interest of compounds of Formula Ic described above, consists of compounds having the structure of Formula If (and pharmaceutically acceptable derivatives thereof) in which each AR moiety is independently a phenyl moiety substituted with a phosphorus-containing moiety:

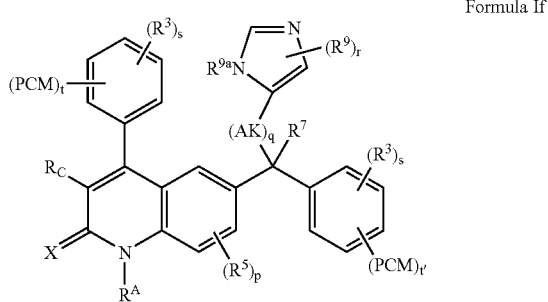

Formula If wherein X is oxygen or sulfur;

$R^A$ is hydrogen, aliphatic, heteroaliphatic, aryl or heteroaryl moiety;

$R^C$ is hydrogen; aliphatic; heteroaliphatic; aryl; heteroaryl; halogen; cyano; alkyloxycarbonyl; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —CO(NOR$^L$)$R^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety, and wherein each occurrence of $R^L$ and $R^M$ is independently hydrogen, or an aliphatic, heteroaliphatic, aryl or heteroaryl moiety;

each occurrence of $R^9$ and $R^5$ is independently hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of $R^J$ and $R^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

$R^7$ is hydrogen; aliphatic; heteroaliphatic; aryl; heteroaryl; cyano; —C(O)R$^J$; —C(O)OR$^J$; —NR$^J$C(O)OR$^K$; —OC(O)R$^J$; —NR$^J$SO$_2$R$^K$; —SO$_2$NR$^J$R$^K$; —NR$^J$C(O)R$^K$; —C(O)NR$^J$R$^K$; —CH=NOR$^J$; —S(O)$_n$R$^J$, wherein n is an integer from 0 to 2; —(CR$^L$CR$^M$)$_u$—C_CR$^J$; or —ZR$^J$, wherein each occurrence of Z is independently —O—, —S—, NR$^K$, —C(O)—, —S(O)$_2$—, or —COO—, wherein each occurrence of $R^J$ and $R^K$ is independently hydrogen, COR$^L$, COOR$^L$, CONR$^L$R$^M$, —CO(NOR$^L$)R$^M$, —CH=NOR$^J$, —NR$^L$R$^M$, —S(O)$_2$R$^L$, —P(O)(OR$^L$)R$^M$, or an aliphatic, heteroaliphatic, aryl or heteroaryl moiety;

u is an integer from 0–6;

AK is (CR$^P$CR$^Q$);

each occurrence of $R^P$ and $R^Q$ is independently hydrogen or an aliphatic moiety; each occurrence of n is independently 0–3;

q is an integer from 0 to 5;

p is an integer from 0–3;

r is an integer from 0–2;

$R^{9a}$ is hydrogen; or an aliphatic or heteroaliphatic moiety;

each occurrence of $R^3$ is independently hydrogen; halogen; $R^1$; —GR$^1$; —CO(Y'R$^1$); acylamino, amido, amidino, cyano, nitro, azido, sulfonyl, sulfoxido, sulfate, sulfonate, sulfamoyl, or sulfonamido; wherein each occurrence of Y' is independently —O—, —S—, —NR$^1$—, —C(O)—, —COO— or S(O)$_2$; each occurrence of $R^1$ is independently a substituted or unsubstituted aliphatic, heteroaliphatic, aryl or heteroaryl moiety, or, except in YR$^1$ moieties in which Y is a covalent bond, $R^1$ may also be H; each occurrence of G is independently absent, or is —O—, —S—, —NR$^1$— or (M)$_x$; each occurrence of M is independently a substituted or unsubstituted methylene moiety, and any M-M' moiety may be electronically saturated or unsaturated; and each occurrence of x is independently an integer from 0–6;

each occurrence of s is independently an integer from 0–3;

each occurrence of PCM is independently a phosphorus-containing moiety;

t and t' are each independently an integer from 0–3;

wherein the sum t+t' is at least 1;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

In certain subsets of interest for Formulas Ia and Id, as described above, and other subsets of interest as described herein, $R^B$ is an aryl or heteroaryl moiety substituted independently with one or more occurrences of hydrogen, halogen, cyano, hydroxy, or alkoxy. In other subsets each occurrence of $R^9$ and $R^5$ are each hydrogen. In still other subsets $R^7$ is NH$_2$ or N(alkyl)$_2$. In still other subsets $R^A$ is hydrogen or an aliphatic moiety. In yet other subsets $R^A$ is hydrogen or a $C_{1-6}$ linear alkyl moiety or is a $C_5$ or $C_6$ cyclic alkyl moiety. In still other subsets of compounds as described above and herein, $R^{9a}$ is hydrogen or an aliphatic or heteroaliphatic moiety. In certain other subsets $R^{9a}$ is hydrogen or a $C_{1-6}$ alkyl or heteroalkyl moiety. In yet other subsets of interest $R^{9a}$ is hydrogen, methyl or ethyl.

In certain other subsets of interest for Formulas Ib and Ie, as described above, and other subsets of interest as described herein $R^D$ is an aryl or heteroaryl moiety substituted independently with one or more occurrences of hydrogen, halogen, cyano, hydroxy, or alkoxy. In other subsets each occurrence of $R^9$ and $R^5$ are each hydrogen. In still other subsets $R^7$ is —NH$_2$, —OH, —N(alkyl)$_2$ or —Oalkyl. In still other subsets $R^A$ is an aliphatic moiety. In yet other subsets $R^A$ is a $C_{1-6}$ linear alkyl moiety or is a $C_5$ or $C_6$ cyclic alkyl moiety. In still other subsets of compounds as described above and herein, $R^{9a}$ is an aliphatic or heteroaliphatic moiety. In certain other subsets $R^{9a}$ is a $C_{1-6}$ alkyl or heteroalkyl moiety. In yet other subsets of interest $R^{9a}$ is hydrogen, methyl or ethyl.

In certain other subsets of interest for Formulas Ic and If, as described above, and other subsets of interest as described herein, each phenyl moiety is substituted independently with one or more occurrences of hydrogen, halogen, cyano, hydroxy, or alkoxy. In other subsets each occurrence of $R^9$ and $R^5$ are each hydrogen. In still other subsets $R^7$ is —NH$_2$, —OH, —N(alkyl)$_2$ or —Oalkyl. In still other subsets $R^A$ is an aliphatic moiety. In yet other subsets $R^A$ is a $C_{1-6}$ linear alkyl moiety or is a $C_5$ or $C_6$ cyclic alkyl moiety. In still other subsets of compounds as described above and herein, $R^{9a}$ is an aliphatic or heteroaliphatic moiety. In certain other subsets $R^{9a}$ is a $C_{1-6}$ alkyl or heteroalkyl moiety. In yet other subsets of interest $R^{9a}$ is hydrogen, methyl or ethyl. In still other subsets, if $R^B$ (or specific substituents, e.g., AR, phenyl, as further defined for $R^B$) is a phenyl moiety where t is 0 and thus $R^B$ does not comprise a phosphorus-containing moiety, then one or more occurrences of $R^3$ is OH, alkoxy, or halogen. In yet other subsets if $R^D$ (or specific substituents, e.g., AR, phenyl, as further defined for $R^D$) is a phenyl moiety where t' is 0 and thus $R^D$ does not comprise a phosphorus-containing moiety, then one or more occurrences of $R^3$ is OH, alkoxy, or halogen.

In yet another subset of compounds of particular interest, X is oxygen, $R^7$ is $NH_2$ and the compound has the structure of Formula Ig (and pharmaceutically acceptable derivatives thereof):

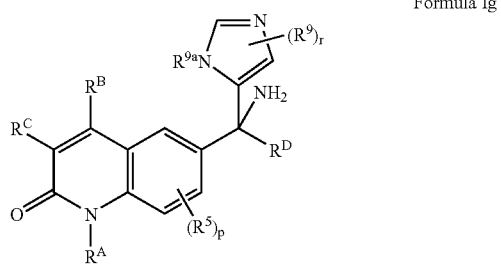

Formula Ig wherein is hydrogen, aliphatic, heteroaliphatic, aryl or heteroaryl moiety;

$R^B$ is an aliphatic, heteroaliphatic, aryl or heteroaryl moiety;

$R^C$ is hydrogen; aliphatic; heteroaliphatic; aryl; heteroaryl; halogen; cyano; alkyloxycarbonyl; or $-ZR^J$, wherein each occurrence of Z is independently $-O-$, $-S-$, $NR^K$, $-C(O)-$, $-S(O)_2-$, or $-COO-$, wherein each occurrence of $R^J$ and $R^K$ is independently hydrogen, $COR^L$, $COOR^L$, $CONR^LR^M$, $-CO(NOR^L)R^M$, $-CH=NOR^J$, $-NR^LR^M$, $-S(O)_2R^L$, $-P(O)(OR^L)R^M$, or an aliphatic, heteroaliphatic, aryl or heteroaryl moiety, and wherein each occurrence of $R^L$ and $R^M$ is independently hydrogen, or an aliphatic, heteroaliphatic, aryl or heteroaryl moiety;

$R^D$ is an aryl or heteroaryl moiety;

each occurrence of $R^9$ and $R^5$ is independently hydrogen; aliphatic; heteroaliphatic; aryl; heteroaryl; cyano; $-C(O)R^J$; $-C(O)OR^J$; $-NR^JC(O)OR^K$; $-OC(O)R^J$; $-NR^JSO_2R^K$; $-SO_2NR^JR^K$; $-NR^JC(O)R^K$; $-C(O)NR^JR^K$; $-CH=NOR^J$; $-S(O)_nR^J$, wherein n is an integer from 0 to 2; $-(CR^LCR^M)_u-C\_CR^J$; or $-ZR^J$, wherein each occurrence of Z is independently $-O-$, $-S-$, $NR^K$, $-C(O)-$, $-S(O)_2-$, or $-COO-$, wherein each occurrence of $R^J$ and $R^K$ is independently hydrogen, $COR^L$, $COOR^L$, $CONR^LR^M$, $-CO(NOR^L)R^M$, $-CH=NOR^J$, $-NR^LR^M$, $-S(O)_2R^L$, $P(O)(OR^L)R^M$, or an aliphatic, heteroaliphatic, aryl or heteroaryl moiety;

$R^7$ is hydrogen; aliphatic; heteroaliphatic; aryl; heteroaryl; cyano; $-C(O)R^J$; $-C(O)OR^J$; $-NR^JC(O)OR^K$; $-OC(O)R^J$; $-NR^JSO_2R^K$; $-SO_2NR^JR^K$; $-NR^JC(O)R^K$; $-C(O)NR^JR^K$; $-CH=NOR^J$; $-S(O)_nR^J$, wherein n is an integer from 0 to 2; $-(CR^LCR^M)_u-C\_CR^J$; or $-ZR^J$, wherein each occurrence of Z is independently $-O-$, $-S-$, $NR^K$, $-C(O)-$, $-S(O)_2-$, or $-COO-$, wherein each occurrence of $R^J$ and $R^K$ is independently hydrogen, $COR^L$, $COOR^L$, $CONR^LR^M$, $-CO(NOR^L)R^M$, $-CH=NOR^J$, $-NR^LR^M$, $-S(O)_2R^L$, $-P(O)(OR^L)R^M$, or an aliphatic, heteroaliphatic, aryl or heteroaryl moiety;

u is an integer from 0–6;

AK is $(CR^PCR^Q)$;

each occurrence of $R^P$ and $R^Q$ is independently hydrogen or an aliphatic moiety;

q is an integer from 0 to 5;

p is an integer from 0–3;

r is an integer from 0–2;

$R^{9a}$ is hydrogen; or an aliphatic or heteroaliphatic moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and at least one of $R^B$ or $R^D$ as defined above, comprises a phosphorus-containing moiety.

In certain embodiments for Formulas Ia–Ig, as described above, one or both of $R^B$ or $R^D$ (or specific substituents, e.g., AR, phenyl, as further defined for $R^B$ and $R^D$) comprises or is substituted with a phosphorus-containing moiety of Series I:

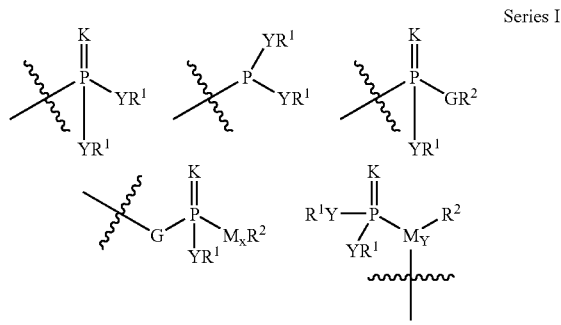

Series I wherein each occurrence of K is independently O or S;

each occurrence of Y is independently $-O-$, $-S-$, $-NH-$, $-NR^1-$, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, $-PK(YR^1)(YR^1)$, $-SO_2(YR^1)$ or $-C(O)(YR^1)$;

each occurrence of G is independently absent, or is $-O-$, $-S-$, $-NR^1-$ or $(M)_x$;

each occurrence of M is independently a substituted or unsubstituted methylene moiety, and any M-M' moiety may be electronically saturated or unsaturated;

each occurrence of x is independently an integer from 0–6; and each occurrence of $M_Y$ is independently a methine group or a lower alkyl moiety which contains a methine group and optionally may be further substituted.

In certain other embodiments, the phosphorus-containing moiety of Formulas Ia–Ig is selected from Series Ia or Ib below:

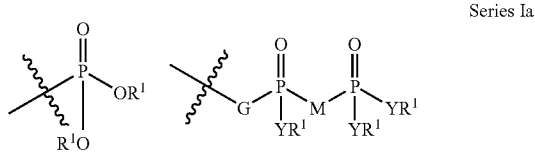

Series Ia

-continued

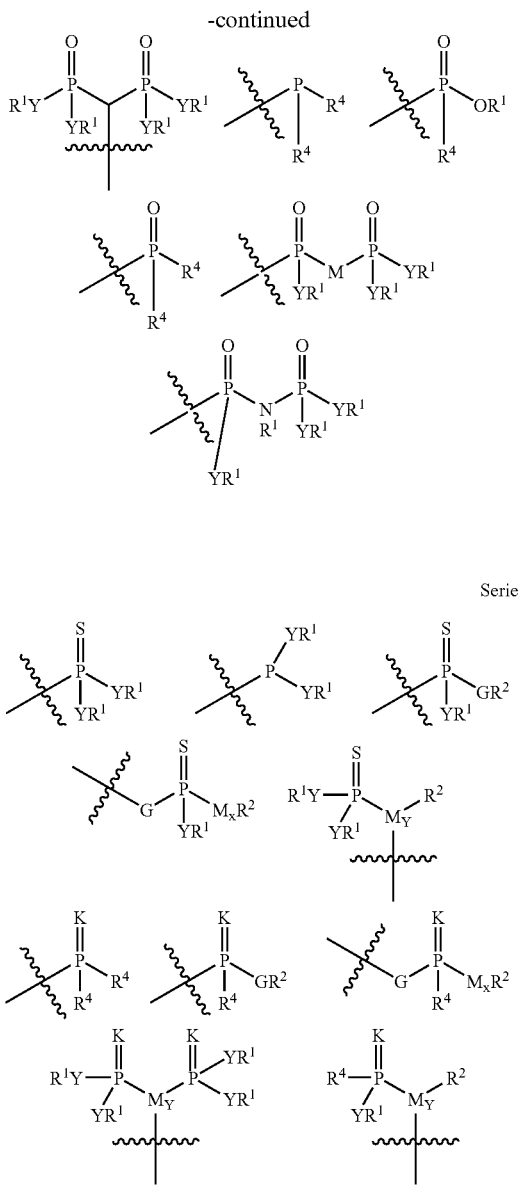

Series Ib wherein each occurrence of K is independently O or S;

each occurrence of Y is independently —O—, —S—, —NH—, —NR$^1$—, or a chemical bond linking R$^1$ to P;

each occurrence of R$^1$ is independently a substituted or unsubstituted aliphatic, heteroaliphatic, aryl, alkylaryl, or alkylheteroaryl moiety, or, except in YR$^1$ moieties in which Y is a covalent bond, R$^1$ may also be H;

each occurrence of R$^2$ is independently R$^1$, —PK(YR$^1$)(YR$^1$), —SO$_2$(YR$^1$) or —C(O)(YR$^1$);

each occurrence of G is independently absent, or is —O—, —S—, —NR$^1$— or (M)$_x$;

each occurrence of M is independently a substituted or unsubstituted methylene moiety, and any M-M' moiety may be electronically saturated or unsaturated;

each occurrence of x is independently an integer from 0–6; and each occurrence of M$_Y$ is independently a methine group or a lower alkyl moiety which contains a methine group and optionally may be further substituted; and each occurrence of R$^4$ is independently an aliphatic, heteroaliphatic, aryl or heteroaryl moiety. In certain embodiments, M is —CR$_x$R$_y$, wherein each occurrence of R$_x$ and R$_y$ is independently hydrogen, halogen, alkyl, heteroalkyl, OR$^L$ or NR$^L$R$^M$; wherein each occurrence of R$^L$ and R$^M$ is independently hydrogen, or an alkyl, heteroalkyl, aryl or heteroaryl moiety. In certain exemplary embodiments, M is —CH$_2$—, —CH(OH)—, —CH(NH$_2$)—, —C(alkyl)(OH)—, —C(alkyl)(NH$_2$)—, —CH(halo)— or —C(halo)$_2$—.

In certain other embodiments, the phosphorus-containing moiety of Formulas Ia–Ig is selected from Series Ic depicted below:

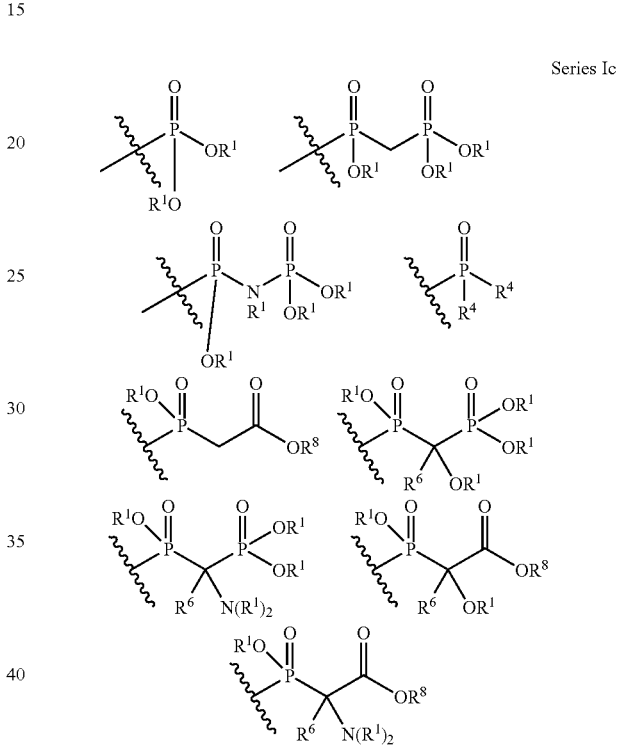

Series Ic wherein each occurrence of R$^1$ is independently hydrogen, alkyl or aryl;

each occurrence of R$^4$ is independently alkyl or aryl;

each occurrence of R$^6$ is independently hydrogen, alkyl, heteroalkyl, aryl or heteroaryl; and each occurrence of R$^8$ is independently hydrogen, alkyl, heteroalkyl, aryl or heteroaryl, or a prodrug moiety.

In certain embodiments, R$^6$ is hydrogen, lower alkyl, OR$^L$ or NR$^L$R$^M$; wherein each occurrence of R$^L$ and R$^M$ is independently hydrogen, or an alkyl, heteroalkyl, aryl or heteroaryl moiety. In certain other embodiments, R$^6$ is hydrogen, methyl, ethyl, OH or NH$_2$. In certain embodiments, R$^8$ is hydrogen, lower alkyl, lower heteroalkyl, aryl, heteroaryl or a prodrug moiety. In still other embodiments, R$^8$ is hydrogen, methyl, ethyl, or a prodrug moiety.

In certain other embodiments, for each of the foregoing classes of Formulas Ib–If as described above, either or both of R$^B$ or R$^D$ (or specific substituents as further defined for R$^B$ and R$^D$, e.g., AR, phenyl) comprises or is substituted with any one of the phosphorus-containing aryl of heteroaryl moieties of Series II:

Series II

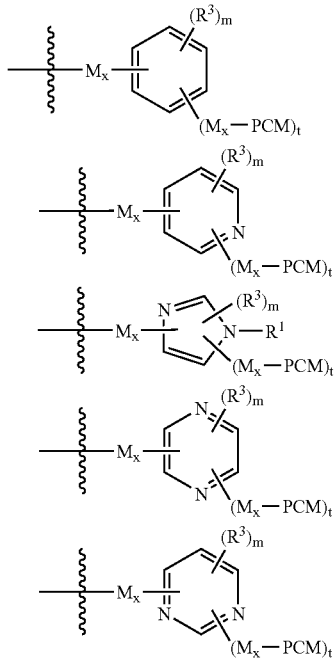

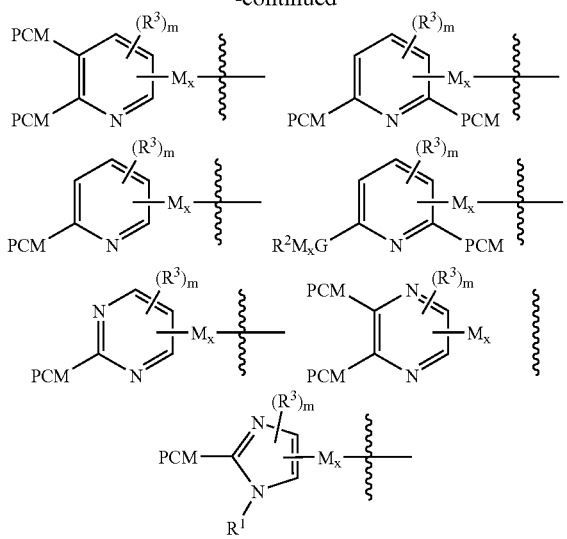

wherein each occurrence of R³ is independently hydrogen; halogen; —CN; NO₂; N₃; R¹; —GR¹; —CO(Y'R¹); —NR¹(Y'R¹); S(O)₂(Y'R¹); wherein each occurrence of Y' is independently —O—, —S—, —NR¹—, —C(O)—, —COO— or S(O)₂; and each occurrence of G is independently absent, or is —O—, —S—, —NR¹, S(O)₂, or (M)ₓ;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of M is independently a substituted or unsubstituted methylene moiety, and any M-M' moiety may be electronically saturated or unsaturated;

each occurrence of x is independently an integer from 0–6;

PCM is a phosphorus-containing moiety of Series I, Series Ia, Series Ib; or Series Ic, and m is an integer from 0–3, t is an integer from 1–3, and the sum of m+t is an integer from 1–5.

In still other embodiments, for each of the foregoing classes of Formulas Ib–If as described above, either or both of $R^B$ or $R^D$ (or specific substituents as further defined for $R^B$ and $R^D$, e.g., AR, phenyl) comprises any one of the phosphorus-containing aryl of heteroaryl moieties of Series Ia:

Series IIa

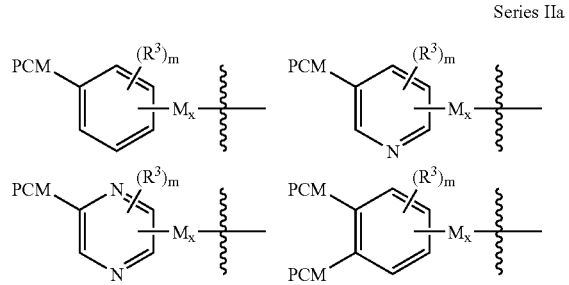

wherein each occurrence of R³ is independently hydrogen; halogen; —CN; NO₂; N₃; R¹; —GR¹; —CO(Y'R¹); —NR¹(Y'R¹); S(O)₂(Y'R¹); wherein each occurrence of Y' is independently —O—, —S—, —NR¹—, —C(O)—, —COO— or S(O)₂;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of R² is independently R¹, —PK(YR¹)(YR¹), —SO₂(YR¹) or —C(O)(YR¹); wherein each occurrence of Y is independently —O—, —S—, —NH—, —NR¹—, or a chemical bond linking R¹ to P;

each occurrence of G is independently absent, or is —O—, —S—, —NR¹—, S(O)₂, or (M)ₓ;

each occurrence of M is independently a substituted or unsubstituted methylene moiety, and any M-M' moiety may be electronically saturated or unsaturated;

each occurrence of x is independently an integer from 0–6;

m is an integer from 0–3; and

PCM is a phosphorus-containing moiety of Series I, Series Ia, Series Ib or Series Ic.

In certain exemplary embodiments, PCM is independently, for each occurrence, a phosphorus-containing moiety of Series Ic depicted below:

Series Ic

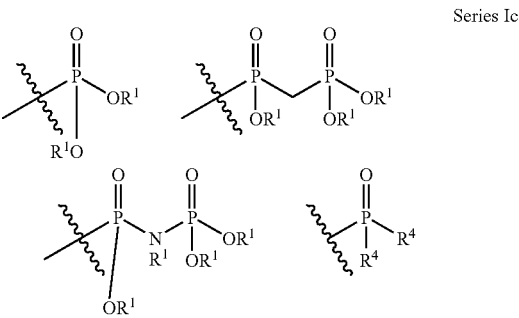

-continued

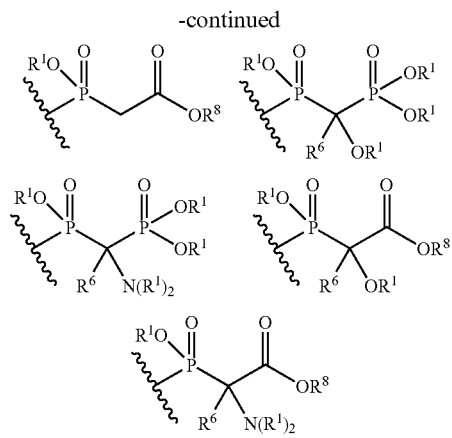

wherein each occurrence of $R^1$ is independently hydrogen, alkyl or aryl;

each occurrence of $R^4$ is independently alkyl or aryl;

each occurrence of $R^6$ is independently hydrogen, alkyl, heteroalkyl, aryl or heteroaryl; and each occurrence of $R^8$ is independently hydrogen, alkyl, heteroalkyl, aryl or heteroaryl, or a prodrug moiety.

In certain embodiments, $R^6$ is hydrogen, lower alkyl, $OR^L$ or $NR^LR^M$; wherein each occurrence of $R^L$ and $R^M$ is independently hydrogen, or an alkyl, heteroalkyl, aryl or heteroaryl moiety. In certain other embodiments, $R^6$ is hydrogen, methyl, ethyl, OH or $NH_2$. In certain embodiments, $R^8$ is hydrogen, lower alkyl, lower heteroalkyl, aryl, heteroaryl or a prodrug moiety. In still other embodiments, $R^8$ is hydrogen, methyl, ethyl, or a prodrug moiety.

In still other embodiments, for each of the foregoing classes of Formulas Ib–If as described above, either or both of $R^B$ or $R^D$ (or specific substituents as further defined for $R^B$ and $R^D$, e.g., AR, phenyl) comprises any one of the phosphorus-containing aryl of heteroaryl moieties of Series IIb:

Series IIb

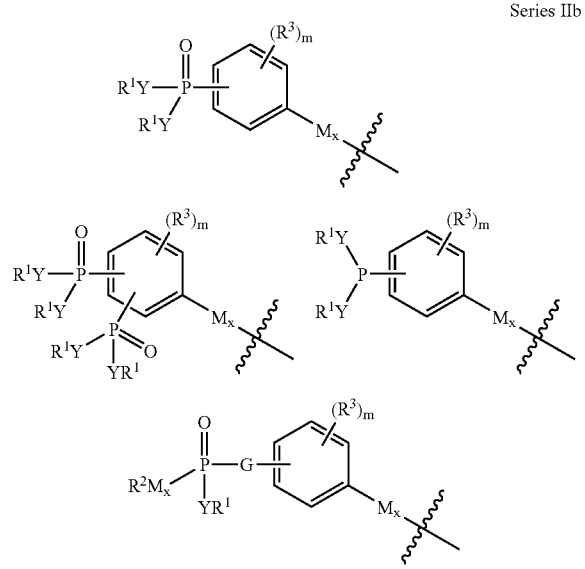

-continued

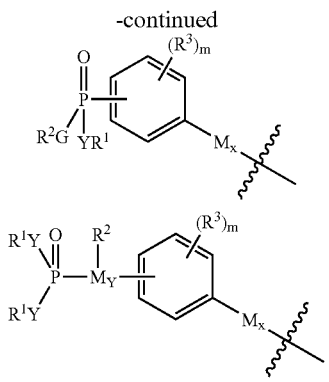

wherein each occurrence of $R^3$ is independently hydrogen; halogen; —CN; $NO_2$; $N_3$; $R^1$; —$GR^1$; —$CO(Y'R^1)$; —$NR^1(Y'R^1)$; $S(O)_2(Y'R^1)$; wherein each occurrence of Y' is independently —O—, —S—, —$NR^1$—, —C(O)—, —COO— or $S(O)_2$;

each occurrence of $R^2$ is independently $R^1$, —$PK(YR^1)(YR^1)$, —$SO_2(YR^1)$ or —$C(O)(YR^1)$;

each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of G is independently absent, or is —O—, —S—, —$NR^1$, $S(O)_2$, or $(M)_x$;

each occurrence of $M_Y$ is independently a methine group or a lower alkyl moiety which contains a methine group and optionally may be further substituted;

each occurrence of M is independently a substituted or unsubstituted methylene moiety, and any M-M' moiety may be electronically saturated or unsaturated;

each occurrence of x is independently an integer from 0–6; and m is an integer from 0–3.

In still other embodiments, for each of the foregoing classes of Formulas Ib–If as described above, either or both of $R^B$ or $R^D$ (or specific substituents as further defined for $R^B$ and $R^D$, e.g., AR, phenyl) comprises any one of the phosphorus-containing aryl of heteroaryl moieties of Series III:

Series III

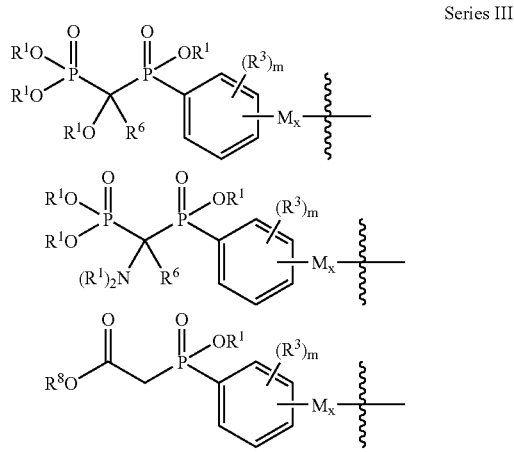

-continued

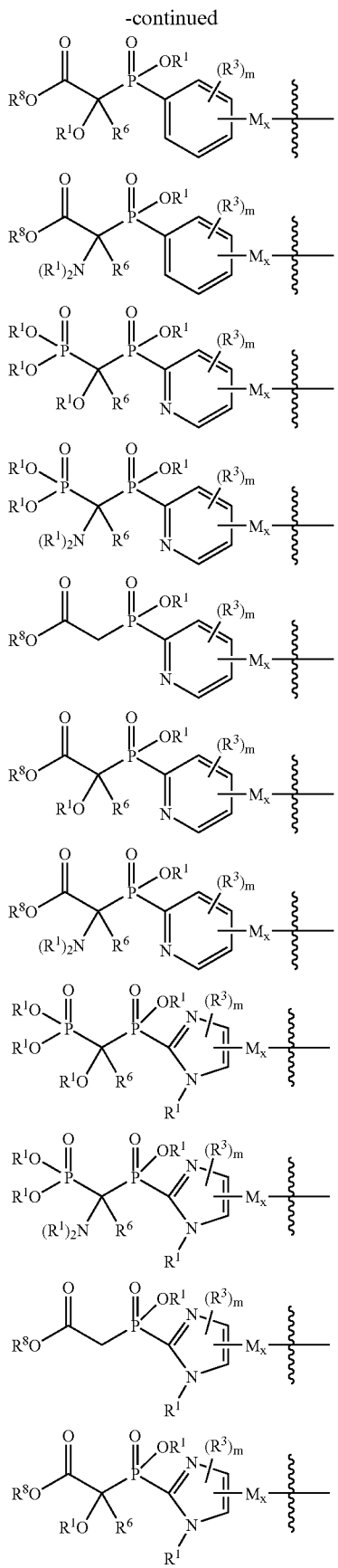

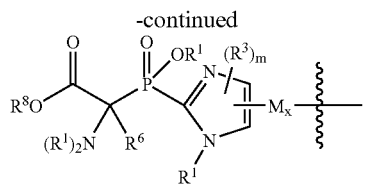

wherein each occurrence of $R^3$ is independently hydrogen; halogen; —CN; $NO_2$; $N_3$; $R^1$; —$GR^1$; —$CO(Y'R^1)$; —$NR^1(Y'R^1)$; $S(O)_2(Y'R^1)$; wherein each occurrence of Y' is independently —O—, —S—, —$NR^1$—, —C(O)—, —COO— or $S(O)_2$; each occurrence of G is independently absent, or is —O—, —S—, —$NR^1$—, $S(O)_2$, or $(M)_x$; and m is an integer from 0–4;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

each occurrence of $R^6$ is independently hydrogen, aliphatic, heteroaliphatic, aryl or heteroaryl moiety; and each occurrence of $R^8$ is independently hydrogen, an aliphatic, heteroaliphatic, aryl or heteroaryl moiety, or a prodrug moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

It will be appreciated that, in certain exemplary embodiments, for each of the foregoing classes of Formulas Ib–If as described above, both $R^B$ and $R^D$ (or specific substituents as further defined for $R^B$ and $R^D$, e.g., AR, phenyl) independently comprises or is substituted with a phosphorus-containing moiety of Series I, Ia, Ib, Ic, I, IIa or IIb. In certain other embodiments, either or both $R^B$ and $R^D$ comprises or is substituted with a phosphorus-containing moiety of Series I as depicted below:

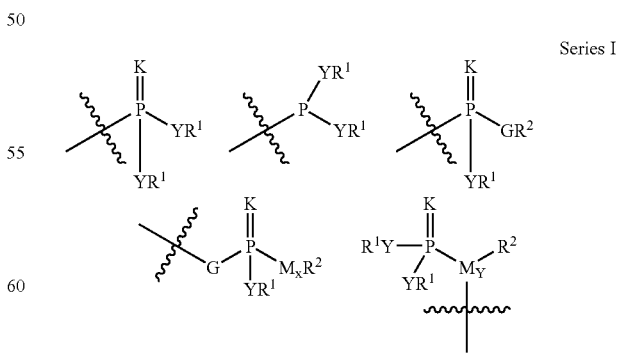

Series I wherein each occurrence of K is independently O or S;
each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —PK($YR^1$)($YR^1$), —SO$_2$($YR^1$) or —C(O)($YR^1$);

each occurrence of G is independently absent, or is —O—, —S—, —NH—, —NR$^1$— or (M)$_x$;

each occurrence of M is independently a substituted or unsubstituted methylene moiety, and any M-M' moiety may be electronically saturated or unsaturated;

each occurrence of x is independently an integer from 0–6; and each occurrence of $M_y$ is independently a methine group or a lower alkyl moiety which contains a methine group and optionally may be further substituted.

It will be appreciated that in certain exemplary embodiments, both $R^B$ and $R^D$ as described directly above, comprises or is substituted with at least one of the phosphorus-containing moieties in Series Ic depicted below:

Series Ic

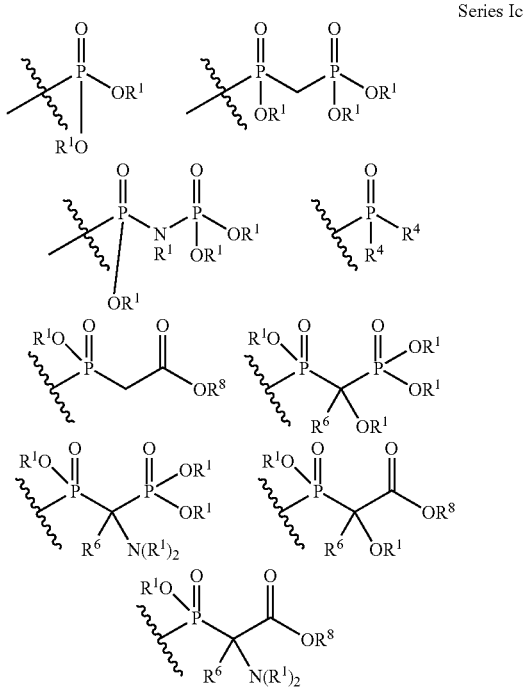

wherein each occurrence of $R^1$ is independently hydrogen, alkyl or aryl;

each occurrence of $R^4$ is independently alkyl or aryl;

each occurrence of $R^6$ is independently hydrogen, alkyl, heteroalkyl, aryl or heteroaryl; and each occurrence of $R^8$ is independently hydrogen, alkyl, heteroalkyl, aryl or heteroaryl, or a prodrug moiety.

In certain embodiments, $R^6$ is hydrogen, lower alkyl, $OR^L$ or $NR^L R^M$; wherein each occurrence of $R^L$ and $R^M$ is independently hydrogen, or an alkyl, heteroalkyl, aryl or heteroaryl moiety. In certain other embodiments, $R^6$ is hydrogen, methyl, ethyl, OH or NH$_2$. In certain embodiments, $R^8$ is hydrogen, lower alkyl, lower heteroalkyl, aryl, heteroaryl or a prodrug moiety. In still other embodiments, $R^8$ is hydrogen, methyl, ethyl, or a prodrug moiety.

In certain embodiments, for each of the compounds as described above and herein, Y is a chemical bond linking the phosphorus atom to $R^1$. In certain other embodiments Y is an oxygen atom. In still other embodiments, Y is a chemical bond linking the phosphorus atom to $R^1$ and $R^1$ is an alkyl group having 1–6 carbon atoms. In yet other subsets of the compounds as generally described above, $R^A$ is hydrogen or an aliphatic or heteroaliphatic moiety.

In certain embodiments, for each of the compounds as described above and herein, M is —CR$_x$R$_y$, wherein each occurrence of R$_x$ and R$_y$ is independently hydrogen, halogen, alkyl, heteroalkyl, OR$^L$ or NR$^L$R$^M$; wherein each occurrence of $R^L$ and $R^M$ is independently hydrogen, or an alkyl, heteroalkyl, aryl or heteroaryl moiety. In certain exemplary embodiments, x is 1 and M is —CH$_2$—, —CH(OH)—, —CH(NH$_2$)—, —C(alkyl)(OH)—, —C(alkyl)(NH$_2$)—, —CH(halo)— or —C(halo)$_2$—.

A number of important subclasses of the foregoing classes of compounds deserve separate mention. Those subclasses include subclasses of the foregoing classes in which:
i) Y is a chemical bond linking the phosphorus atom to $R^1$;
ii) Y is an oxygen atom;
iii) Y is an oxygen atom and $R^1$ is H;
iv) Y is a chemical bond linking the phosphorus atom to $R^1$, and $R^1$ is an alkyl group having 1–6 carbon atoms;
v) $R^1$ is a lower alkyl moiety;
vi) K is oxygen;
vii) X is oxygen;
viii) $R^A$ is hydrogen, oxygen or a lower alkyl moiety;
xix) $R^A$ is hydrogen;
x) $R^A$ is methyl, ethyl or propyl;
xi) $R^A$ is methyl
xii) AR, $R^B$ or $R^D$ comprises an aryl or heteroaryl moiety selected from phenyl, pyridyl, pyrrole, furan, thiophene, imidazole, oxazole, thiazole, pyrazole and pyrimidine; wherein each of the aryl or heteroaryl moieties is optionally substituted with one or more phosphorus-containing moieties, PCM, from Series I, Ia, Ib or Ic, and is optionally further substituted with one or more occurrences of $R^3$;
xiii) at least one of AR, $R^B$ or $R^D$ comprises a phosphorus-containing aryl or heteroaryl moiety from Series II, IIa or III, and is optionally further substituted with one or more occurrences of $R^3$;
xiv) $R^B$ is a subsituted or unsubstituted phenyl moiety; optionally substituted with one or more phosphorus-containing moieties, PCM, from Series I, Ia, Ib or Ic, and is optionally further substituted with one or more occurrences of $R^3$;
xv) $R^B$ is a substituted or unsubstituted pyridinyl moiety; optionally substituted with one or more phosphorus-containing moieties, PCM, from Series I, Ia, Ib or Ic, and is optionally further substituted with one or more occurrences of $R^3$;
xvi) $R^D$ is a subsituted or unsubstituted phenyl moiety; optionally substituted with one or more phosphorus-containing moieties, PCM, from Series I, Ia, Ib or Ic, and is optionally further substituted with one or more occurrences of $R^3$;
xvii) $R^D$ is a substituted or unsubstituted pyridinyl moiety; optionally substituted with one or more phosphorus-containing moieties, PCM, from Series I, Ia, Ib or Ic, and is optionally further substituted with one or more occurrences of $R^3$; wherein each occurrence of $R^3$ is independently hydrogen; halogen; —CN; NO$_2$; N$_3$; $R^1$; —GR$^1$; —CO(Y'R$^1$); —NR$^1$(Y'R$^1$); S(O)$_2$(Y'R$^1$); wherein each occurrence of Y' is independently —O—, —S—, —NR$^1$—, —C(O)—, —COO— or S(O)$_2$; wherein $R^1$ is independently a substituted or unsubstituted aliphatic, heteroaliphatic, aryl or heteroaryl moiety, or, except in YR$^1$ moieties in which Y is a covalent bond, $R^1$ may also be H; and each occurrence of G is independently absent, or is —O—, —S—, —NH—, —$NR^1$, $S(O)_2$, or $(M)_x$;

xix) each occurrence of $R^3$ is independently halogen, hydroxyl, amino, or is an aliphatic or heteroaliphatic moiety, wherein the aliphatic or heteroaliphatic moiety is substituted or unsubstituted, cyclic or acyclic, linear or branched;

xx) one or more occurrences of $R^3$ is lower alkyl, halo, or lower alkoxy;

xxi) r is 1 and $R^3$ is halogen;

xxii) r is 1 and $R^3$ is chlorine;

xxiii) r is 1 and $R^3$ is chlorine located at the ortho position;

xxiv) r is 1 and $R^3$ is chlorine located at the meta position;

xxv) either or both of $R^B$ and $R^D$ independently comprises or is substituted with a phosphorus-containing moiety of Series I, Ia, Ib, Ic, II, IIa, IIb or III;

xxvi)) both $R^B$ and $R^D$ independently comprise or are substituted with a phosphorus-containing moiety of Series I, Ia, Ib, Ic, II, IIa, IIb or III;

xxvii) $R^C$ is hydrogen or lower alkyl;

xxviii) $R_C$ is hydrogen;

xxix) $R^7$ is hydrogen, OH, alkoxy or $NH^2$;

xxx) $R^7$ is $NH_2$;

xxxi) $R^C$ is hydrogen and $R^7$ is $NH_2$;

xxxii) $R^{9a}$ is hydrogen or a $C_{1-6}$ alkyl or heteroalkyl moiety;

xxxiii) $R^{9a}$ is hydrogen or lower alkyl;

xxxiv) $R^{9a}$ is hydrogen, methyl or ethyl;

xxxv) $R^9$ is hydrogen, halogen or lower alkyl;

xxxvi) $R^5$ is hydrogen, halogen or lower alkyl;

xxxvii) $R^9$ and $R^5$ are each hydrogen;

xxxviii) q is 0;

xxxix) $R^B$ or $R^D$ (and substituents defined therein) independently comprises or is substituted with:

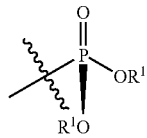

wherein each $R^1$ is independently H, alkyl, arylalkyl, aryl or a prodrug moiety;

xl) $R^B$ or $R^D$ (and substituents defined therein) independently comprises or is substituted with:

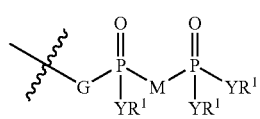

wherein each $R^1$ is independently H, alkyl, arylalkyl, aryl or a prodrug moiety;

xli) $R^B$ or $R^D$ (and substituents defined therein) independently comprises or is substituted with:

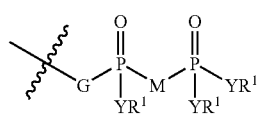

wherein each $R^1$ is independently H, alkyl, arylalkyl, aryl or a prodrug moiety; and M is —$CH_2$—, —CH(OH)—, —CH($NH_2$)—, —C(alkyl)(OH)—, —C(alkyl)($NH_2$)—, —CH(halo)— or —C(halo)$_2$—;

xlii) $R^B$ or $R^D$ (and substituents defined therein) independently comprises or is substituted with:

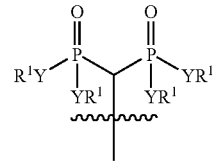

wherein each $R^1$ is independently H, alkyl, arylalkyl, aryl or a prodrug moiety;

xliii) $R^B$ or $R^D$ (and substituents defined therein) independently comprises or is substituted with:

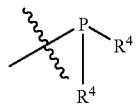

wherein each $R^4$ is independently alkyl, arylalkyl, aryl or a prodrug moiety;

xliv) $R^B$ or $R^D$ (and substituents defined therein) independently comprises or is substituted with:

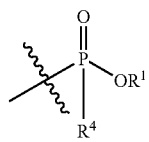

wherein $R^1$ is H, alkyl, arylalkyl or a prodrug moiety and $R^4$ is alkyl, arylalkyl, aryl or a prodrug moiety;

xlv) $R^B$ or $R^D$ (and substituents defined therein) independently comprises or is substituted with:

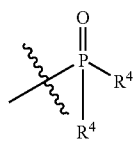

wherein each $R^4$ is independently alkyl, arylalkyl, aryl or a prodrug moiety;

xlvi) $R^B$ or $R^D$ (and substituents defined therein) independently comprises or is substituted with:

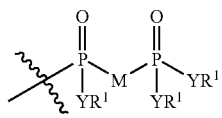

wherein each R¹ is independently H, alkyl, arylalkyl or a prodrug moiety, and Y and M are as defined previously;

xlvii) $R^B$ or $R^D$ (and substituents defined therein) independently comprises or is substituted with:

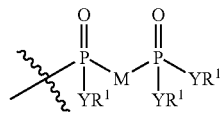

wherein each R¹ is independently H, alkyl, arylalkyl or a prodrug moiety, and Y is as defined previously; and M is —CH₂—, —CH(OH)—, —CH(NH₂)—, —C(alkyl)(OH)—, —C(alkyl)(NH₂)—, —CH(halo)— or —C(halo)₂—;

xlviii) $R^B$ or $R^D$ (and substituents defined therein) independently comprises or is substituted with:

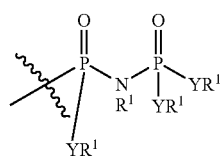

wherein each R¹ is independently H, alkyl, arylalkyl, aryl or a prodrug moiety;

xlix) $R^B$ or $R^D$ (and substituents defined therein) independently comprises or is substituted with:

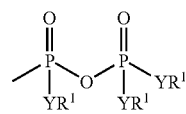

wherein each R¹ is independently H, alkyl, arylalkyl, aryl or a prodrug moiety, and Y is as defined previously;

l) $R^B$ or $R^D$ (and substituents defined therein) independently comprises or is substituted with:

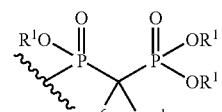

wherein each R¹ is independently H, alkyl, arylalkyl or a prodrug moiety, and R⁶ is hydrogen, lower alkyl, $OR^L$ or $NR^L R^M$; wherein each occurrence of $R^L$ and $R^M$ is independently hydrogen, or an alkyl, heteroalkyl, aryl or heteroaryl moiety;

li) $R^B$ or $R^D$ (and substituents defined therein) independently comprises or is substituted with:

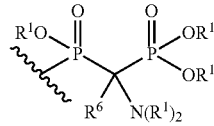

wherein each R¹ is independently H, alkyl, arylalkyl or a prodrug moiety, and R⁶ is hydrogen, lower alkyl, $OR^L$ or $NR^L R^M$; wherein each occurrence of $R^L$ and $R^M$ is independently hydrogen, or an alkyl, heteroalkyl, aryl or heteroaryl moiety;

lii) $R^B$ or $R^D$ (and substituents defined therein) independently comprises or is substituted with:

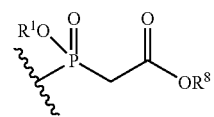

wherein R¹ is H, alkyl, arylalkyl or a prodrug moiety, and R⁶ is as previously defined;

liii) $R^B$ or $R^D$ (and substituents defined therein) independently comprises or is substituted with:

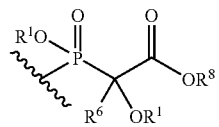

wherein each R¹ is independently H, alkyl, arylalkyl or a prodrug moiety, R⁶ is as previously defined, and R⁸ is hydrogen, lower alkyl, lower heteroalkyl, aryl, heteroaryl or a prodrug moiety;

liv) $R^B$ or $R^D$ (and substituents defined therein) independently comprises or is substituted with:

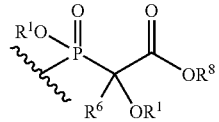

wherein each R¹ is independently H, alkyl, arylalkyl or a prodrug moiety, and R⁶ and R⁸ are as previously defined;

lv) $R^B$ or $R^D$ (and substituents defined therein) independently comprises or is substituted with:

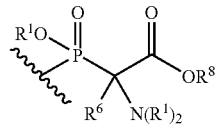

wherein each occurrence of R¹ is independently H, alkyl, arylalkyl or a prodrug moiety, and R⁶ and R⁸ are previously defined;

lvi) if q is 0; and $R^B$ comprises the only phosphorus-containing moiety PCM and PCM is —P(=O)OR'R", or if $R^{9a}$ is —$C_{1-6}$alkylP(=O)OR'OR"; wherein R' and R" are independently hydrogen, $C_{1-6}$alkyl, —$(CR_xR_y)_\omega$—$C_{3-10}$cycloalkyl or aryl$C_{1-6}$alkyl; wherein w is an integer from 0–5 and $R_x$ and $R_y$ are independently hydrogen or $C_{1-6}$alkyl; then $R^B$ is not phenyl; and lvii) if q is 0; and $R^B$ and $R^D$ are each phenyl, then neither $R^B$ nor $R^D$ is substituted with —P(=O)OR'R"; and $R^{9a}$ is not —$C_{1-6}$alkylP(=O)OR'OR"; wherein R' and R" are independently hydrogen, $C_{1-6}$alkyl, —$(CR_xR_y)_\omega$—$C_{3-10}$cycloalkyl or aryl$C_{1-6}$alkyl; wherein w is an integer from 0–5 and $R_x$ and $R_y$ are independently hydrogen or $C_{1-6}$alkyl.

As the reader will appreciate, compounds of particular interest include, among others, those that share the attributes of one or more of the foregoing subclasses.

Some of those subclasses are illustrated by the following sorts of compounds:

I. Compounds of the Formula (and Pharmaceutically Acceptable Derivatives Thereof):

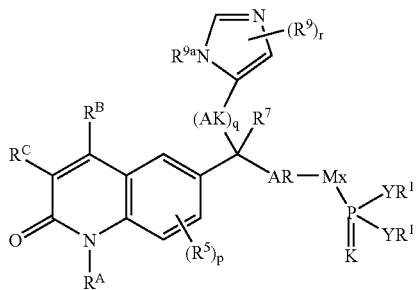

wherein AR is an aryl or heteroaryl moiety;

$R^A$ is hydrogen, oxygen, or an alkyl or heteroalkyl moiety;

$R^B$ is an alkyl, heteroalkyl, aryl or heteroaryl moiety;

$R^C$ is hydrogen; halogen, cyano or an alkyl or heteroalkyl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —$NR^L R^M$, or an alkyl, heteroalkyl, aryl or heteroaryl moiety;

AK is $(CR^PCR^Q)$;

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently —O—, —S—, $NR^1$—, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and $R^B$ optionally additionally comprises or is substituted with a phosphorus-containing moiety.

In certain embodiments, $R^B$ is an aryl or heteroaryl moiety substituted independently with one or more occurrences of hydrogen, halogen, cyano, hydroxy, or alkoxy. In certain other embodiments each occurrence of $R^9$ and $R^5$ are each hydrogen. In still other embodiments $R^7$ is $NH_2$ or N(alkyl)$_2$. In still other exemplary embodiments $R^A$ is hydrogen or methyl. In yet other embodiments of interest $R^{9a}$ is hydrogen, methyl or ethyl. In certain other embodiments, q is 0.

II. Compounds of the Formula (and Pharmaceutically Acceptable Derivatives Thereof):

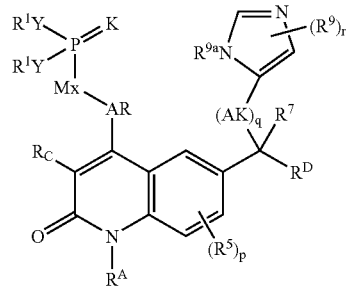

wherein AR is an aryl or heteroaryl moiety;

$R^A$ is hydrogen, oxygen, or an alkyl or heteroalkyl moiety;

$R^C$ is hydrogen; halogen, cyano or an alkyl or heteroalkyl moiety;

$R^D$ is an alkyl, heteroalkyl, aryl or heteroaryl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, —$NR^L R^M$, or an alkyl, heteroalkyl, aryl or heteroaryl moiety;

AK is $(CR^PCR^Q)$;

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently —O—, —S—, $NR^1$—, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and $R^D$ optionally additionally comprises or is substituted with a phosphorus-containing moiety.

In certain embodiments, $R^D$ is an aryl or heteroaryl moiety substituted independently with one or more occurrences of hydrogen, halogen, cyano, hydroxy, or alkoxy. In certain other embodiments each occurrence of $R^9$ and $R^5$ are each hydrogen. In still other embodiments $R^7$ is $NH_2$ or $N(alkyl)_2$. In still other exemplary embodiments $R^A$ is hydrogen or methyl. In yet other embodiments of interest $R^{9a}$ is hydrogen, methyl or ethyl. In certain other embodiments, q is 0.

III. Compounds of the Formula (and Pharmaceutically Acceptable Derivatives Thereof):

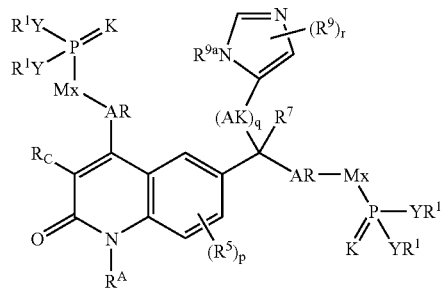

wherein each occurrence of AR is independently an aryl or heteroaryl moiety;

$R^A$ is hydrogen, oxygen, or an alkyl or heteroalkyl moiety;

$R^C$ is hydrogen; halogen, cyano or an alkyl or heteroalkyl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or $-ZR^J$, wherein each occurrence of Z is independently $-O-$, $-S-$, $NR^K$, $-C(O)-$, $-S(O)_2-$, or $COO-$, wherein each occurrence of $R^J$ and $R^K$ is independently hydrogen, $COR^L$, $COOR^L$, $CONR^LR^M$, $NR^LR^M$, or an alkyl, heteroalkyl, aryl or heteroaryl moiety;

AK is $(CR^PCR^Q)$;

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently $-O-$, $-S-$, $NR^1-$, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

In certain embodiments, $R^9$ and $R^5$ are each hydrogen. In still other embodiments $R^7$ is $NH_2$ or $N(alkyl)_2$. In still other exemplary embodiments $R^A$ is hydrogen or methyl. In yet other embodiments of interest $R^{9a}$ is hydrogen, methyl or ethyl. In certain other embodiments, q is 0.

IV. Compounds of the Formula (and Pharmaceutically Acceptable Derivatives Thereof):

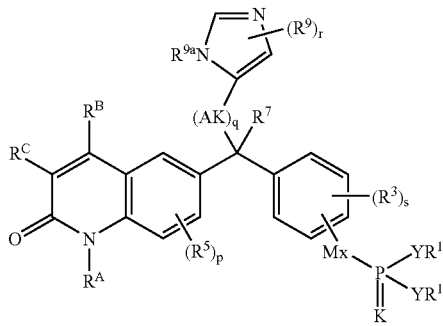

wherein $R^A$ is hydrogen, oxygen, or an alkyl or heteroalkyl moiety;

$R^B$ is an alkyl, heteroalkyl, aryl or heteroaryl moiety;

$R^C$ is hydrogen; halogen, cyano or an alkyl or heteroalkyl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or $-ZR^J$, wherein each occurrence of Z is independently $-O-$, $-S-$, $NR^K$, $-C(O)-$, $-S(O)_2-$, or $-COO-$, wherein each occurrence of $R^J$ and $R^K$ is independently hydrogen, $COR^L$, $COOR^L$, $CONR^LR^M$, $-NR^LR^M$, or an alkyl, heteroalkyl, aryl or heteroaryl moiety;

AK is $(CR^PCR^Q)$;

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently $-O-$, $-S-$, $NR^1-$, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and $R^B$ optionally additionally comprises or is substituted with a phosphorus-containing moiety.

In certain embodiments, $R^B$ is an aryl or heteroaryl moiety substituted independently with one or more occurrences of hydrogen, halogen, cyano, hydroxy, or alkoxy. In certain other embodiments each occurrence of $R^9$ and $R^5$ are each hydrogen. In still other embodiments $R^7$ is $NH_2$ or $N(alkyl)_2$.

In still other exemplary embodiments $R^A$ is hydrogen or methyl. In yet other embodiments of interest $R^{9a}$ is hydrogen, methyl or ethyl. In certain other embodiments, q is 0.

V Compounds of the Formula (and Pharmaceutically Acceptable Derivatives Thereof):

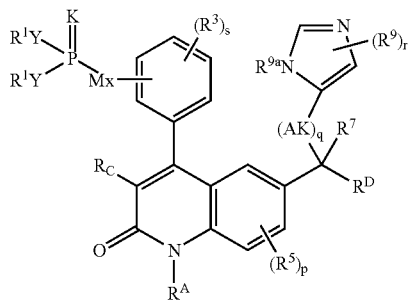

wherein $R^A$ is hydrogen, oxygen, or an alkyl or heteroalkyl moiety;

$R^C$ is hydrogen; halogen, cyano or an alkyl or heteroalkyl moiety;

$R^D$ is an alkyl, heteroalkyl, aryl or heteroaryl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, $NR^LR^M$, or an alkyl, heteroalkyl, aryl or heteroaryl moiety;

AK is ($CR^PCR^Q$);

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently —O—, —S—, $NR^1$—, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted; and $R^D$ optionally additionally comprises or is substituted with a phosphorus-containing moiety.

In certain embodiments, $R^D$ is an aryl or heteroaryl moiety substituted independently with one or more occurrences of hydrogen, halogen, cyano, hydroxy, or alkoxy. In certain other embodiments each occurrence of $R^9$ and $R^5$ are each hydrogen. In still other embodiments $R^7$ is $NH_2$ or $N(alkyl)_2$. In still other exemplary embodiments $R^A$ is hydrogen or methyl. In yet other embodiments of interest $R^{9a}$ is hydrogen, methyl or ethyl. In certain other embodiments, q is 0.

VI. Compounds of the Formula (and Pharmaceutically Acceptable Derivatives Thereof):

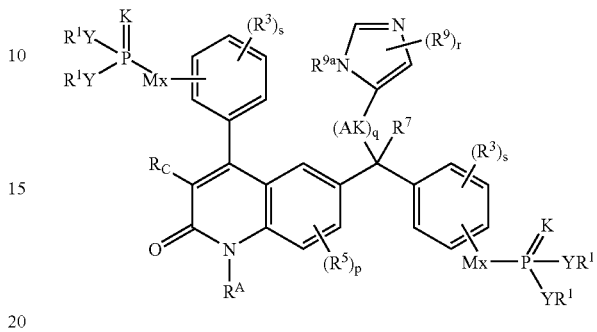

wherein $R^A$ is hydrogen, oxygen, or an alkyl or heteroalkyl moiety;

$R^C$ is hydrogen; halogen, cyano or an alkyl or heteroalkyl moiety;

each occurrence of $R^9$ and $R^5$ is independently hydrogen, halogen, alkyl or heteroalkyl;

$R^7$ is hydrogen; alkyl; heteroalkyl; aryl; heteroaryl; cyano; or —$ZR^J$, wherein each occurrence of Z is independently —O—, —S—, $NR^K$, —C(O)—, —S(O)$_2$—, or —COO—, wherein each occurrence of $R^J$ and $R^K$ is independently hydrogen, $COR^L$, $COOR^L$, $CONR^LR^M$, $NR^LR^M$, or an alkyl, heteroalkyl, aryl or heteroaryl moiety;

AK is ($CR^PCR^Q$);

each occurrence of $R^P$ and $R^Q$ is independently hydrogen or an alkyl or heteroalkyl moiety;

q is an integer from 0 to 5;

p is an integer from 0–3;

r is an integer from 0–2;

$R^{9a}$ is hydrogen; or an alkyl or heteroalkyl moiety;

K is O or S;

each occurrence of Y is independently —O—, —S—, $NR^1$—, or a chemical bond linking $R^1$ to P, each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is 0–6;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

In certain embodiments, $R^9$ and $R^5$ are each hydrogen. In still other embodiments $R^7$ is $NH_2$ or $N(alkyl)_2$. In still other exemplary embodiments $R^A$ is hydrogen or methyl. In yet other embodiments of interest $R^{9a}$ is hydrogen, methyl or ethyl. In certain other embodiments, q is 0.

VII. Compounds of the Formula (and Pharmaceutically Acceptable Derivatives Thereof):

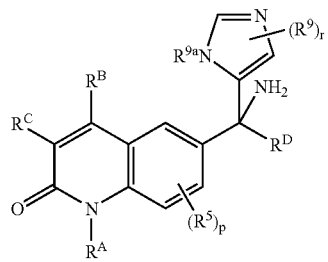

wherein $R^A$ is hydrogen, oxygen, or an alkyl or heteroalkyl moiety;

$R^B$ is an alkyl, heteroalkyl, aryl or heteroaryl moiety;

$R^C$ is hydrogen; halogen, cyano or an alkyl or heteroalkyl moiety;

each occurrence of $R^9$ and $R^5$ is independently hydrogen, halogen, alkyl or heteroalkyl;

p is an integer from 0–3;

r is an integer from 0–2;

$R^{9a}$ is hydrogen; or an alkyl or heteroalkyl moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted;

and wherein either one or both of $R^B$ and $R^D$ comprises or is substituted with a phosphorus-containing moiety of Series II:

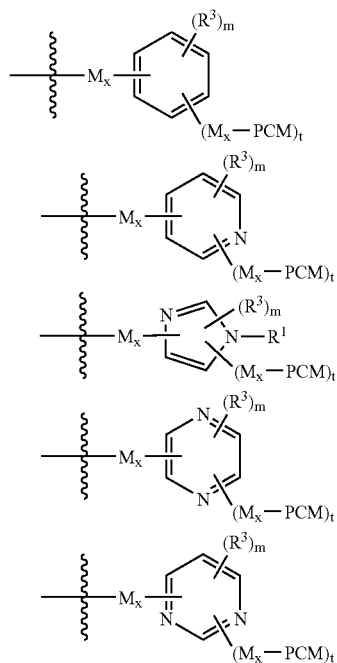

Series II wherein each occurrence of $R^3$ is independently hydrogen; halogen; —CN; $NO_2$; $N_3$; $R^1$; —$GR^1$; —CO(Y'$R^1$); —$NR^1$(Y'$R^1$); $S(O)_2$(Y'$R^1$); wherein each occurrence of Y' is independently —O—, —S—, —$NR^1$—, —C(O)—, —COO— or $S(O)_2$; and each occurrence of G is independently absent, or is —O—, —S—, —$NR^1$, $S(O)_2$, or $(M)_x$;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

PCM is a phosphorus-containing moiety of Series 1, Series Ia, Series Ib; or Series Ic, and m is an integer from 0–3, t is an integer from 1–3, and the sum of m+t is an integer from 1–5.

In certain embodiments, either one or both of $R^B$ and $R^D$ is independently substituted with one or more occurrences of hydrogen, halogen, cyano, hydroxy, or alkoxy. In certain other embodiments each occurrence of $R^9$ and $R^5$ are each hydrogen. In still other exemplary embodiments $R^A$ is hydrogen or methyl. In yet other embodiments of interest $R^{9a}$ is hydrogen, methyl or ethyl.

VIII. Compounds of the Formula (and Pharmaceutically Acceptable Derivatives Thereof):

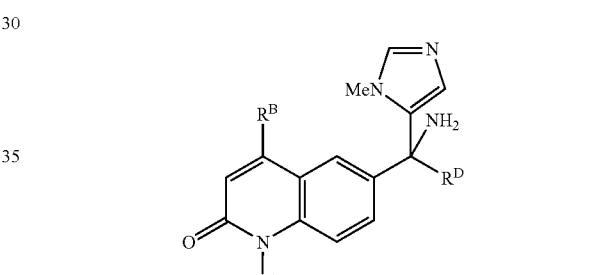

wherein $R^A$ is hydrogen, oxygen or an aliphatic or heteroaliphatic moiety;

$R^B$ is an aryl, heteroaryl, alkylaryl, or alkylheteroaryl moiety;

$R^D$ is an aryl, heteroaryl, alkylaryl, or alkylheteroaryl moiety;

wherein in each of the foregoing groups each aliphatic, heteroaliphatic, alkylaryl, or alkylheteroaryl moiety may be branched or unbranched, cyclic or acyclic and substituted or unsubstituted, and may contain one or more electronically unsaturated bonds, and each aryl and heteroaryl moiety may be substituted or unsubstituted;

and wherein either one or both of $R^B$ and $R^D$ comprises or is substituted with a phosphorus containing moiety of Series II:

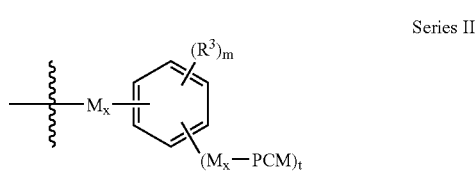

Series II

-continued

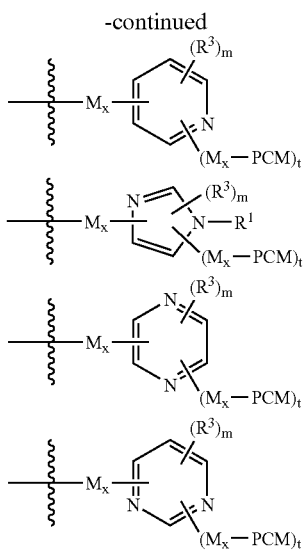

wherein each occurrence of R³ is independently hydrogen; halogen; —CN; NO₂; N₃; R¹; —GR¹; —CO(Y'R¹); —NR¹(Y'R¹); S(O)₂(Y'R¹); wherein each occurrence of Y' is independently —O—, —S—, —NR¹—, —C(O)—, —COO— or S(O)₂; and each occurrence of G is independently absent, or is —O—, —S—, —NR¹—, S(O)₂, or (M)ₓ;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of M is independently a substituted or unsubstituted methylene moiety, and any M-M' moiety may be electronically saturated or unsaturated;

each occurrence of x is independently an integer from 0–6;

PCM is a phosphorus-containing moiety of Series I, Series Ia, Series Ib; or Series Ic, and m is an integer from 0–3, t is an integer from 1–3, and the sum of m+t is an integer from 1–5.

In certain embodiments, either one or both of R^B and R^D is independently substituted with one or more occurrences of hydrogen, halogen, cyano, hydroxy, or alkoxy. In certain other embodiments each occurrence of R⁹ and R⁵ are each hydrogen. In still other exemplary embodiments R^A is hydrogen or methyl. In yet other embodiments of interest R^{9a} is hydrogen, methyl or ethyl.

IX. Compounds of the Formula (and Pharmaceutically Acceptable Derivatives Thereof):

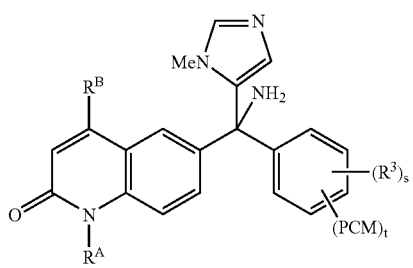

wherein R^A is an aliphatic or heteroaliphatic moiety;

R^B is an aryl, heteroaryl, alkylaryl, or alkylheteroaryl moiety;

R³ independently represents from 0–3 substituents selected from hydrogen; halogen; R¹; —GR¹; —CO(Y'R¹); acylamino, amido, amidino, cyano, nitro, azido, sulfonyl, sulfoxido, sulfate, sulfonate, sulfamoyl, and sulfonamido; wherein each occurrence of Y' is independently —O—, —S—, —NR¹—, —C(O)—, —COO— or S(O)₂;

t is an integer from 1–3;

s is an integer from 0–4; wherein the sum t+s is 1–5; and wherein PCM is a phosphorus-containing moiety selected from Series I:

Series I

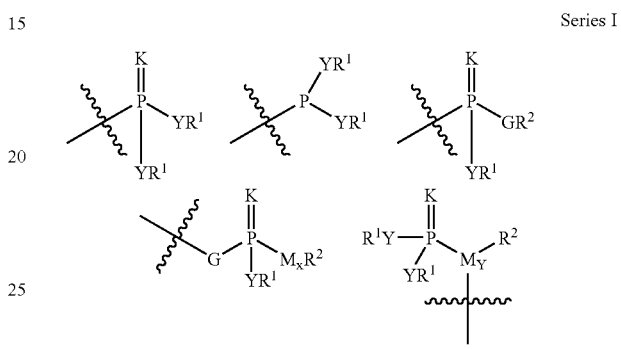

wherein each occurrence of K is independently O or S;

each occurrence of Y is independently —O—, —S—, —NH—, —NR¹—, or a chemical bond linking R¹ to P;

each occurrence of R¹ is independently a substituted or unsubstituted aliphatic, heteroaliphatic, aryl or heteroaryl moiety, or, except in YR¹ moieties in which Y is a covalent bond, R¹ may also be H;

each occurrence of R² is independently R¹, —PK(YR¹)(YR¹), —SO₂(YR¹) or —C(O)(YR¹);

each occurrence of G is independently absent, or is —O—, —S—, —NR¹— or (M)ₓ;

each occurrence of M is independently a substituted or unsubstituted methylene moiety, and any M-M' moiety may be electronically saturated or unsaturated;

each occurrence of x is independently an integer from 0–6; and each occurrence of M_Y is independently a methine group or a lower alkyl moiety which contains a methine group and optionally may be further substituted.

X. Compounds of the Formula (and Pharmaceutically Acceptable Derivatives Thereof):

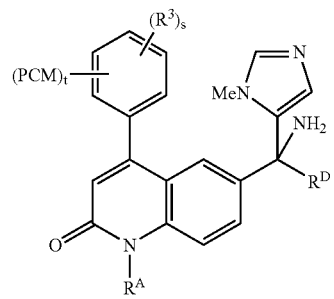

wherein R^A is an aliphatic or heteroaliphatic moiety;

R^D is an aryl, heteroaryl, alkylaryl, or alkylheteroaryl moiety;

$R^3$ independently represents from 0–3 substituents selected from hydrogen; halogen; $R^1$; —$GR^1$; —$CO(Y'R^1)$; acylamino, amido, amidino, cyano, nitro, azido, sulfonyl, sulfoxido, sulfate, sulfonate, sulfamoyl, and sulfonamido; wherein each occurrence of Y' is independently —O—, —S—, —$NR^1$—, —C(O)—, —COO— or $S(O)_2$;

t is an integer from 1–3;

s is an integer from 0–3, wherein the sum t+s is 1–5; and wherein PCM is a phosphorus-containing moiety selected from Series I:

Series I

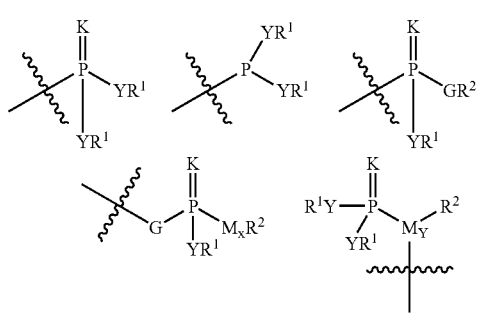

wherein each occurrence of K is independently O or S;

each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —$PK(YR^1)(YR^1)$, —$SO_2(YR^1)$ or —$C(O)(YR^1)$;

each occurrence of G is independently absent, or is —O—, —S—, —$NR^1$— or $(M)_x$;

each occurrence of M is independently a substituted or unsubstituted methylene moiety, and any M-M' moiety may be electronically saturated or unsaturated;

each occurrence of x is independently an integer from 0–6; and each occurrence of $M_Y$ is independently a methine group or a lower alkyl moiety which contains a methine group and optionally may be further substituted.

It will be appreciated that, in certain exemplary embodiments, for each of the foregoing compounds described in sections VII–X above, either or both of $R^B$ and $R^D$ (or specific substituents as further defined for $R^B$ and $R^D$, e.g., AR, phenyl) independently comprises or is substituted with a phosphorus-containing moiety of Series IIa:

Series IIa

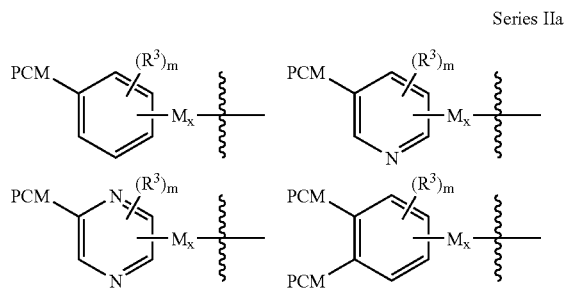

-continued

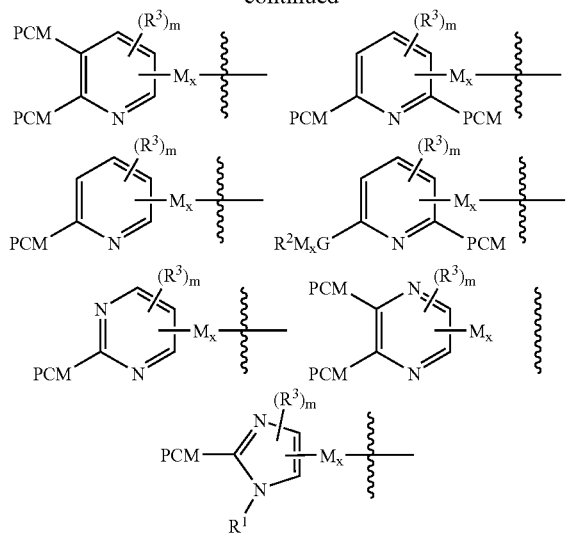

wherein each occurrence of $R^3$ is independently hydrogen; halogen; —CN; $NO_2$; $N_3$; $R^1$; —$GR^1$; —$CO(Y'R^1)$; —$NR^1(Y'R^1)$; $S(O)_2(Y'R^1)$; wherein each occurrence of Y' is independently —O—, —S—, —$NR^1$—, —C(O)—, —COO— or $S(O)_2$;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of $R^2$ is independently $R^1$, —$PK(YR^1)(YR^1)$, —$SO_2(YR^1)$ or —$C(O)(YR^1)$; wherein each occurrence of Y is independently —O—, —S—, —NH—, —$NR^1$—, or a chemical bond linking $R^1$ to P;

each occurrence of G is independently absent, or is —O—, —S—, —$NR^1$—, $S(O)_2$, or $(M)_x$;

each occurrence of M is independently a substituted or unsubstituted methylene moiety, and any M-M' moiety may be electronically saturated or unsaturated;

each occurrence of x is independently an integer from 0–6;

m is an integer from 0–3; and

PCM is a phosphorus-containing moiety of Series I, Series Ia, Series Ib or Series Ic.

In certain other exemplary embodiments, PCM is a phosphorus-containing moiety of Series Ic Series Ic

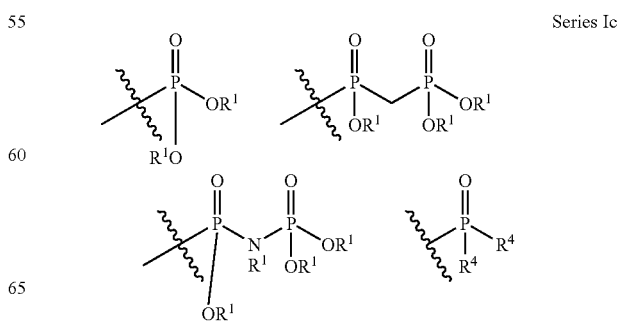

-continued

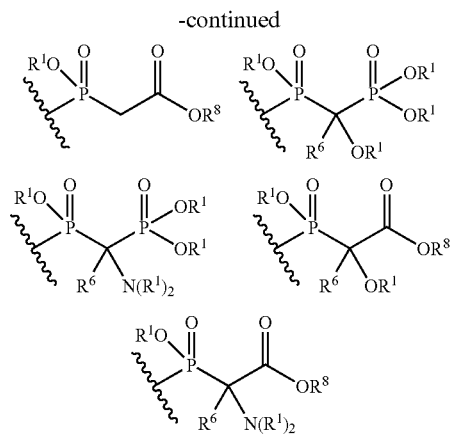

wherein each occurrence of $R^1$ is independently hydrogen, alkyl or aryl;

each occurrence of $R^4$ is independently alkyl or aryl;

each occurrence of $R^6$ is independently hydrogen, alkyl, heteroalkyl, aryl or heteroaryl; and each occurrence of $R^8$ is independently hydrogen, alkyl, heteroalkyl, aryl or heteroaryl, or a prodrug moiety.

In certain other embodiments, $R^6$ is hydrogen, lower alkyl, $OR^L$ or $NR^L R^M$; wherein each occurrence of $R^L$ and $R^M$ is independently hydrogen, or an alkyl, heteroalkyl, aryl or heteroaryl moiety. In certain other embodiments, $R^6$ is hydrogen, methyl, ethyl, OH or $NH_2$. In certain embodiments, $R^8$ is hydrogen, lower alkyl, lower heteroalkyl, aryl, heteroaryl or a prodrug moiety. In still other embodiments, $R^8$ is hydrogen, methyl, ethyl, or a prodrug moiety.

In certain other exemplary embodiments, for each of the foregoing compounds described in sections VII–X above, either or both of $R^B$ and $R^D$ (or specific substituents as further defined for $R^B$ and $R^D$, e.g., AR, phenyl) independently comprises or is substituted with a phosphorus-containing moiety of Series IIb:

Series IIb

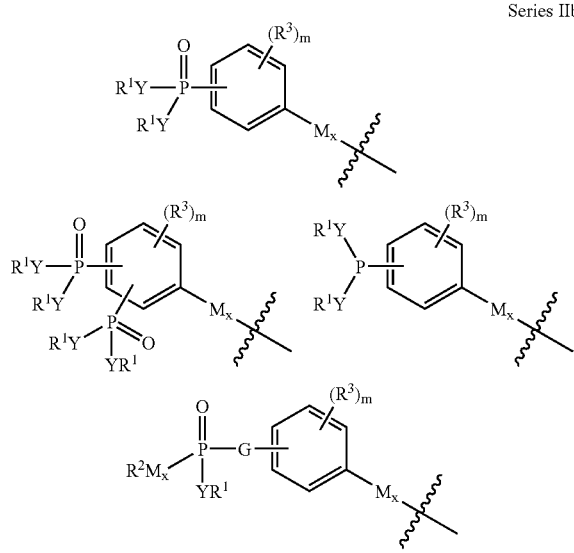

wherein each occurrence of $R^3$ is independently hydrogen; halogen; —CN; $NO_2$; $N_3$; $R^1$; —$GR^1$; —CO(Y'R$^1$); —NR$^1$(Y'R$^1$); S(O)$_2$(Y'R$^1$); wherein each occurrence of Y' is independently —O—, —S—, —NR$^1$—, —C(O)—, —COO— or S(O)$_2$;

each occurrence of $R^2$ is independently $R^1$, —PK(YR$^1$)(YR$^1$), —SO$_2$(YR$^1$) or —C(O)(YR$^1$);

each occurrence of Y is independently —O—, —S—, —NH—, —NR$^1$—, or a chemical bond linking $R^1$ to P;

each occurrence of $R^1$ is independently a substituted or unsubstituted aliphatic, heteroaliphatic, aryl or heteroaryl moiety, or, except in YR$^1$ moieties in which Y is a covalent bond, $R^1$ may also be H;

each occurrence of G is independently absent, or is —O—, —S—, —NR$^1$—, S(O)$_2$, or (M)$_x$;

each occurrence of $M_Y$ is independently a methine group or a lower alkyl moiety which contains a methine group and optionally may be further substituted;

each occurrence of M is independently a substituted or unsubstituted methylene moiety, and any M-M' moiety may be electronically saturated or unsaturated;

each occurrence of x is independently an integer from 0–6; and m is an integer from 0–3.

In still other exemplary embodiments, for each of the foregoing compounds described in sections VII–X above, either or both of $R^B$ and $R^D$ (or specific substituents as further defined for $R^B$ and $R^D$, e.g., AR, phenyl) independently comprises or is substituted with a phosphorus-containing moiety of Series III.

Series III

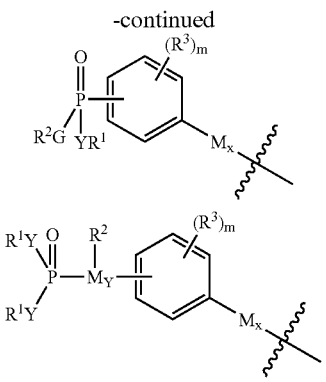

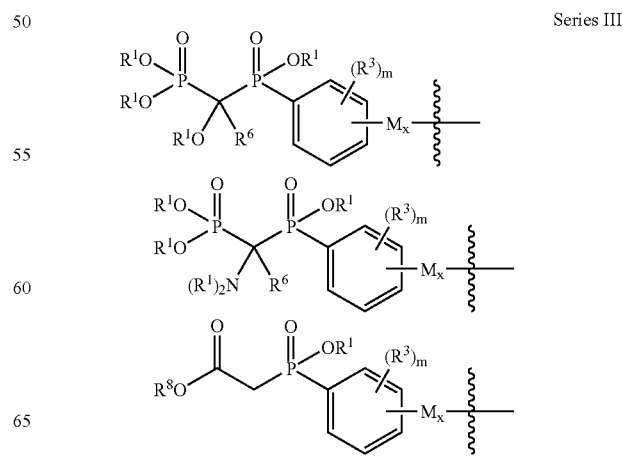

-continued

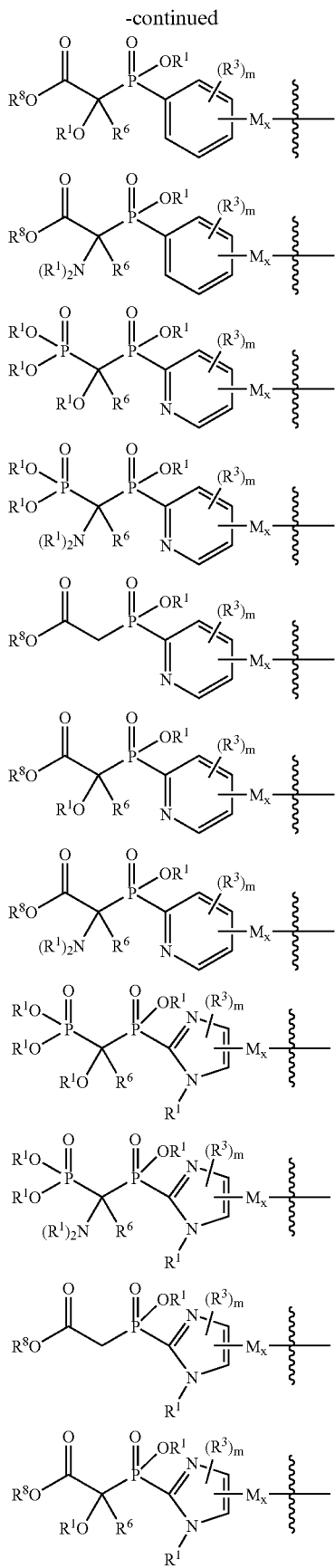

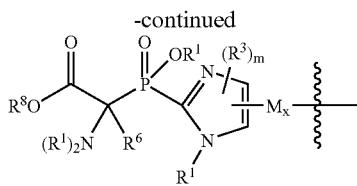

wherein each occurrence of $R^3$ is independently hydrogen; halogen; —CN; $NO_2$; $N_3$; $R^1$; —$GR^1$; —$CO(Y'R^1)$; —$NR(Y'R^1)$; $S(O)_2(Y'R^1)$; wherein each occurrence of Y' is independently —O—, —S—, —$NR^1$—, —C(O)—, —COO— or $S(O)_2$; each occurrence of G is independently absent, or is —O—, —S—, —$NR^1$—, $S(O)_2$, or $(M)_x$; and m is an integer from 0–4;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

each occurrence of x is independently an integer from 0–6;

each occurrence of $R^6$ is independently hydrogen, aliphatic, heteroaliphatic, aryl or heteroaryl moiety; and each occurrence of $R^8$ is independently hydrogen, an aliphatic, heteroaliphatic, aryl or heteroaryl moiety, or a prodrug moiety;

wherein in each of the foregoing groups each aliphatic or heteroaliphatic moiety may be branched or unbranched, cyclic or acyclic and substituted or unsubstituted, and may contain one or more electronically unsaturated bonds, and each aryl and heteroaryl moiety may be substituted or unsubstituted.

XI. Compounds of the Formula (and Pharmaceutically Acceptable Derivatives Thereof):

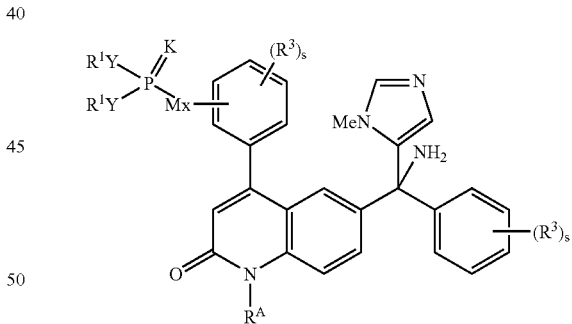

wherein $R^A$ is an aliphatic or heteroaliphatic moiety;

each occurrence of K is independently O or S;

each occurrence of Y is independently —O—, —S—, —NH—, —$NR^1$—, or a chemical bond linking $R^1$ to P;

each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H;

each occurrence of M is independently a substituted or unsubstituted methylene moiety, and any M-M' moiety may be electronically saturated or unsaturated;

x is an integer from 0–6;

each occurrence of $R^3$ independently represents hydrogen; halogen; $C_{1-6}$ alkyl; and $C_{1-6}$ alkyloxy;

each occurrence of s is independently an integer from 0–3; and wherein in each of the foregoing groups each aliphatic, heteroaliphatic, alkylaryl, or alkylheteroaryl moiety may be branched or unbranched, cyclic or acyclic and substituted or unsubstituted, and may contain one or more electronically unsaturated bonds, and each aryl and heteroaryl moiety may be substituted or unsubstituted.

XII. Compounds of the Formula (and Pharmaceutically Acceptable Derivatives Thereof):

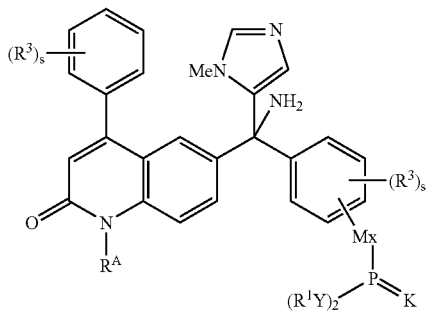

wherein $R^A$ is an aliphatic or heteroaliphatic moiety;

each occurrence of K is independently O or S;

each occurrence of Y is independently —O—, —S—, —NH—, —NR$^1$—, or a chemical bond linking R$^1$ to P;

each occurrence of R$^1$ is independently a substituted or unsubstituted aliphatic, heteroaliphatic, aryl or heteroaryl moiety, or, except in YR$^1$ moieties in which Y is a covalent bond, R$^1$ may also be H;

each occurrence of M is independently a substituted or unsubstituted methylene moiety, and any M-M' moiety may be electronically saturated or unsaturated;

x is an integer from 0–6;

each occurrence of R$^3$ independently represents hydrogen; halogen; $C_{1-6}$ alkyl; and $C_{1-6}$ alkyloxy;

each occurrence of s is independently an integer from 0–3; and wherein in each of the foregoing groups each aliphatic, heteroaliphatic, alkylaryl, or alkylheteroaryl moiety may be branched or unbranched, cyclic or acyclic and substituted or unsubstituted, and may contain one or more electronically unsaturated bonds, and each aryl and heteroaryl moiety may be substituted or unsubstituted.

In certain embodiments, for each of the compounds as described above and herein, Y is a chemical bond linking the phosphorus atom to R$^1$. In certain other embodiments Y is an oxygen atom. In still other embodiments, Y is a chemical bond linking the phosphorus atom to R$^1$ and R$^1$ is an alkyl group having 1–6 carbon atoms. In yet other embodiments of the compounds as generally described above, R$^A$ is hydrogen or an aliphatic or heteroaliphatic moiety. In certain other subsets, K is O. In still other embodiments, x is 0. In yet other embodiments, x is 1–4 and M is —CH$_2$—.

This invention also provides a pharmaceutical preparation comprising at least one of the foregoing compounds or a pharmaceutically acceptable derivative thereof, as inhibitors of bone resorption by osteoclasts, as inhibitors of tumor growth and tumor metastatsis, for the treatment and prophylaxis of diseases or undesirable conditions which are mediated by a kinase inhibited by said compound, as inhibitors of vascular permeability and/or angiogenesis, and at least one pharmaceutically acceptable excipient or additive. Preferably the excipient of additive is pharmaceutically innocuous.

The invention further provides a method for inhibiting bone resorption, inhibiting tumor growth and/or tumor metastasis, inhibiting vascular permeability and/or angiogenesis, or for the treatment and prevention of diseases or undesirable conditions which are mediated by a kinase inhibited by one of the foregoing compounds. The method involves administering a therapeutically effective amount of the compound or a pharmaceutically acceptable derivative thereof to a human or animal in need of it. Such administration constitutes a method for inhibiting bone resorption by osteoclasts, for inhibiting tumor growth and/or tumor metastasis or other proliferative disease, or for inhibiting vascular permeability and/or angiogenesis. Generally speaking, such administration comprises a method for the treatment and prophylaxis of diseases which are mediated by a kinase inhibited by one of the foregoing compounds or a pharamceutically acceptable derivative thereof.

The compounds provided by this invention are also useful as standards and reagents in characterization of various kinases, especially, but not limited to Src family kinases; the study of the role of such kinases in biological and pathological phenomena; the study of intracellular signal transduction pathways mediated by such kinases; the comparative evaluation of new kinase inhibitors; the study of various cancers in cell lines and animal models; and the study of bone biology, including the competing forces of resorption and generation of bone.

3. Compounds and Definitions

This invention provides a new family of compounds with a range of biological properties. Compounds of this invention have biological activities relevant for the treatment of diseases including bone related disorders, disorders related to cellular proliferation (e.g., cancer) and disorders related to increased vascular permeability and/or angiogenesis. More generally, the compounds are useful in the regulation of signal transduction pathways. For example, certain compounds of the invention are useful for inhibiting tyrosine kinases, including without limitation receptor-type tyrosine kinases such as those of the HER (e.g. EGFR, HER2, HER3 and HER4), PDGF and FLK families (including, e.g., VEGF-R1 and VEGF-R2) as well as non-receptor-type tyrosine kinases such as those of the Src and abl subfamilies, again as non-limiting examples.

Compounds of this invention include those described herein, and illustrated in part by the various classes, subclasses and species disclosed elsewhere herein.

Some of the compounds contain one or more asymmetric centers. Thus, compounds of the invention and pharmaceutical compositions thereof may be in the form of an individual enantiomer or diastereomer isomer, or may be in the form of a mixture of stereoisomers. In certain embodiments, the compounds of the invention are in the form of a single enantiomer or diastereomer, substantially free from other enantiomers or diastereomers (i.e., in a form containing less than 10%, preferably less than 5% and in some cases even more preferably less than 1% of one or more other enantiomers or diastereomers, by weight or molarity. In certain other embodiments, a mixture of stereoisomers or diastereomers are provided.

Additionally, the present invention provides pharmaceutically acceptable derivatives of the inventive compounds, and methods of treating a subject using these compounds, pharmaceutical compositions containing one or more of the compounds or a pharmaceutically acceptable derivative thereof, or either of these in combination with one or more additional therapeutic agents. The phrase, "pharmaceutically acceptable derivative", as used herein, denotes any pharmaceutically acceptable salt, ester, or salt of such ester, or salt of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of this invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, can utilize a variety of protecting groups. By the term "protecting group", has used herein, it is meant that a particular functional group, e.g., —OH, —NH—, —SH, —CHO, —COOH, —C=O—, —P(=O)(OH)—, etc., is temporarily blocked so that a reaction can be carried out selectively at another reactive site in a multifunctional compound. In preferred cases, a protecting group reacts selectively in good yield to give a protected substrate that is stable to the projected reactions; is selectively removable in practicable yield without loss of other functional groups of the protected molecule; forms a separable derivative (more preferably without the generation of new stereogenic centers); and has a minimum of additional functionality to avoid further sites of reaction. Exemplary protecting groups are detailed herein, however, it will be appreciated that the present invention is not limited to these protecting groups; rather, a variety of alternative protecting groups can be readily identified based on the above criteria combined with availability, user familiarity, convenience, etc. and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As described herein, compounds of the invention may be substituted with any number of substituents or functional groups, such as are illustrated in connection with particular classes, subclasses and species of the invention. In general, the term "substituted" and "substituent", whether preceded by the term "optionally" or not, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" encompasses all permissible substituents of organic compounds. Substituents are discussed in detail below and illustrated throughout this document. Combinations of substituents and variables envisioned by this invention are preferably those that result in the formation of stable compounds, useful in the treatment of various disorders as described herein, e.g. for bone related disorders, cancer or other disorders related to excessive cellular proliferation, disorders related to increases in vascular permeability, and/or more generally, disorders related to cell signalling. The term "stable", as used herein, refers to compounds that possess stability sufficient to allow their production, detection and preferably their recovery, purification and use for one or more of the purposes disclosed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. The term includes, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. The term "lower" as applied to alkyl or other aliphatic groups indicates a group having 1–6 carbon atoms (which may be substituted or unsubstituted as specified).

Unless otherwise specified, the alkyl, alkenyl and alkynyl groups contain 1–20 aliphatic carbon atoms. In some embodiments, they contain 1–10 aliphatic carbon atoms. In other embodiments, they contain 1–8 aliphatic carbon atoms. In still other embodiments, they contain 1–6 aliphatic carbon atoms, and in yet other embodiments, 1–4 carbon atoms. Illustrative aliphatic groups thus include, but are not limited to, for example, methyl, ethyl, allyl, n-propyl, iso-propyl, cyclopropyl, —$CH_2$-cyclopropyl, methallyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Benzyl, phenethyl, heteroaromatic analogs, and substituted derivatives of such moieties are thus considered substituted aliphatic moieties. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$–$C_3$ alkylamino groups are utilized in the present invention.

Some examples of substituents for various optionally substituted moieties of compounds of the invention include, but are not limited to aliphatic; heteroaliphatic; aryl; heteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —SO$_2$NR$_x$2; and —NR(CO)R$_x$ moieties—wherein each occurrence of R$_x$ is a group independently chosen from: H; an aliphatic or heteroaliphatic moiety which may be substituted or unsubstituted, branched or unbranched, cyclic or acyclic; and an optionally substituted aryl or heteroaryl moiety. In addition, substituents include phosphorus-containing moieties, as defined herein including the various illustrative series of phosphorus-containing moieties (e.g. Series I, Ia, Ib, Ic, II, Ia, IIb, etc.). Additional examples of generally applicable substituents are illustrated by the specific embodiments shown in the Examples that are described herein. The foregoing is intended to be encompassed by references to "substituents" and "substituted" in this document.

The terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. It will also be appreciated that aryl and heteroaryl moieties, as defined herein may be attached via an alkyl or heteroalkyl moiety and thus also include -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(alkyl)aryl, -(heteroalkyl)aryl, -(heteroalkyl)aryl, and -(heteroalkyl)heteroaryl" are interchangeable. Substituents for exemplary aryl and heteroaryl moieties include, but are not limited to, any of the substitutents previously mentioned or alluded to. In certain embodiments, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one or more (e.g. 1, 2 or 3) of the hydrogen atoms thereon with substituents such as are described herein or illustrated in any of the illustrative examples herein.

The term "cycloalkyl", as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted as previously described.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be substituted or unsubstituted, branched, unbranched, cyclic or acyclic, and include saturated and unsaturated heterocycles such as morpholino, pyrrolidinyl, etc.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group, having one to four heteroatoms independently chosen from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The heterocyclic moiety may be substituted or unsubstituted.

As used herein, the phrase, "phosphorus-containing moiety" includes, but is not limited to, phosphites, phosphonites, phosphenites, phosphines, phosphates, phosphonates, phosphenates, phosphine oxides, bisphosphonates, thiophosphates, thiophosphonates, thiophosphenates, thiophosphine oxides, mono- or (where permitted) di- or tri amides and esters of any of the foregoing as well as the phosphorus-containing moieties disclosed in Series I, Ia, Ib, Ic, II, IIa, IIb or III or otherwise described herein, including in the accompanying text and illustrative classes, subclasses, and species of compounds disclosed herein.

4. Synthetic Overview

The practitioner has a well-established literature of quinolinone chemistry to draw upon, in combination with the information contained herein, for guidance on synthetic strategies, protecting groups, and other materials and methods useful for the synthesis of the compounds of this invention, including compounds containing the various $R^A$, $R^B$, $R^C$ and $R^D$ substituents.

The various patent documents and other references cited herein provide helpful background information on producing variously analogously substituted quinolinones or relevant intermediates, as well as information on formulation, uses, and administration of prior quinolinones which may be of interest.

Moreover, the practitioner is directed to the specific guidance and examples provided in this document relating to the various phosphorus-containing moieties and intermediates containing them.

Numerous suitable prodrug moieties, and information concerning their selection, synthesis and use are well known, beginning with lower alkyl esters of phosphonates and related moieties. Other prodrug moieties of interest include, among others, the following:

| R | |
|---|---|
| 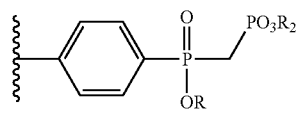 | |
| 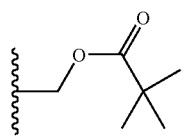 | Atack, J. R. et al. J. of Pharmacology and Experimental Therapeutics 1994, 270, 70 |
| 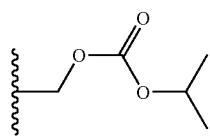 | Arimilli, M. N, et al. Antiviral Chemistry & Chemotherapy 1997, 8, 557. |
| 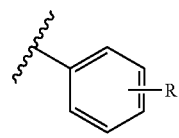 | Serafinowska, H. T., et el. J. Med. Chem. 1995, 35, 1372. |
|  | Ahlmark, M., J. Med. Chem. 1999, 42, 1473. |
| 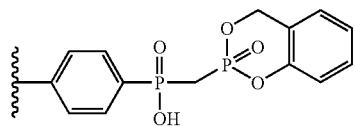 | Meier, C., et al. J. Med. Chem. 1998, 41, 1417. |

Review:
Krise, J. P., Stella, V. J. Advanced Drug Delivery Reviews 1996, 19, 287. and references cited therein.

Other prodrug moieties of interest that can be attached to primary or secondary amine-containing functionality at groups $R^B$, $R^C$, and $R^D$ include the following:

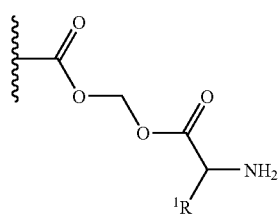

$R^1$ = all natural, unnatural amino acids

For the synthesis of the prodrug groups, see Borchardt, R. T. et. al., J. Org. Chem. 1997, 43, 3641–3652.

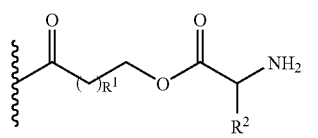

$R^1$ = C1–C4 alkyl, cycloalkyl, oxyalkyl, aminoalkyl, etc.
$R^2$ = all natural, unnatural amino acids For the synthesis of the prodrug groups, see Zhou, X-X. et. al., PCT WO 99/51613.

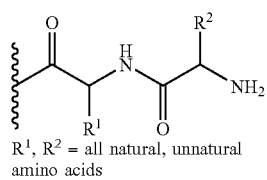

R¹, R² = all natural, unnatural amino acids

For the synthesis of the prodrug groups, see Ezra, A. et. al., J. Med. Chem. 2000, 43, 3641–3652.

Uses, Formulations, Administration

Pharmaceutical Compositions

The inclusion of a phosphorus-containing moiety in the design of the compounds of this invention can impart interesting functional characteristics to the compounds. For instance, depending in some cases on the choice of phosphorus-containing moiety and/or its location in the compound, characteristics of the compounds such as in vitro or in vivo potency, ClogP, aqueous solubility, ability to penetrate cells, and ability to target bone tissue may be desirably affected. As discussed above the novel compounds of this invention have biological properties which make them of interest for the treatment of bone disorders, disorders related to cellular proliferation (e.g., cancer), and disorders resulting from increased vascular permeability and/or angiogenesis.

Thus, in one aspect of the invention, compositions are provided which contain at least one of the compounds described herein (or a prodrug, pharmaceutically acceptable salt or other pharmaceutically acceptable derivative thereof), and optionally comprise one or more pharmaceutically acceptable excipients, diluents and/or carriers.

In certain embodiments, these compositions optionally further comprise, or are administered conjointly with, one or more additional therapeutic agents. For example, the additional therapeutic agent may be an anticancer agent, an agent for the treatment of a bone disorder, or an agent for the treatment of disorders related to increased vascular permeability and/or angiogenesis, as discussed in more detail herein.

As noted previously, certain of the compounds of this invention can exist in free form, or where appropriate, as a pharmaceutically acceptable derivative thereof. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts of various classes of compounds including amines, carboxylic acids, phosphonates and others are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of this invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds of the Invention

As discussed herein, compounds of this invention may be used for inhibiting the activity of certain tyrosine kinases, and thus are useful generally for disorders mediated by those kinases, and in certain embodiments, are useful for the treatment of proliferative disorders including among others certain cancers. Additionally, various compounds of the invention may be used to inhibit osteoclast activity and/or promote bone-forming activity and to thus tilt the balance of bone resorption and bone growth positively, i.e., away from net bone loss. Furthermore, certain inventive compounds are useful in inhibiting angiogenic acitivity. As such, the compounds of the invention may be useful in the treatment of bone disorders, proliferative disorders, including, but not limited to cancer, and disorders related to increased angiogenic activity.

Thus, administering to a subject in need thereof a therapeutically effective amount of a compound of the invention, or a composition containing such compound or a pharmaceutically acceptable derivative thereof, provides a method for the treatment of those disorders. A "therapeutically effective amount" is an amount effective for detectably ameliorating the disorder, e.g., an amount effective for detectably killing or inhibiting the growth of tumor cells; for inhibiting osteoclast activity, slowing bone resorption, increasing bone growth or reducing serum calcium levels; or for inhibiting antiangiogenesis or edema or a manifestation thereof.

The compounds and compositions, according to the method of the present invention, may be administered using any dosage amount and any route of administration effective for the treatment of disorders in question. The exact dosage amount will vary from subject to subject, depending on the species, age, and general condition of the subject, the nature and severity of the disorder, the overall efficacy of the agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, in one aspect, the compounds of this invention are useful as anticancer agents, and thus may be useful in the treatment of cancer, by effecting tumor cell death or inhibiting the growth of tumor cells. In certain embodiments, compounds of the invention are useful as inhibitors of EGF. Without wishing to be bound by any particular theory, it is known that the EGF family of receptor tyrosine kinases (and certain other receptor tyrosine kinases) are frequently present in common human cancers such as breast cancer (Sainsbury et. al., *Brit. J. Cancer*, 1988, 58, 458; Guerin et al., *Oncogene Res.*, 1988, 3, 21 and Klijn et al., *Breast Cancer Res. Treat.*, 1994, 29, 73), non-small cell lung cancers (NSCLCs) including adenocarcinomas (Cerny et al., *Brit. J. Cancer*, 1986, 54, 265; Reubi et al., *Int. J. Cancer*, 1990, 45, 269; and Rusch et al., *Cancer Research*, 1993, 53, 2379) and squamous cell cancer of the lung (Hendler et al., *Cancer Cells*, 1989, 7, 347), bladder cancer (Neal et. al., *Lancet*, 1985, 366), oesophageal cancer (Mukaida et al., *Cancer*, 1991, 68, 142), gastrointestinal cancer such as colon, rectal or stomach cancer (Bolen et al., *Oncogene Res.*, 1987, 1, 149), cancer of the prostate (Visakorpi et al., *Histochem. J.*, 1992, 24, 481), leukaemia (Konaka et al., *Cell*, 1984, 37, 1035) and ovarian, bronchial or pancreatic cancer (European Patent Specification No. 0400586). It is also known that EGF receptors which possess tyrosine kinase activity are overexpressed in many human cancers such as brain, lung squamous cell, bladder, gastric, breast, head and neck, oesophageal, gynaecological and thyroid tumours. Accordingly it has been recognised that an inhibitor of receptor tyrosine kinases should be of value as a selective inhibitor of the growth of mammalian cancer cells (Yaish et al. *Science*, 1988, 242, 933).

In general, the inventive anticancer agents are useful in the treatment of cancers and other proliferative disorders, including, but not limited to breast cancer, cervical cancer, colon, stomach and rectal cancer, leukemia, lung cancer, melanoma, multiple myeloma, non-Hodgkin's lymphoma, ovarian cancer, pancreatic cancer, prostate cancer, head, neck, oesophageal, gynaecological, thyroid, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

As discussed above, in another aspect, the compounds of this invention are useful in the selective treatment or prevention of bone disorders, and may effect treatment via inhibition of osteoclast activity, promotion of osteoblast activity, or promotion or inhibition of other cellular events necessary for healthy bone metabolism. In certain preferred embodiments, these compounds are useful for the treatment or prevention of diseases and conditions associated with bone metabolic disorders such as osteoclast overactivity. In still other embodiments, the compounds of this invention are targeted Src kinase inhibitors and thus inhibit bone resorption by osteoclasts.

The present invention therefore provides a method for the treatment, prophylaxis, and/or prevention of bone and other related disorders which method comprises the administration of an effective non-toxic amount of an inventive compound, or a pharmaceutically composition thereof. As mentioned above, although the inventive compounds effect treatment via several mechanisms, (i.e. inhibition of osteoclast activity, promotion of osteoblast activity, or regulation of other cellular events necessary for healthy bone metabolism), in certain preferred embodiments, these compounds are selective inhibitors of osteoclast activity.

In a further aspect, the present invention provides an inhibitor of mammalian osteoclasts, for example any one of the compounds of this invention or a pharmaceutical composition thereof. In still another aspect, the present invention provides compounds or pharmaceutical compositions that are selective Src kinase inhibitors. In particular, the method of present invention comprises providing any one of the compounds of this invention or a pharmaceutically composition thereof, for use in the treatment of and/or prophylaxis of osteoporosis and related osteopenic diseases.

It will be appreciated that, in addition to the treatment or prevention of osteoporosis, particularly osteoporosis associated with the peri and post menopausal conditions, the present invention also contemplates the treatment and prophylaxis or prevention of Paget's disease, hypercalcemia associated with bone neoplasms and other types of osteoporotic diseases and related disorders, including but not limited to involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agensis or Turner's syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration, and chronic ingestion of anticonvulsant drugs.

In yet another embodiment, in addition to the treatment or prevention of osteoporosis or cancer, the present invention can be utilized to inhibit increases in vascular permeability. For example, certain compounds are tested for the ability to inhibit the tyrosine kinase activity associated with the VEGF receptors such as Flt and/or KDR and for their ability to inhibit angiogenesis and/or increased vascular permeability. Additionally, these compounds can be tested for the ability to inhibit the tyrosine kinase activity associated with Src and for their ability to inhibit angiogenesis and/or increased vascular permeability. These properties may be assessed, for example, using one or more of the procedures set out below. Thus according to this aspect of the invention there is provided a method for reducing vascular permability in a subject comprising administering a compound of Formula I, as described herein and as described by the various classes and subclasses.

It will be appreciated that, similarly to the anticancer treatment and treatment for osteoporosis, as also described herein, the antiangiogenic and/or vascular permeability reducing treatment defined herein may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined herein may be: surgery, radiotherapy or chemotherapy. Such chemotherapy may cover three main categories of therapeutic agent:

(1) other antiangiogenic agents that work by different mechanisms from those defined hereinbefore (for example linomide, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5.alpha.-dihydroreductase (for example finasteride), anti-invasion agents (for example metalloproteinase inhibitors like marimastat and inhibitors of urokinase plasminogen activator receptor function) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

As stated above, in another embodiment of the invention, the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular, such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the substituted purine dosages, can be included to provide a kit in which a dosage is taken every day. Optionally associated with such container (s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXAMPLES

Example 1

Certain Exemplary Compounds

General Synthetic Overview

The practitioner has a well-established literature of heterocyclic and quinolinone chemistry to draw upon, in combination with the information contained in the many examples which follow, for guidance on synthetic strategies, protecting groups, and other materials and methods useful for the synthesis of the compounds of this invention, including compounds containing phosphorus-containing moieties at either one or both of $R^B$ and $R^D$. The following references, and the references cited therein, may be of particular interest: U.S. Pat. Nos. 6,037,350; 6,169,096; 6,150,377; Published PCT applications: WO97/21701; WO98/55124; WO00/01411; WO00/01386; WO99/20612; WO00/12498; WO00/12499; WO02/24683; WO02/24686 and WO02/24687, to name a few. A quinolinone derivative of Formula I, or a pharmaceutically-acceptable derivative or salt thereof, may be prepared using any of the available relevant chemical transformations, combined with protection and deprotection as desired or required. Such processes, when used to prepare a quinolinone derivative of the formula I, or a pharmaceutically-acceptable salt thereof, are illustrated by the following representative examples. The various starting materials are either commercially available or may be obtained by standard procedures of organic chemistry. The preparation of such starting materials is described within the accompanying non-limiting Examples.

Additionally, as detailed in the specification, a variety of phosphorus-containing moieties are utilized for the compounds of the invention. In addition to the phosphorus-containing moieties as described above and in PCT/US/34487, PCT/US/00/34417, 09/740,653, and 09/740,267, the entire contents of which are hereby incorporated by reference, certain other phosphorus-containing moieties, such as the described dialkyl phenyl phosphine oxide compounds can be synthesized according to the procedures and schemes outlined herein.

A) Synthesis of Exemplary Phosphorus-Containing Moieties (PCM):

Schemes 1, 2 and 3 illustrate synthetic routes for preparing various phosphonates, phosphonate esters and phosphine oxides. Those and some other exemplary phosphorus-containing moieties are detailed in our specific examples. Others within the scope of this invention will be readily accessible to the practitioner.

Preparation of Alkylphosphine Oxides

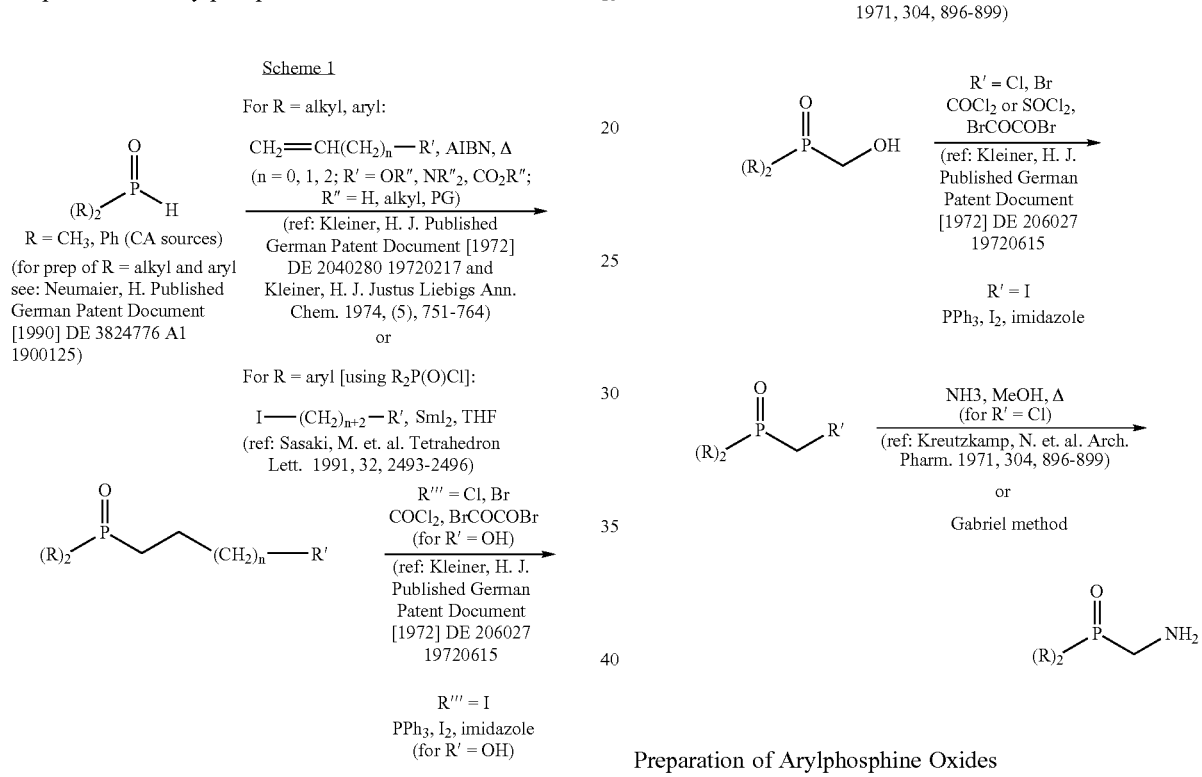

Preparation of Arylphosphine Oxides

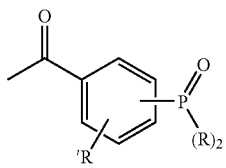

1. EtO(SnMe$_3$)C=CH$_2$,
   Pd(Ph$_3$P)$_4$, tol
2. HCl, THF
(ref: Kwon, H. B. et. al.
J. Org. Chem. 1990,
55, 3114-3118)

or

1. Zn, CuCN·2LiBr
2. CH$_3$COCl
(ref: Rieke, R. D. et. al. J. Org. Chem. 1991, 56, 1445-1453)

-continued

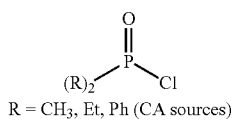

For R = alkyl, aryl:
R = CH₃, Et, Ph (CA sources)
(for prep of R = alkyl and aryl, see: Aksnes, G. et. al. Phosphorous Sulfur 1986, 26, 261-274 and Hashiba, I. et. al. Published Japanese Patent Document [1997] JP 09176175 A219970708 Heisei, respectively)

dibromobenzene, Mg, Et₂O
or
dibromopyridine, iPrMgCl or BuLi
(for prep of 4-bromophenylmagnesium bromide, see: McMahon, R. J. et. al. J. Org. Chem. 1995, 60, 3499-3508; for regioselective prep of bromopyridylmagnesium bromides and monolithium reagents, see: Trecourt, F. et. al. Tetrahedron 2000, 56, 1349-1360 and Wang, X. et. al. Tetrahedron Lett. 2000, 41, 4335-4338, respectively; for coupling, see: (alkyl) Ikai, K. et. al. Synthesis 1989, (8), 595-597 and (aryl) Mashima, K. et. al. J. Org. Chem. 1994, 59, 3064-3076)

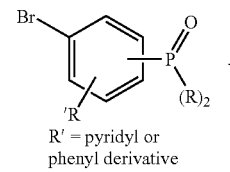

R' = pyridyl or phenyl derivative

1. Mg, Et₂O
2. (PhO)₂P(O)N₃, Et₂O
3. HCl, MeOH
(ref: Mori, S. et. al. Chem. Pharm. Bull. 1986, 34, 1524-1530)

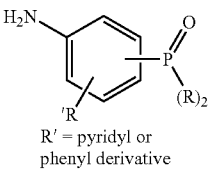

R' = pyridyl or phenyl derivative

CO, PdCl₂(Ph₃P)₂, Ph₃P, Bu₃N, H₂O
(ref: Rama, D. A. et. al. Tetrahedron. 1994, 50, 2543-2550)

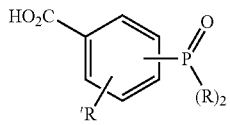

Preparation of Alkyl and Aryl Phosphonates

Scheme 3

Alkyl Esters

BnO(CH₂)nBr $\xrightarrow{\text{1. Arbuzov} \atop \text{2. H}_2\text{Pd/C}}$

HO(CH₂)nPO₃R₂ $\xrightarrow{\text{1. MsCl} \atop \text{2. NaN}_3 \atop \text{3. H}_2\text{Pd/C}}$ H₂N(CH₂)nPO₃R₂

CrO₃, H₂SO₄ water, Acetone
Tetrahedron: Asymmetry, 1996, 7, 2743-2754.

PPh₃, Br₂
Org. Prep. Proced. Int., 1988, 20, 371-6

Br(CH₂)nPO₃R₂

CO₂H(CH₂)n•₁PO₃R₂

Aryl Esters

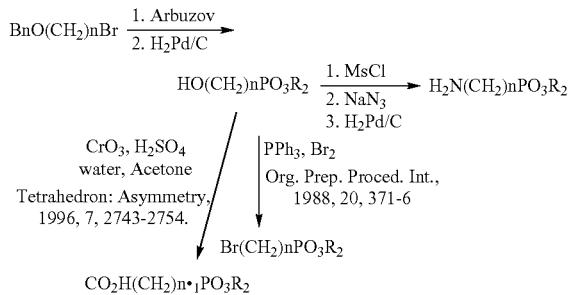

Zh. Obshch. Khim., 1989 59, 2692-4.

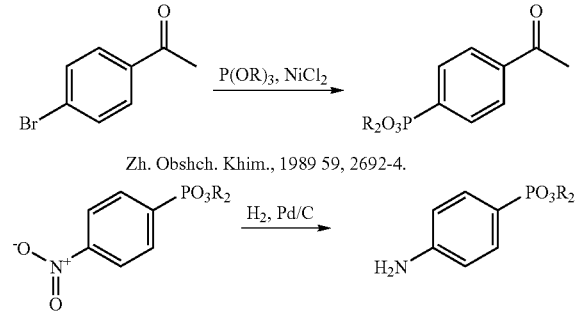

See Bull Chem. Soc. Jpn. 1982, 55, 909 for starting nitro compound

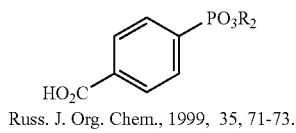

Russ. J. Org. Chem., 1999, 35, 71-73.

1) 4-(Dimethyl-phosphinoyl)-phenylamine hydrochloride

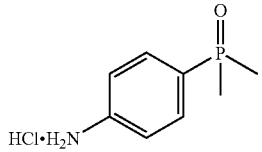

Step 1: 1-(Dimethyl-phosphinoyl)-4-fluoro-benzene

To a cooled (0° C.) flask containing 34.0 mL (2.0 M in Et₂O, 68.4 mmol) of 4-fluorophenylmagnesium bromide, under an atmosphere of N₂, was added a solution of dimethylphosphinic chloride (3.50 g, 31.1 mmol) in 84 mL of THF, dropwise via cannulation, over 20 min. The green reaction mixture was stirred at 0° C. for 1 h, then quenched at 0° C. with 30 mL of saturated NH₄Cl resulting in the formation of a white precipitate. The mixture was concentrated on a rotary evaporator and partitioned between EtOAc (200 mL) and H₂O (200 mL), upon which the layers were separated. The aqueous layer was extracted with EtOAc (3×100 mL) and the combined organics washed with brine, then dried over MgSO₄ and concentrated. The crude product was purified by silica gel flash chromatography (eluted with 5% MeOH/DCM) to provide 2.08 g of an off-white solid: $^1$H NMR (300 MHz, DMSO-d₆) δ 7.83 (m, 2 H), 7.35 (td, J=8.9, 1.7 Hz, 2H), 1.66 (s, 3H), 1.61 (s, 3H). $^{31}$P NMR (121 MHz, DMSO-d₆) δ 37.186. $^{19}$F NMR (282 MHz, DMSO-d₆) δ −105.14.

Step 2: 1-(Dimethyl-phosphinoyl)-4-nitro-benzene

A sealed pressure flask, flushed with N₂, containing a mixture of 3.90 g (22.7 mmol) of 1-(Dimethyl-phosphinoyl)-4-fluoro-benzene and 6.0 g (113.3 mmol) of LiNO₂ (for prep see, W. C. Ball and H. H. Abram *J. Chem. Soc.* 1913, 103, 2130–2134) in 27 mL of DMPU (1,3-dimethyl-3,4,5,6-tetrahydro-2(H)-pyrimidinone) was stirred at ambient temperature for 5–10 min (to dissolve fluoro compound) then heated at 190° C. for 3 days. The resulting dark brown solution was cooled to ambient temperature, diluted with 300 mL of brine, then extracted with EtOAc (10×100 mL) until the aqueous layer showed little or no evidence of product by HPLC. The combined organics were dried over MgSO$_4$ and concentrated. The excess DMPU was removed via short-path distillation (120° C./0.3 mm) to provide a semi-solid, which was dissolved in a minimum amount of iPrOH and purified by silica gel flash chromatography (eluted with 5% iPrOH/DCM, then 10% iPrOH/DCM, then 15% iPrOH/DCM) to provide 2.04 g of an yellow solid: $^1$H NMR (300 MHz, DMSO-d$_6$) δ 8.34 (dd, J=8.7, 1.9 Hz, 2H), 8.07 (dd, J=10.6, 8.8 Hz, 2H), 1.75 (s, 3H), 1.70 (s, 3H). $^{31}$P NMR (121 MHz, DMSO-d$_6$) δ 37.89.

Step 3: 4-(Dimethyl-phosphinoyl)-phenylamine hydrochloride

A suspension of 1-(Dimethyl-phosphinoyl)-4-nitro-benzene (2.04 g, 10.2 mmol) and 10% palladium on carbon (0.411 g) in 103 mL of absolute EtOH containing 1.15 mL (11.4 mmol) of conc. HCl was flushed with H$_2$ and stirred at ambient temperature (H$_2$ balloon) for 2 h. The reaction mixture was filtered through Celite, the Celite washed with EtOH, and the combined filtrates concentrated to provide the crude product. Recrystallization from boiling iPrOH (10 mL) provided, after several crops, 1.17 g of an off-white solid: $^1$H NMR (300 MHz, DMSO-d$_6$) δ 7.61 (dd, J=11.1, 8.4 Hz, 2H), 7.04 (dd, J=8.4, 2.0 Hz, 2H), 1.64 (s, 3H), 1.60 (s, 3H). $^{31}$P NMR (121 MHz, DMSO-d$_6$) δ 39.299.

2) [(3-Amino-propyl)-ethoxy-phosphinoylmethyl]-phosphonic acid diethyl ester

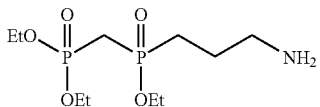

[(3-Benzyloxy-propyl)-ethoxy-phosphinoylmethyl]-phosphonic acid diethyl ester:

To an oven-dried flask was added 10.25 g (44.7 mmol) of (3-Bromo-propoxymethyl)-benzene and 7.67 mL (44.7 mmol) of triethyl phosphite. The flask was fitted with a short-path distillation head, for removal of bromoethane, and the mixture heated at 150° C. for 4 h. The reaction was cooled to ambient temperature, and then diluted with 120 mL of absolute ethanol and 1.8 N KOH (120 mL, 216 mol). The distillation head was replaced with a reflux condenser and the solution heated at reflux for 5 h. The reaction was cooled then concentrated in vacuo. The basic aqueous layer was extracted with EtOAc (2×) and then acidified to pH 3 with conc. HCl. The aqueous layer was extracted with EtOAc (3×) and the combined extracts were dried over MgSO$_4$ and concentrated. The resulting crude product (8.24 g) was used as is in the next reaction. $^{31}$P NMR (300 MHz, DMSO-d$_6$) δ 34.113.

To a solution of the crude phosphonate (8.24 g, 32.5 mmol) in 100 mL CH$_2$Cl$_2$, under an atmosphere of N$_2$, was added 10.8 mL (113.8 mmol) of oxalyl chloride. DMF (several drops) was slowly added to initiate the reaction. After gas evolution had ceased, the reaction was stirred for 30 min at ambient temperature. Upon concentration in vacuo, the residue was titurated several times with hexane, then dissolved in 167 mL of anhydrous THF. In a separate flask, a cooled (–78° C., under N$_2$) solution of diethyl methylphosphonate (10.25 mL, 69.9 mmol) in 337 mL of anhydrous THF was added 2.5 M n-butyl lithium (27.95 mL, 69.9 mmol) dropwise. The reaction mixture was stirred for 30 min at –78° C., at which time the in situ generated acid chloride was added dropwise. The solution was stirred for an additional 2.5 h at –78° C., quenched with 5 mL glacial acetic acid, and then warmed to ambient temperature. Water was added to the reaction mixture and the THF was removed in vacuo. The aqueous layer was extracted with EtOAc (3×) and the combined organics washed with saturated NaHCO$_3$, brine, then dried over MgSO$_4$ and concentrated. The crude product was purified by silica gel chromatography (eluted with 50:1 CH$_2$Cl$_2$/MeOH) affording 6.15 g of a yellow oil. $^{31}$P NMR (300 MHz, DMSO-d$_6$) δ 51.479, 26.291.

[(3-Amino-propyl)-ethoxy-phosphinoylmethyl]-phosphonic acid diethyl ester:

To a solution of [(3-Benzyloxy-propyl)-ethoxy-phosphinoylmethyl]-phosphonic acid diethyl ester (5.7 g, 14.5 mmol) in 100 mL of EtOH was added 1.2 g of palladium on carbon. The mixture was flushed with H$_2$ and stirred at ambient temperature (H$_2$ balloon) for 1 h. The reaction mixture was filtered through Celite and the solvent evaporated to provide 3.5 g of a pale yellow oil. $^{31}$P NMR(300 MHz, DMSO-d$_6$) d 52.219, 26.317.

To a cooled (0° C., under N$_2$) solution of the crude alcohol (3.5 g, 14.5 mmol) in 53 mL of CH$_2$Cl$_2$ was added 2.4 mL (17.4 mmol) of triethylamine followed by 1.25 mL (16 mmol) of methanesulfonyl chloride. The reaction mixture was warmed to ambient temperature and stirred for 1 h. The reaction mixture was then quenched with water and the layers separated. The organic layer was washed with water and brine, dried over Na$_2$SO$_4$, and concentrated. The crude orange-yellow oil (5.5 g) was used as is in the next reaction. $^{31}$P NMR (300 MHz, DMSO-d$_6$) δ 51.135, 26.614.

To a solution of the crude mesylate (5.5 g, 14.4 mmol) in 17 mL DMF was added 4.7 g (72.4 mmol) of sodium azide. The resulting slurry was heated at 55° C. and stirred overnight. The reaction mixture was diluted with EtOAc and washed with water (2×). The combined organics were then dried over Na$_2$SO$_4$ and concentrated. The crude azide (2.61 g) was used as is in the next reaction. $^{31}$P NMR (300 MHz, DMSO-d$_6$) d 51.230, 26.183.

To a solution of the crude azide (2.61 g, 8 mmol) in 100 mL of EtOH was added 0.8 g of palladium on carbon. The mixture was flushed with H$_2$ and stirred at ambient temperature (H$_2$ balloon) for 16 h. The reaction mixture was filtered through Celite and the solvent evaporated to provide 2.3 g of a yellow oil: $^1$H NMR (300 MHz, DMSO-d$_6$) δ 4.03 (m, 6H), 2.84–2.52 (m, 4H), 1.91–1.80 (m, 2H), 1.65–1.61 (m, 2H), 1.23 (m, 9H). $^{31}$P NMR (300 MHz, DMSO-d$_6$) δ 51.757, 26.344.

3) [(4-Amino-phenyl)-ethoxy-phosphinoylmethyl]-phosphonic acid diethyl ester

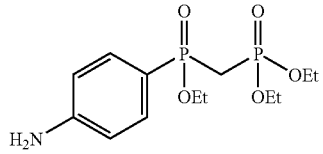

Step 1: [(4-Nitro-phenyl)-ethoxy-phosphinoylmethyl]-phosphonic acid diethyl ester:

A mixture of diethyl (ethoxyphosphinyl)methylphosphonate (2.35 g, 9.62 mmol), Et$_3$N (3.8 mL, 27.5 mmol), 1-iodo-4-nitrobenzene (2.28 g, 9.17 mmol) and Pd(PPh$_3$)$_4$ (265 mg, 0.229 mmol) in CH$_3$CN (14 mL) under N$_2$ was stirred at 80° C. for 2.5 h. After cooling to rt, the reaction mixture was poured into 50 mL of 1 N aq HCl and extracted with CH$_2$Cl$_2$. The extract was washed with H$_2$O (50 mL) and brine (50 mL). The aqueous washes were reextracted once with CH$_2$Cl$_2$, and the combined extracts were dried over Na$_2$SO$_4$ and concentrated. The crude material was purified by flash chromatography on silica gel. Elution with 30:1 CHCl$_3$-MeOH followed by 20:1 CHCl$_3$-MeOH and finally 15:1 CHCl$_3$-MeOH afforded 3.28 g of the desired (arylphosphinylmethyl)phosphonate.

Step 2: [(4-Amino-phenyl)-ethoxy-phosphinoylmethyl]-phosphonic acid diethyl ester:

A mixture of [(4-nitro-phenyl)-ethoxy-phosphinoylmethyl]-phosphonic acid diethyl ester (940 mg, 2.57 mmol) and SnCl$_2$.2H$_2$O (2.9 g, 12.9 mmol) in EtOH (~10 mL) was stirred at 70° C. for 44 min and then concentrated at ambient temperature. The residue was taken up in CH$_2$Cl$_2$ and washed with half saturated aq NaHCO$_3$ (40 mL), H$_2$O (40 mL) and brine (40 mL). The aqueous washes were reextracted once with CH$_2$Cl$_2$, and the combined extracts were dried over K$_2$CO$_3$ and concentrated. The crude material was purified by flash chromatography on silica gel. Elution with 20:1 CHCl$_3$-MeOH followed by 15:1 CHCl$_3$-MeOH afforded 657 mg of product.

4) Synthesis of Phosphorous-containing Alkyl Tosylates:

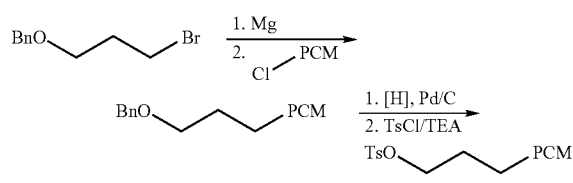

Exemplary phosphorus-containing moieties include, but are not limited to:

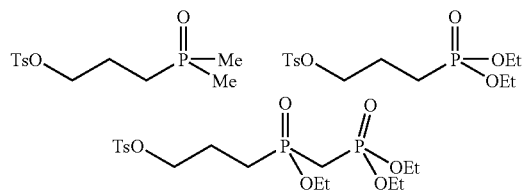

5) Preparation of 4-(Dimethylphosphinoyl)-benzoic acid (1c):

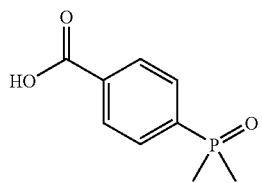

Step 1: 1-(Dimethyl-phosphinoyl)-4-methyl-benzene (Ib)

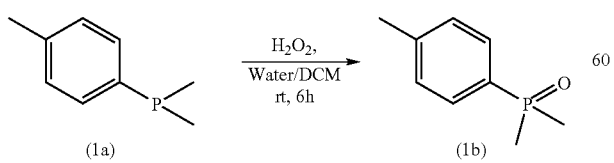

To a solution of dimethyl-p-tolyl phosphane (25 g, 0.165 mol) (1a) in diclholoromethane (DCM) (50 mL) was added an aqueous solution of hydrogen peroxide (10%, 60 mL, 0.176 mol) in drops. This is an exothermic reaction so the flask was cooled in ice water during the addition. After the addition the reaction was allowed to stir at rt overnight until the HPLC showed no starting material (18 h). From the resulting reaction mixture the organic phase was separated and the aqueous phase was extracted with additional dichloromethane (3_60 mL) until the aqueous layer showed little or no evidence of product by HPLC. The combined organics were washed with a solution of sodium bisulfite (10 mL) followed by water (10 mL) and dried over Na$_2$SO$_4$ and concentrated on a rotary evaporator. The desired product was purified by Crystallization from ethyl acetate/hexane (18.8 g). m.p. 90–92° C., $^1$H NMR (300 MHz, CDCl$_3$) δ (ppm)) 1.469 (d, J=13 Hz, 6H), 2.16 g (s, 3H), 7.04 (d, J=5.5 Hz, 2H), 7.38 (m, 2H). $^3$P NMR (121 MHz, CDCl$_3$) δ 34.327.

Step 2: 4-(Dimethyl-phosphinoyl)-benzoic acid (Ic)

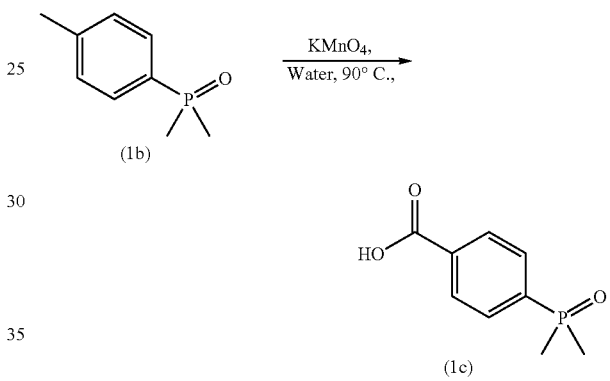

To a solution of 1-(Dimethyl-phosphinoyl)-4-methyl-benzene (1b) (15.48 g, 0.09205 mol) in water (155 mL) at 80° C. was added slowly and carefully a solution of potassium permanganate (34.64 g, 0.2192 mol, in 400 mL water). The resulting reaction mixture was stirred at 100° C. for 18 hours. The reaction mixture was filtered hot and the residue was washed with hot water (3_30 mL). The aqueous solution was washed with ether (2_50 mL). The aqueous solution was acidified with conc. HCl and concentrated. The residue was triturated with ether and filtered. White solid (15.00 g), mp. 240–242° C. $^1$H NMR (300 MHz, D$_2$O) δ, (ppm)) 1.757 (d, J=13.43 Hz, 6H), 7.72 (m, 2H), 7.90(m, 2H). $^{31}$P NMR (121 MHz, CDCl$_3$) δ, 49.00.

6) Preparation of 4-(Diethoxyphosphoryl)-benzoic acid (2c):

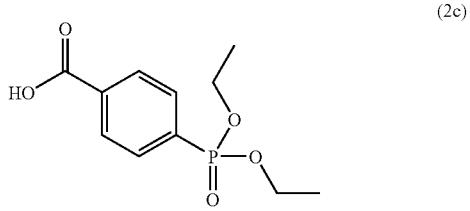

Step 1: 4-(Diethoxyphosphoryl)-benzoic acid ethyl ester (2b)

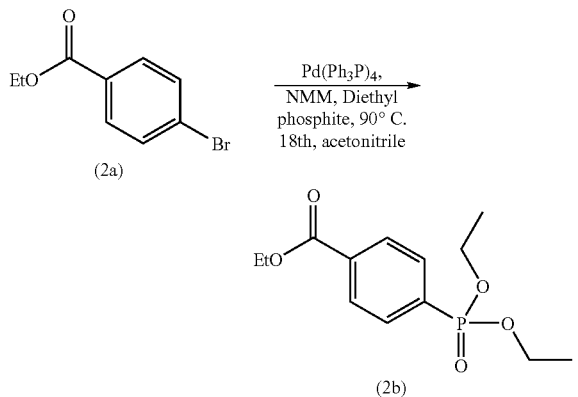

A sealed pressure flask, flushed with N$_2$, containing a mixture of 4-bromo-benzoic acid ethyl ester (2a) (5 g, 0.0218 mol), diethyl phosphite (3.093 mL, 0.024 mol), NMM (2.88 mL, 0.0262 mmol) and Pd(PPh$_3$)$_4$ (2.017 g, 0.00175 mol) in acetonitrile (20 mL) was stirred at ambient temperature for 5–10 min, then heated at 90° C. for 18 hours. The reaction mixture was filtered through celite, and the celite was washed with EtOAc (3_30 mL) until the filtrate showed little or no evidence of product by HPLC. The combined organics were dried over Na$_2$SO$_4$ and concentrated on a rotary evaporator. The desired product was purified by silica gel flash chromatography to give a pale yellow oil (4.24 g). $^1$H NMR (300 MHz, CDCl$_3$) δ (ppm)) 1.36 (m, 6H), 1.42 (t, J=7 Hz, 3H), 4.16 (m, 4H), 4.42 (q, J=7 Hz, 2H), 7.93 (m, 2H), 8.15 (m, 2H). $^{31}$P NMR (121 MHz, CDCl$_3$) δ 17.63.

Step 2: 4-(Diethoxyphosphoryl)-benzoic acid (2c)

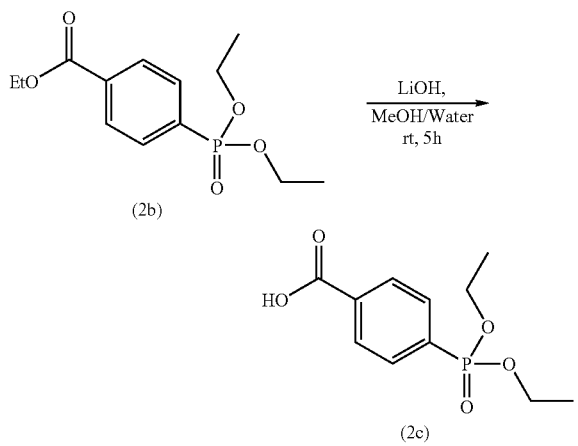

To a solution of 4-(diethoxyphosphoryl)-benzoic acid ethyl ester (2b) (2.46 g, 8.59 mmol) in methanol (86 mL) was slowly added lithium hydroxide (monohydrate, 0.36 g, 8.59 mmol) in water (86 mL). The resulting reaction mixture was stirred at room temperature for 4 hours. The reaction mixture was concentrated to remove methanol and diluted with brine, then extracted with EtOAc (3_100 mL) until the aqueous layer showed little or no evidence of product by HPLC. The combined organics were dried over Na$_2$SO$_4$ and concentrated on a rotary evaporator. The desired product was purified by crystallization from hexane/ethyl acetate (2.37 g), m.p. 101° C. $^1$H NMR (300 MHz, CDCl$_3$) δ (ppm)): 1.27 (t, J=7.03 Hz, 6H), 4.03 (q, J=7.03 Hz, 4H), 7.85 (m, 2H), 8.09 (m, 2H), 12.65 (bs, 1H). $^{31}$P NMR (121 MHz, CDCl$_3$) δ 21.611.

7) Preparation of 4-[(Diethoxyphosphorylmethyl)-ethoxyphosphinoyl]-benzoic acid (3d):

(3d)

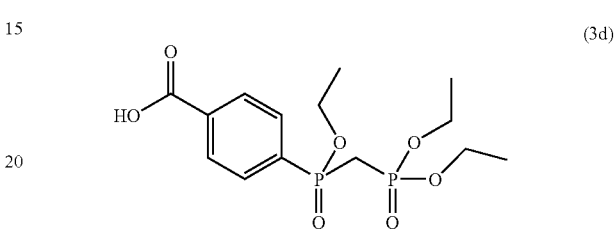

Step 1: 4-[(Diethoxyphosphorylmethyl)-ethoxyphosphinoyl]-benzoic acid ethyl ester (3c)

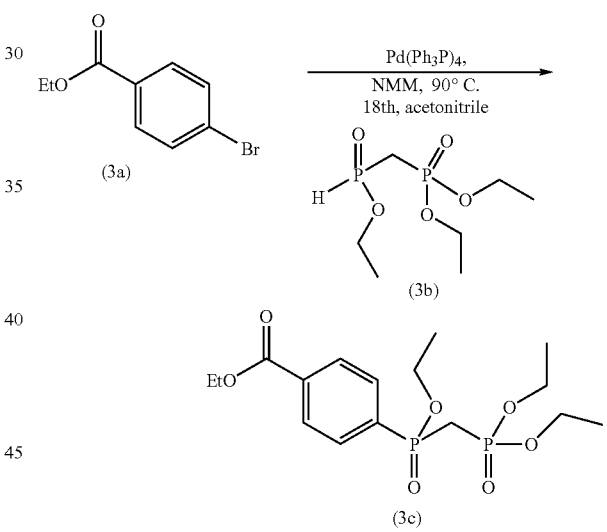

A sealed pressure flask, flushed with N$_2$, containing a mixture of 4-bromo-benzoic acid ethyl ester (3a) (5 g, 0.0218 mol), ethoxyphosphinoylmethyl-phosphonic acid diethyl ester (3b), (5.86 g, 0.024 mol), NMM (2.88 mL, 0.0262 mmol) and Pd(PPh$_3$)$_4$ (2.017 g, 0.00175 mol) in acetonitrile (20 mL) was stirred at ambient temperature for 5–10 min, then heated at 90° C. for 18 hours. The reaction mixture was filtered through celite, and the celite was washed with EtOAc (3_30 mL) until the filtrate showed little or no evidence of product by HPLC. The combined organics were dried over Na$_2$SO$_4$ and concentrated on rotary evaporator. The desired product (ix) was purified by silica gel flash chromatography to give a pale yellow oil (5.01 g). $^1$H NMR (300 MHz, CDCl$_3$) δ (ppm): 0.96 (t, J=7.07 Hz, 3H), 1.13 (m, 9H), 2.41 (t, J=18.2 Hz, 2H), 3.84 (m, 6H), 4.17 (q, J=7.11 Hz, 2H), 7.71 (m, 2H), 7.92 (m, 2H). $^{31}$P NMR (121 MHz, CDCl$_3$) δ 32.8 and 19.7.

Step 2: 4-[(Diethoxyphosphorylmethyl)-ethoxyphosphinoyl]-benzoic acid (3d)

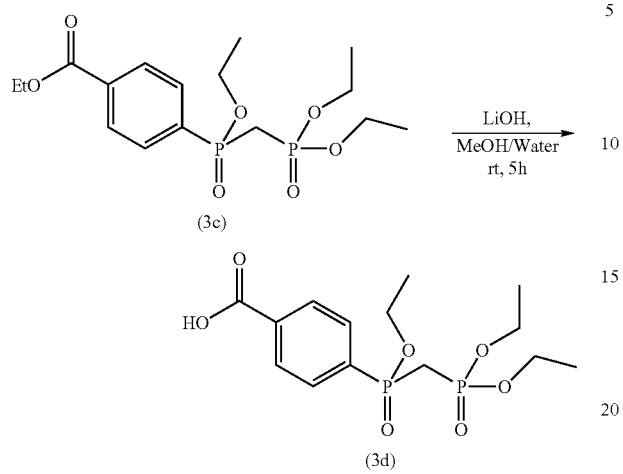

To a solution of 4-[(Diethoxyphosphorylmethyl)-ethoxyphosphinoyl]-benzoic acid ethyl ester (3c) (1 g, 2.55 mmol) in methanol (25 mL) was slowly added lithium hydroxide (monohydrate, 0.11 g, 2.55 mmol) in water (25 mL). The resulting reaction mixture was stirred at room temperature for 4 hours. The reaction mixture was concentrated to remove methanol and diluted with brine, then extracted with EtOAc (3_100 mL) until the aqueous layer showed little or no evidence of product by HPLC. The combined organics were dried over $Na_2SO_4$ and concentrated on rotary evaporator. The desired product (3d) was purified by silica gel flash chromatography as a pale yellow oil (0.91 g). $^1$H NMR (300 MHz, DMSO-$d_6$) δ (ppm)): 1.13 (m, 9H), 2.94 (t, J=18.2 Hz, 2H), 3.85 (m, 6H), 7.88 (m, 2H), 8.02 (m, 2H), 12.60 (bs, 1H), $^{31}$P NMR (121 MHz, DMSO-$d_6$) δ, 37.59 and 24.59

8) Preparation of Compound 4e:

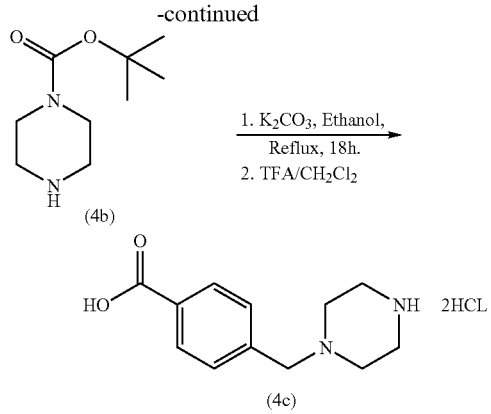

To a solution of 4-bromomethyl-benzoic acid (4a) and 1-t-butoxycarbonyl piperazine(5.95 g, 26.84 mmol) (4b) in ethanol (80 mL) was added potassium carbonate (3.71 g, 26.84 mmol). The resulting reaction mixture was refluxed for 2 hours. The reaction mixture was filtered and the filtrate was concentrated. The residue from the filtrate was dissolved in 25% sodium hydroxide. This aqueous solution was washed with ether (3_50 mL) and cooled. This upon acidification with conc. HCl to pH 2.00 gave a fluffy white solid which was cooled in ice for 30 minutes and filtered. The white solid was washed carefully with ice-water (3_10 mL) and dried in vacuo for 24 h over $P_2O_5$. The solid was pure enough to be used as such, m.p, 253° C. (N-Boc.derivative). $^1$H NMR (300 MHz, DMSO-$d_6$) δ (ppm)): 1.33 (s, 9H), 2.29 and 3.39 (each bs, each 4H), 3.49 (s, 3H), 7.27 (d, J=8.12 Hz, 2H), 7.81 (d, J=8.1 Hz, 2H).

Treating a methylenechloride solution of the above BOC-derivative with TFA in 30 minutes gave the N-TFA salt of the piperazine, which was then used for the following alkylation reactions.

Step 2: 4-[4-(diethoxy-phosphorylmethyl)-piperazin-1-ylmethyl]-benzoic acid (4e)

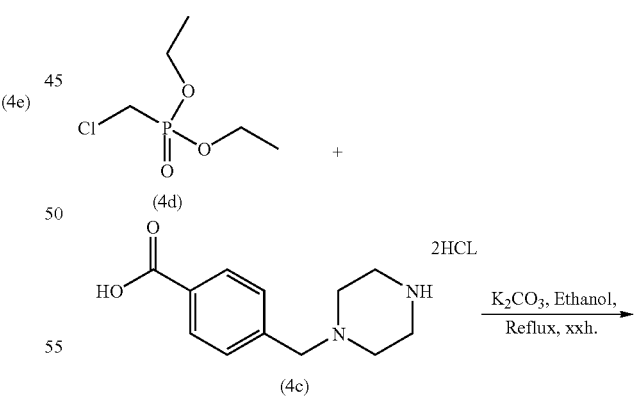

Step 1: 4-Piperazin-1-ylmethyl-benzoic acid (4c)

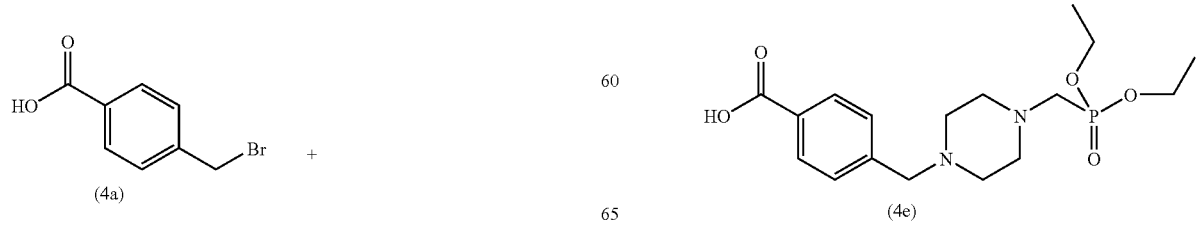

To a solution of 4-Piperazin-1-ylmethyl-benzoic acid (4c) and chloromethyl-phosphonic acid diethyl ester (4d) in ethanol was added potassium carbonate. The resulting reaction mixture was refluxed, then cooled to room temperature, diluted with brine, acidified to pH~4, and extracted with EtOAc until the aqueous layer showed little or no evidence of product by HPLC. The combined organics were dried over MgSO$_4$ and concentrated on rotary evaporator. The desired product was purified by silica gel flash chromatography.

9) Preparation of 4-[4-(dimethyl-phosphinoylmethyl)-piperazin-1-ylmethyl]-benzoic acid (5b)

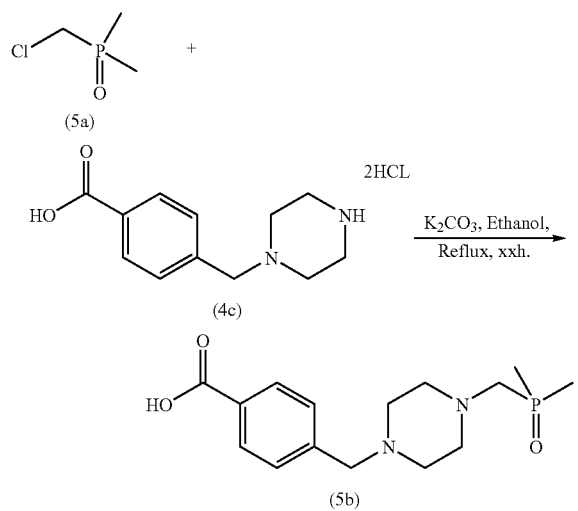

To a solution of 4-Piperazin-1-ylmethyl-benzoic acid (4c) and chloro-(dimethyl-phosphinoyl)-methane (5a) in ethanol was added potassium carbonate. The resulting reaction mixture was refluxed, then cooled to room temperature, diluted with brine, acidified to pH~4, and extracted with EtOAc until the aqueous layer showed little or no evidence of product by HPLC. The combined organics were dried over MgSO$_4$ and concentrated on rotary evaporator. The desired product was purified by silica gel flash chromatography.

10) Preparation of 4-{4-[(diethoxy-phosphorylmethyl)-ethoxy-phosphinoyl methyl]-piperazin-1-ylmethyl}-benzoic acid (6b)

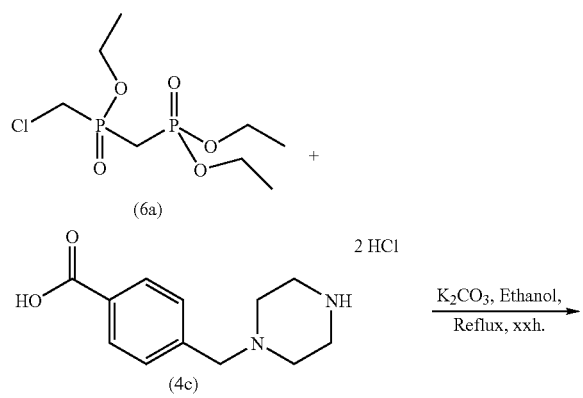

-continued

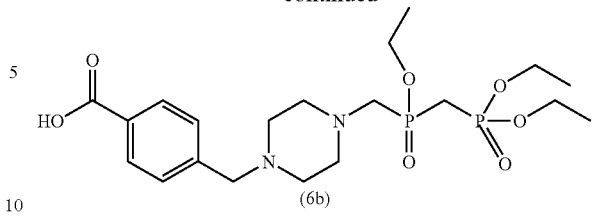

To a solution of 4-Piperazin-1-ylmethyl-benzoic acid (4c) and (chloromethyl-ethoxy-phosphinoylmethyl)-phosphonic acid diethyl ester (6a) in ethanol was added potassium carbonate. The resulting reaction mixture was refluxed, then cooled to room temperature, diluted with brine, acidified to pH~4, and extracted with EtOAc until the aqueous layer showed little or no evidence of product by HPLC. The combined organics were dried over MgSO$_4$ and concentrated on rotary evaporator. The desired product was purified by silica gel flash chromatography.

It will be appreciated that in Sections 11–17 below, R represents a functional group (or latent functional group) suitable for incorporation (via covalent linkage) of the Phosphorus-containing aryl moieties detailed in Sections 11–17 (and derivatives and analogues thereof) into the structure of the compounds of the invention. It will be appreciated that the term "latent functional group" means a precursor functionality that is chemically transformed (through deprotection of chemical derivatization) to give the functional group suitable for attachment of the aryl-PCM onto the inventive constructs. Furthermore, it will be appreciated that the Phosphorus-containing aryl moieties detailed below in Sections 11–17 may further be substituted with one or more occurrences of $R^3$ as defined herein.

11) Preparation of [1-Ethoxy-1-(ethoxy-phenyl-phosphinoyl)-ethyl]phosphonic acid diethyl ester (7c) and [1-Hydroxy-(hydroxy-phenyl-phosphinoyl)-ethyl]-phosphonic acid (7d)

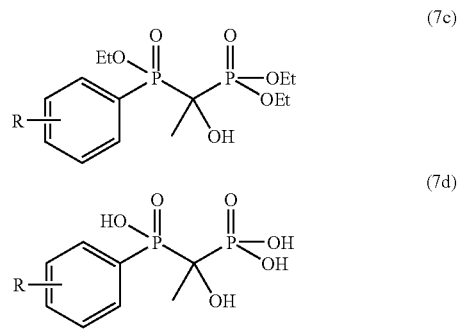

Preparation of: [1-Ethoxy-1-(ethoxy-phenyl-phosphinoyl)-ethyl]phosphonic acid diethyl ester (7c)

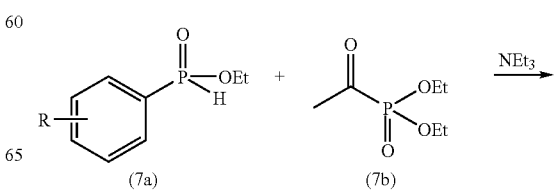

-continued

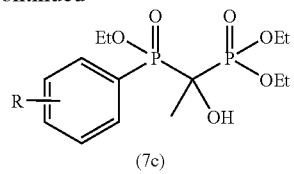

(7c)

Phenyl-phosphinic acid ethyl ester (7a) (170 mg, 1 mmol) was combined with acetyl-phosphinic acid diethyl ester (7b) (525 mg, 2.9 mmol). No reaction was observed. Triethylamine (50 µL, 0.36 mmol) was then added to the mixture, and the solution turned cloudy and with a mild exotherm. The reaction was allowed to stir at room temperature for 20 hours. The following day the mixture was white and the consistency of glue. The mixture was placed on the high vac to remove any excess triethylamine. The residue was dissolved in 12 mL 1:1 $CH_3CN/H_2O$ and filtered through a 0.45 µm syringe filter. The resulting solution was purified by RP HPLC. Lyophilization left a white solid (112 mg, 32%).

Preparation of: [1-Hydroxy-1-(hydroxy-phenyl-phosphinoyl)-ethyl]-phosphonic acid (7d)

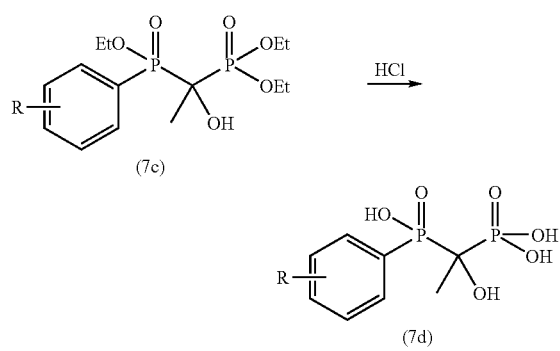

[1-Ethoxy-1-(ethoxy-phenyl-phosphinoyl)-ethyl]phosphonic acid diethyl ester (7c) (67 mg, 1.9 mmol) was combined with concentrated HCl (2 mL). The solution was heated to reflux (120° C.) for 20 hours. The following morning HPLC indicated that all [1-Hydroxy-1-(hydroxy-phenyl-phosphinoyl)-ethyl]phosphonic acid diethyl ester was gone. Excess HCl was removed under a stream of $N_2$ at 100° C. The residue was placed on the high vac for further drying and then dissolved in 6 mL 1:1 $CH_3CN/H_2O$. The solution was filtered through a 0.45 µm syringe filter. The resulting solution was purified by RP HPLC. Lyophilization left a white solid (18 mg, 35%).

12) Preparation of [1-Ethoxy-1-(ethoxy-phenyl-phosphinoyl)-ethyl]phosphonic acid diethyl ester (8c) and [Hydroxy-(hydroxy-phenyl-phosphinoyl)-methyl]-phosphonic acid (8d)

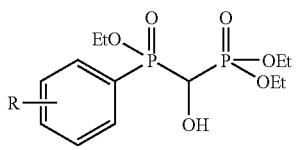

(8c)

-continued

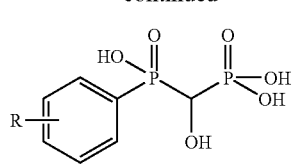

(8d)

Preparation of [1-Ethoxy-1-(ethoxy-phenyl-phosphinoyl)-ethyl]phosphonic acid diethyl ester (8c)

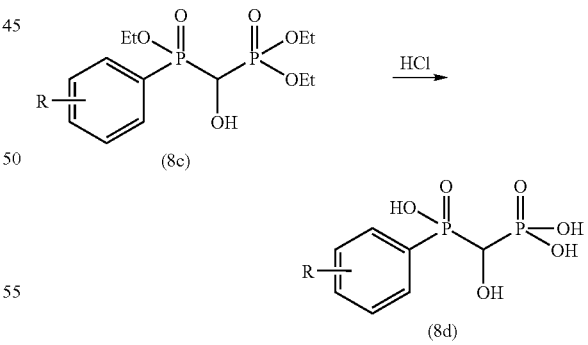

Ref. Zh. Obshch. Khim., 1987, 57, p. 2793.

A reaction sequence similar to that described for the preparation of compound (7c) may be followed. For example, phenyl-phosphinic acid ethyl ester may be reacted with formyl-phosphinic acid diethyl ester in the presence of triethylamine. After allowing the reaction to proceed at room temperature for ~20 hours (or until HPLC indicates that the reaction is complete), excess triethylamine may be removed under high vacuum. The residue may be dissolved in a mixture $CH_3CN/H_2O$ and filtered through a 0.45 µm syringe filter. The resulting solution may be purified by RP HPLC and the purified product may be lyophilized.

Preparation of [Hydroxy-(hydroxy-phenyl-phosphinoyl)-methyl]-phosphonic acid (8d)

A reaction sequence similar to that described for the preparation of compound (7d) may be followed. For example, a mixture of [1-Ethoxy-1-(ethoxy-phenyl-phosphinoyl)-ethyl]phosphonic acid diethyl ester (8c) and a suitable acid (e.g., concentrated HCl or TMS-Br) may be refluxed (120° C.) for ~20 hours (or until HPLC indicates that all of compound xxii has hydrolyzed). Excess HCl may be removed under a stream of $N_2$ at 100° C., and the residue may be further dried under high vacuum. The residue may be dissolved in a mixture CH₃CN/H₂O and filtered through a 0.45 μm syringe filter. The resulting solution may be purified by RP HPLC and the purified product may be lyophilized.

13) Preparation of [Amino-(ethoxy-phenyl-phosphinoyl)-methyl]-phosphonic acid diethyl ether (9d) and [Amino-(hydroxy-phenyl-phosphinoyl)-methyl]-phosphonic acid (9e)

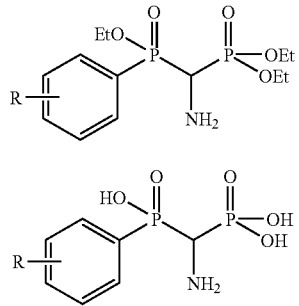

Step 1: [Azido-(ethoxy-phenyl-phosphinoyl)-methyl]-phosphonic acid diethyl ester (9b)

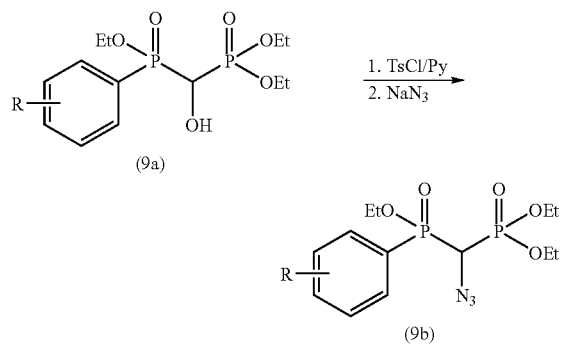

Compound 9b may be obtained from tosylation of [Hydroxy-(hydroxy-phenyl-phosphinoyl)-methyl]-phosphonic acid (9a) (e.g., TsCl/Py), followed by displacement of the resulting tosylate intermediate with sodium azide.

Step 2: [Amino-(ethoxy-phenyl-phosphinoyl)-methyl]-phosphonic acid diethyl ether (9d) and [Amino-(hydroxy-phenyl-phosphinoyl)-methyl]-phosphonic acid (9e)

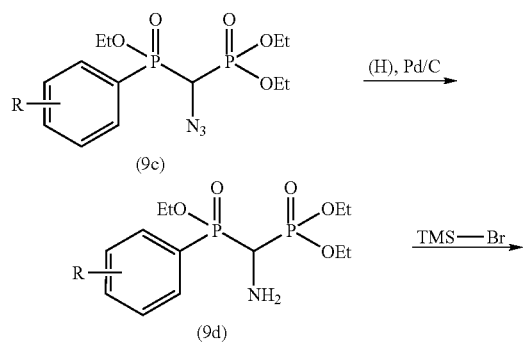

-continued

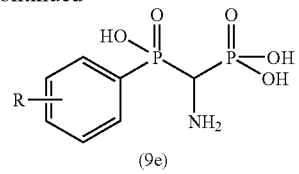

Azido intermediate (9c) may be converted to the corresponding amino intermediate (9d) by catalytic hydrogenation. Upon hydrolysis of the phosphinoyl ethyl ester moieties, compound (9e) may be obtained. The residue may be dissolved in a mixture CH₃CN/H₂O and filtered through a 0.45 μm syringe filter. The resulting solution may be purified by RP HPLC and the purified product may be lyophilized.

14) Preparation of [(Ethoxy-pyridin-2-yl-phosphinoyl)-hydroxy-methyl]-phosphonic acid diethyl ester (10c) and [Hydroxy-(hydroxy-pyridin-2-yl-phosphinoyl)-methyl]-phosphonic acid (10d)

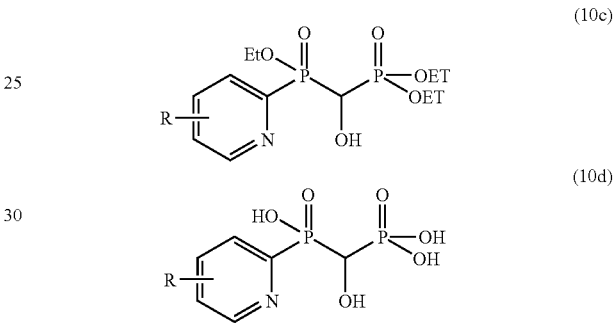

Preparation of [(Ethoxy-pyridin-2-yl-phosphinoyl)-hydroxy-methyl]-phosphonic acid diethyl ester (10c)

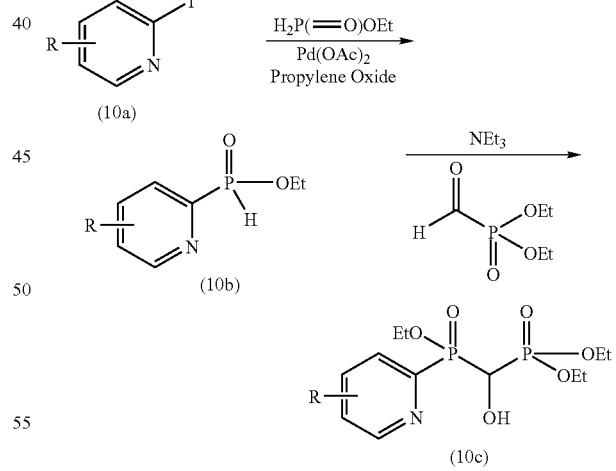

Ref: Synthesis, 1992, p. 1255

Reaction of 2-iodo-pyridine (10a) with H₂P(=O)Et in the presence of Pd(OAc)₂ in a suitable solvent (e.g., propylene oxide) yields pyridin-2-yl-phosphinic acid ethyl ester (10b). A reaction sequence similar to that described for the preparation of compound (7c) may be followed to obtain compound (10c). For example, pyridin-2-yl-phosphinic acid ethyl ester may be reacted with formyl-phosphinic acid diethyl ester in the presence of triethylamine. After allowing the reaction to proceed at room temperature for 20 hours (or until HPLC indicates that the reaction is complete), excess triethylamine may be removed under high vacuum. The residue may be dissolved in a mixture CH$_3$CN/H$_2$O and filtered through a 0.45 μm syringe filter. The resulting solution may be purified by RP HPLC and the purified product may be lyophilized.

Preparation of [Hydroxy-(hydroxy-pyridin-2-yl-phosphinoyl)-hydroxy-methyl]-phosphonic acid (10d)

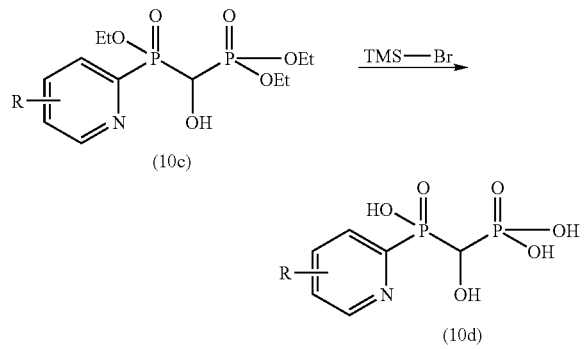

A reaction sequence similar to that described for the preparation of compound (7d) may be followed. For example, a mixture of [(Ethoxy-pyridin-2-yl-phosphinoyl)-hydroxy-methyl]-phosphonic acid diethyl ester (10c) and a suitable acid (e.g., concentrated HCl or TMS-Br) may be refluxed (120° C.) for ~20 hours (or until HPLC indicates that all of compound xxii has hydrolyzed). Excess HCl may be removed under a stream of N$_2$ at 100° C., and the residue may be further dried under high vacuum. The residue may be dissolved in a mixture CH$_3$CN/H$_2$O and filtered through a 0.45 μm syringe filter. The resulting solution may be purified by RP HPLC and the purified product may be lyophilized.

15) Preparation of [Amino-(ethoxy-pyridin-2-yl-phosphinoyl)-methyl]-phosphonic acid diethyl ether (11b) and [Amino-(hydroxy-pyridin-2-yl-phosphinoyl)-methyl]-phosphonic acid (11c)

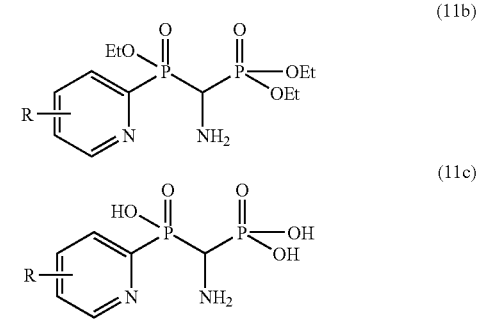

Step 1: [Azido-(ethoxy-pyridin-2-yl-phosphinoyl)-methyl]-phosphonic acid diethyl ester (11a)

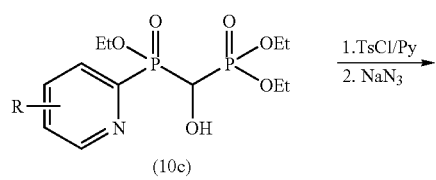

-continued

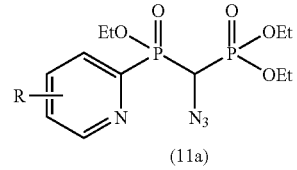

Compound (11a) may be obtained from tosylation of [(Ethoxy-pyridin-2-yl-phosphinoyl)-hydroxy-methyl]-phosphonic acid diethyl ester (10c) (e.g., TsCl/Py), followed by displacement of the resulting tosylate intermediate with sodium azide.

Step 2: [Amino-(ethoxy-pyridin-2-yl-phosphinoyl)-methyl]-phosphonic acid diethyl ether (11b) and [Amino-(hydroxy-pyridin-2-yl-phosphinoyl)-methyl]-phosphonic acid 11c)

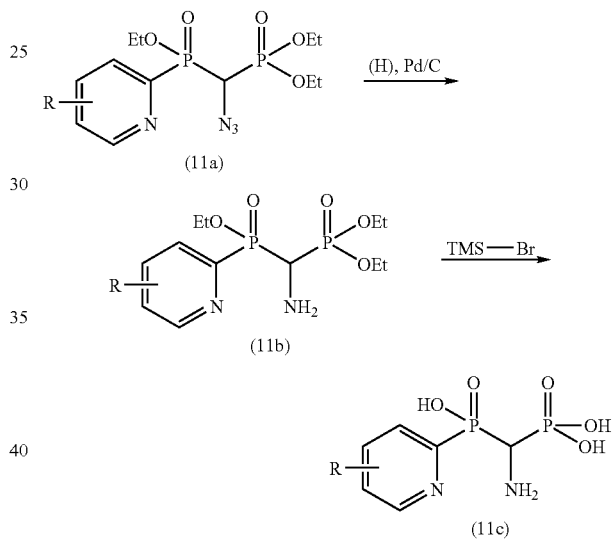

Azido intermediate (11a) may be converted to the corresponding amino intermediate (11b) by catalytic hydrogenation. Upon hydrolysis of the phosphinoyl ethyl ester moieties, compound (11c) may be obtained. The residue may be dissolved in a mixture CH$_3$CN/H$_2$O and filtered through a 0.45 μm syringe filter. The resulting solution may be purified by RP HPLC and the purified product may be lyophilized.

16) Preparation of [(Ethoxy-pyridin-2-yl-phosphinoyl)-hydroxy-methyl]-acetic acid ethyl ester (12c) and Hydroxy-(hydroxy-pyridin-2-yl-phosphinoyl)-acetic acid (12d)

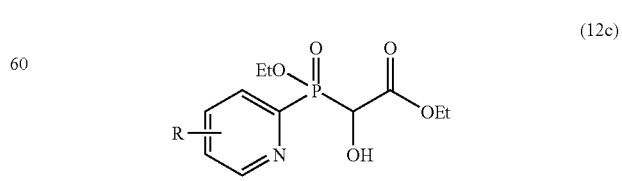

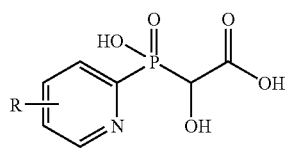

(12d)

Preparation of [(Ethoxy-pyridin-2-yl-phosphinoyl)-hydroxy-methyl]-acetic acid ethyl ester (12c)

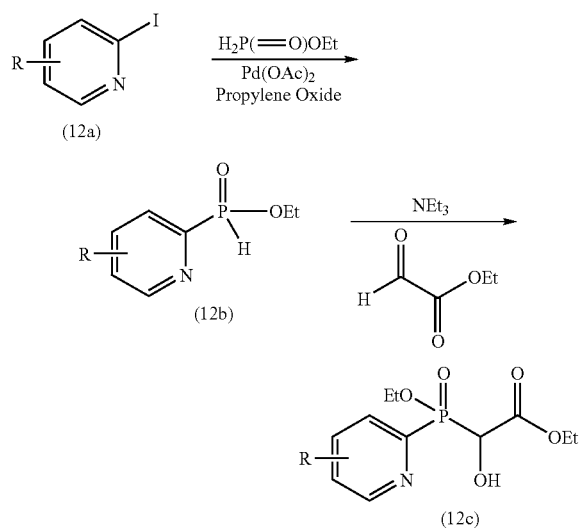

Ref: Synthesis, 1992, p. 1255

Reaction of 2-iodo-pyridine (12a) with H₂P(=O))Et in the presence of Pd(OAc)₂ in a suitable solvent (e.g., propylene oxide) yields pyridin-2-yl-phosphinic acid ethyl ester (12b). A reaction sequence analogous to that described for the preparation of compound (7c) may be followed to obtain compound (12c). For example, pyridin-2-yl-phosphinic acid ethyl ester (12b) may be reacted with Oxo-acetic acid ethyl ester in the presence of triethylamine. After allowing the reaction to proceed at room temperature for ~20 hours (or until HPLC indicates that the reaction is complete), excess triethylamine may be removed under high vacuum. The residue may be dissolved in a mixture CH₃CN/H₂O and filtered through a 0.45 μm syringe filter. The resulting solution may be purified by RP HPLC and the purified product may be lyophilized.

Preparation of [(Ethoxy-pyridin-2-yl-phosphinoyl)-hydroxy-methyl]-acetic acid (12d)

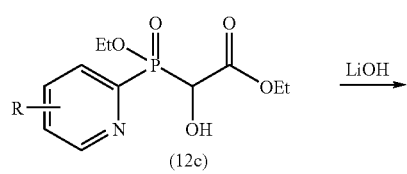

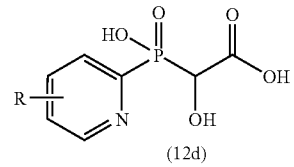

(12d)

Compound 12d may be obtained by hydrolysis of ethyl ester 12c. The residue may be dissolved in a mixture CH₃CN/H₂O and filtered through a 0.45 μm syringe filter. The resulting solution may be purified by RP HPLC and the purified product may be lyophilized.

17) Preparation of [Amino-(ethoxy-pyridin-2-yl-phosphinoyl)-methyl]-acetic acid ethyl ester (13b) and [Amino-(hydroxy-pyridin-2-yl-phosphinoyl)-methyl]-acetic acid (13c

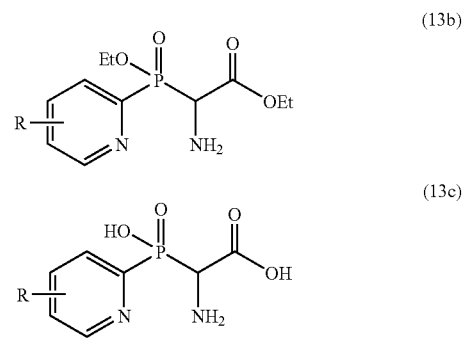

Step 1: [Azido-(ethoxy-pyridin-2-yl-phosphinoyl)-methyl]-acetic acid ethyl ester (13a)

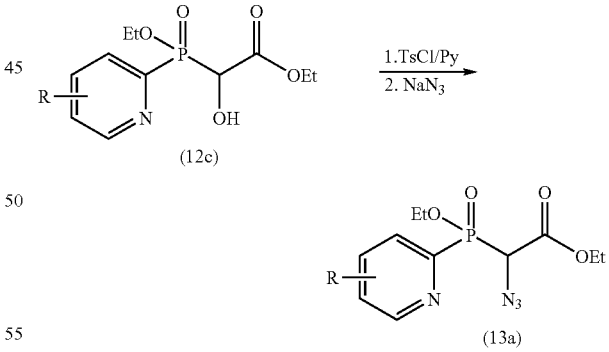

Compound 13a may be obtained from tosylation of [(Ethoxy-pyridin-2-yl-phosphinoyl)-hydroxy-methyl]-phosphonic acid diethyl ester (12c) (e.g., TsCl/Py), followed by displacement of the resulting tosylate intermediate with sodium azide.

Step 2: [Amino-(ethoxy-pyridin-2-yl-phosphinoyl)-methyl]-acetic acid ethyl ester (13b) and [Amino-(hydroxy-pyridin-2-yl-phosphinoyl)-methyl]-acetic acid (13c)

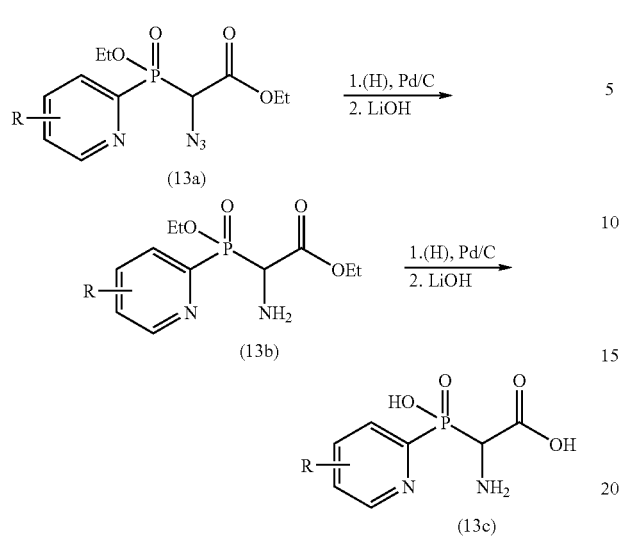

(13a)

(13b)

(13c)

Azido intermediate 13a may be converted to the corresponding amino intermediate (13b) by catalytic hydrogenation. Upon hydrolysis of the phosphinoyl ethyl ester and ethyl acetate moieties, compound (13c) may be obtained. The residue may be dissolved in a mixture $CH_3CN/H_2O$ and filtered through a 0.45 μm syringe filter. The resulting solution may be purified by RP HPLC and the purified product may be lyophilized.

18) Preparation of meta-oriented aryl-PCM of Structure Z

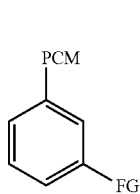

Z wherein FG is a functional group (or latent functional group) suitable for incorporation (via covalent linkage) of the aryl-PCM moiety into the structure of the compounds of the invention. It will be appreciated that the term "latent functional group" means a precursor functionality that is chemically transformed (through deprotection of chemical derivatization) to give the functional group suitable for attachment of the aryl-PCM onto the inventive constructs.

a. Preparation of [[(3-aminophenyl)hydroxyphosphinyl]methyl]-Phosphonic acid 14e:

The synthesis of compound 14e and an exemplary synthetic protocol are detailed below:

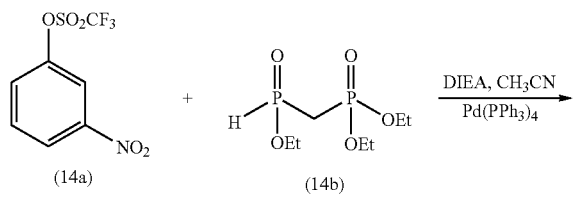

(14a)  (14b)

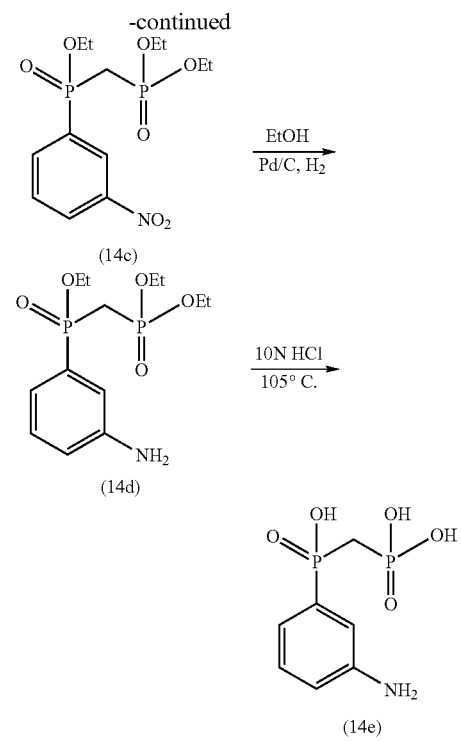

(14c)

(14d)

(14e)

Step 1: Phosphonic acid, [[(3-nitrophenyl)ethoxyphosphinyl]methyl]-, diethyl ester (14c):

(14c)

A solution of trifluoromethanesulfonic acid, 3-nitrophenyl ester (14a) (27.2 g, 100 mmol) and phosphonic acid, [(ethoxyphosphinyl)methyl]-, diethyl ester (14b) (24.4 g, 100 mmol), and diisopropylethylamine (DIEA, 26.1 mL, 150 mmol) in acetonitrile (150 mL) was purged with Argon (bubbled) for 10 min. after which time tetrakis(triphenylphosphine) palladium (0) catalyst (5.8 g, 5 mol %) was added. The reaction mixture was then heated at reflux for 8 hr, after which time the reaction mixture was allowed to cool, filtered with the aid of EtOAc, and evaporated to an oil. The crude material was then dissolved in $CH_2Cl_2$ (500 mL), washed with a saturated solution of $NaHCO_3$ (2×100 mL), dried over $MgSO_4$, filtered, and evaporated. Crude material was purified by chromatography (silica gel, 5% MeOH/$CH_2Cl_2$) to afford product 14c (21.3 g, 58%) as an oil: TLC (5% MeOH/$CHCl_3$) Rf=0.33; $^{31}P$ NMR ($CDCl_3$, 75 MHz) 31.0, 18.6; $^1H$ NMR ($CDCl_3$, 300 MHz) 8.70 (dt, J=12.9 and 1.5 Hz, 1H), 8.43 (dt, J=8.2 and 1.1 Hz, 1H), 8.24 (dd, J=11.7 and 7.6 Hz, 1H), 7.76–7.71 (m, 1H), 4.29–3.97 (m, 6H), 2.75–2.62 (m, 2H), 1.38 (t, J=7.1 Hz, 3H), 1.31 (t, J=7.1 Hz, 3H), 1.22 (t, J=7.1 Hz, 3H); $^{13}C$ NMR ($CDCl_3$, 75 MHz) 148.4 (d, J=15 Hz), 138.3 (d, J=11 Hz), 133.9 (d, J=135 Hz), 130.1 (d, J=14 Hz), 127.5–127.1 (m), 63.1–62.4

(m), 29.9 (d, J=136 and 94 Hz), 16.8–16.5 (m); LRMS (ES+): (M+H)+ 366; (ES-): (M-H)- 364.

Step 2: Phosphonic acid, [[(3-aminophenyl)ethoxyphosphinyl]methyl]-, diethyl ester (14d):

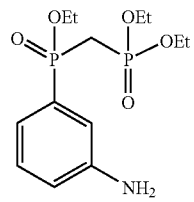

(14d)

A solution of phosphonic acid, [[(3-nitrophenyl) ethoxyphosphinyl]methyl]-, diethyl ester (14c) (21.0 g, 57.5 mmol) in EtOH (150 mL) was treated with activated carbon (10 g) and the resulting suspension stirred for 3 h. After this time the mixture was filtered through a pad of Celite and the filter cake washed with EtOH (50 mL). The combined filtrates were transferred to a hydrogenation flask, 10% palladium on carbon catalyst (3.0 g) added, and the solution purged with Argon (bubbled) for 5 min. The reaction mixture was then hydrogenated at 60–80 psi $H_2$ for 20 h, after which time the reaction mixture was filtered through a pad of Celite and the filter cake washed with EtOH (~100 mL). The combined filtrates were evaporated to provide oil which was purified by chromatography (silica gel, 6% MeOH/$CH_2Cl_2$) to afford product 14d (13.4 g, 70%) as an oil: TLC (5% MeOH/$CHCl_3$) Rf=0.24; $^{31}P$ NMR ($CDCl_3$, 75 MHz) 34.4, 19.9; $^1H$ NMR ($CDCl_3$, 300 MHz) 7.27–7.10 (m, 3H), 6.85 (dd, J=7.9 and 0.8 Hz, 1H), 4.19–3.89 (m, 8H), 2.67–2.53 (m, 2H), 1.34–1.19 (m, 9H); $^{13}C$ NMR ($CDCl_3$, 75 MHz) 147.4 (d, J=16 Hz), 131.8 (d, J=134 Hz), 129.8 (d, J=15 Hz), 121.1 (d, J=11 Hz), 119.2 (d, J=3 Hz), 118.1 (d, J=11 Hz), 62.9–61.6 (m), 29.7 (d, J=134 and 91 Hz), 16.8–16.5 (m); LRMS (ES+): (M+H)+ 334; (ES-): (M-H)- 336.

Step 3: [[(3-aminophenyl)hydroxyphosphinyl]methyl]-Phosphonic acid (14e):

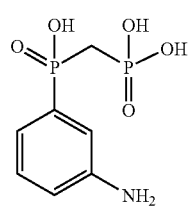

(14e)

A solution of phosphonic acid, [[(3-aminophenyl)ethoxyphosphinyl]methyl]-, diethyl ester (14d) (10.0 g, 29.8 mmol) in a 10 N aqueous solution of HCl (32 mL) was heated in a sealed tube at 105 C for 48 h. After this time the mixture was evaporated to afford product 14e as a viscous oil: $^{31}P$ NMR ($D_2O$/HCl, 75 MHz) 33.0, 20.3; $^1H$ NMR ($D_2O$/HCl, 300 MHz) 7.17–7.12 (m, 2H), 6.99 (br, s, 2H), 2.09 (dd, J=20.6 and 17.4 Hz, 1H); $^{13}C$ NMR ($D_2O$/HCl, 75 MHz) 134.2 (d, J=137 Hz), 131.8 (d, J=11 Hz), 130.8 (d, J=14 Hz), 130.2 (d, J=17 Hz), 127.4, 125.5 (d, J=12 Hz), 30.0 (d, J=129 and 30 Hz); LRMS (ES+): (M+H)+ 252; (ES-): (M-H)- 250.

19) Preparation of Hydroxy-(hydroxy-phenyl-phosphinoyl)-acetic acid (15a)

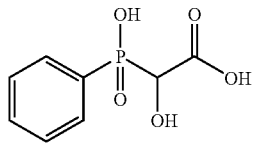

(15a)

Step 1: (Ethoxy-phenyl-phosphinoyl)-hydroxy-acetic acid ethyl ester

To a solution of ethylphenylphosphinate (0.5 g, 2.94 mmol) in 5 mL of anhydrous toluene and anhydrous triethylamine (0.17 mL, 1.18 mmol) under argon was added 0.68 g (2.94 mmol) of a 50% (w/w) glyoxylic acid solution in toluene. The mixture was stirred for 16 h at room temperature, at which point the solvent was removed in vacuo. The crude material was purified by flash chromatography on silica gel. Elution with 100% ethylacetate afforded 383 mg (48%) of the desired compound.

Step 2: Hydroxy-(hydroxy-phenyl-phosphinoyl)-acetic acid (15a)

To a solution of (ethoxy-phenyl-phosphinoyl)-hydroxyacetic acid ethyl ester (382 mg, 1.41 mmol) in 10 mL of 6 M HCl was heated to reflux overnight. The resulting mixture was concentrated to a minimum volume and lyophilized affording a pale yellow solid (274 mg, 90%)

20) Preparation of Phosphorus-containing Imidazole Moieties

The following two sections a) and b) detail exemplary synthetic approaches for the preparation of Phosphorus-containing imidazole moieties. One of ordinary skill in the art, in light of the teachings herein and synthetic methods know in the art, will appreciate that a variety of analogues and/or derivatives of such P-containing imidazole moieties may be prepared.

a) Preparation of Compound 16e

The scheme below describes an exemplary synthetic approach for the preparation of compound 16e:

109

-continued

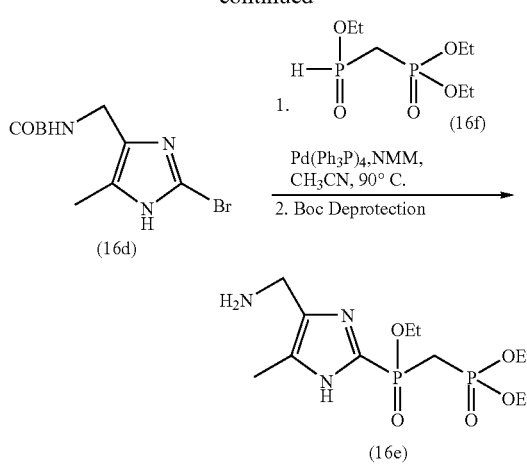

For example, imidazolyl alcohol 16a may be converted to the corresponding halide 16b by reaction with $SO_2Cl_2$ in a suitable solvent (e.g., CH2Cl2). Reaction of 16b with ammonia, followed by Boc protection of the resulting amine moiety yields Boc-amino compound 16c. Bromination of the imidazole ring may be accomplished by reaction with NBS in a suitable solvent (e.g., THF) to give compound 16d. The desired Phosphorus-containing imidazole derivative may be obtained by reaction of 16d with Ethoxyphosphinoylmethyl-phosphonic acid diethyl ester (16f) in the presence of $Pd(PPh_3)_4$, followed by Boc deprotection. One of ordinary skill in the art will appreciate that the corresponding imidazolyl phosphonic acid moiety is readily available by hydrolysis of 16e.

b) Preparation of Compound 17a

The scheme below describes an exemplary synthetic approach for the preparation of compound 17b:

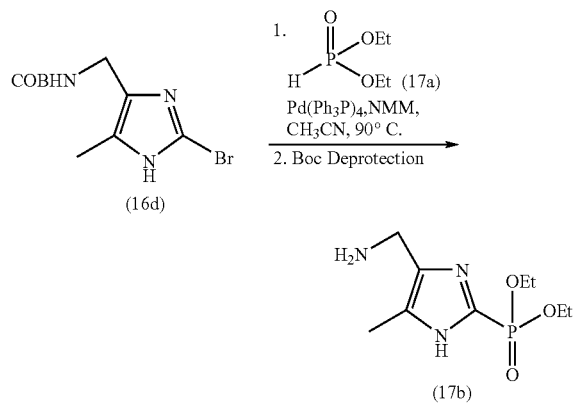

For example, Reaction of Boc-protected imidazole compound 16d with phosphorus reagent 17a in the presence of $Pd(PPh_3)_4$, followed by Boc deprotection yields the desired imidazolyl phosphinoyl diethyl ether derivative (17b). One of ordinary skill in the art will appreciate that the corresponding imidazolyl phosphonic acid moiety is readily available by hydrolysis of 17b.

110

B) Preparation of Exemplary Quinolinone Compounds:

1) Preparation of Exemplary Quinolinones Having the General Structure A:

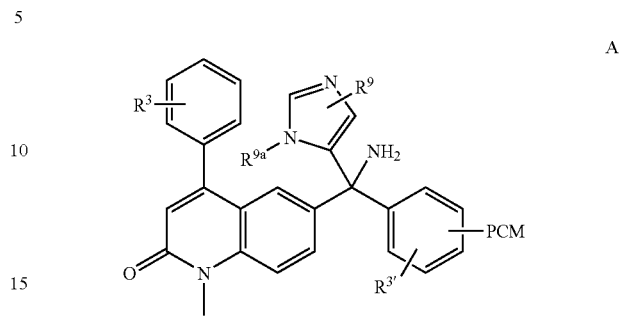

a) Scheme 4 depicts the synthesis of certain exemplary compounds having the general structure B, wherein Y, $R^1$, $R^3$, $R^{3'}$, $R^9$ and $R^{9a}$ are as disclosed in classes and subclasses described herein (e.g., in the description of $R^B$ and $R^D$, or specific substituents, as further defined herein for $R^B$ and $R^D$).

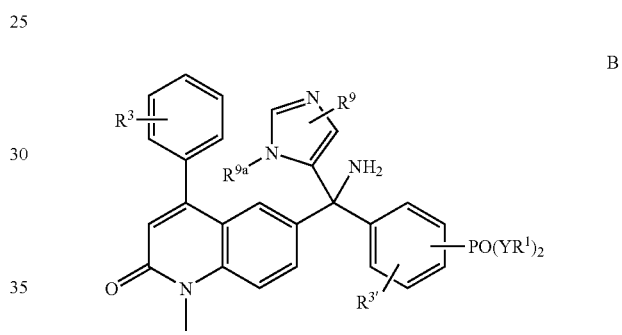

For example, the phosphorus-containing moiety may be $-PO(R_1)_2$ where Y is a chemical bond linking $R^1$ to P and $R^1$ is alkyl or aryl (phosphine oxide moiety). Alternatively, Y is O and $R^1$ is alkyl or aryl (phosphonate moiety). Thus, 4-nitrophenyl acid chloride (1) may be reacted with organozinc reagent (2) to yield phosphorus-containing diphenyl ketone (3) (see Rieke et al., *J. Org. Chem.*, 56:1445–1453, 1991). Protection of compound 3 with ethan-1,2-diol gives dioxolane intermediate 4, which can be converted to the desired quinolinone B in several steps. With respect to the synthetic transformations of dioxolane 4 leading to the formation of compound B, an exemplary synthetic protocol may be found in Venet et al., WO 97/21701. Other synthetic methodologies for the preparation of analogues and derivatives of quinolinone B will be readily apparent to the person of ordinary skill in the art.

Scheme 4

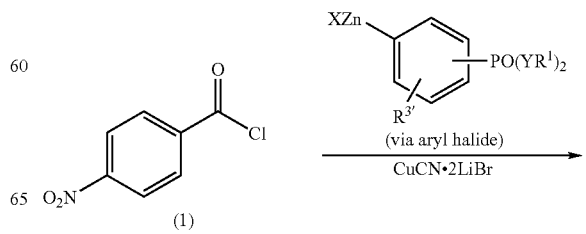

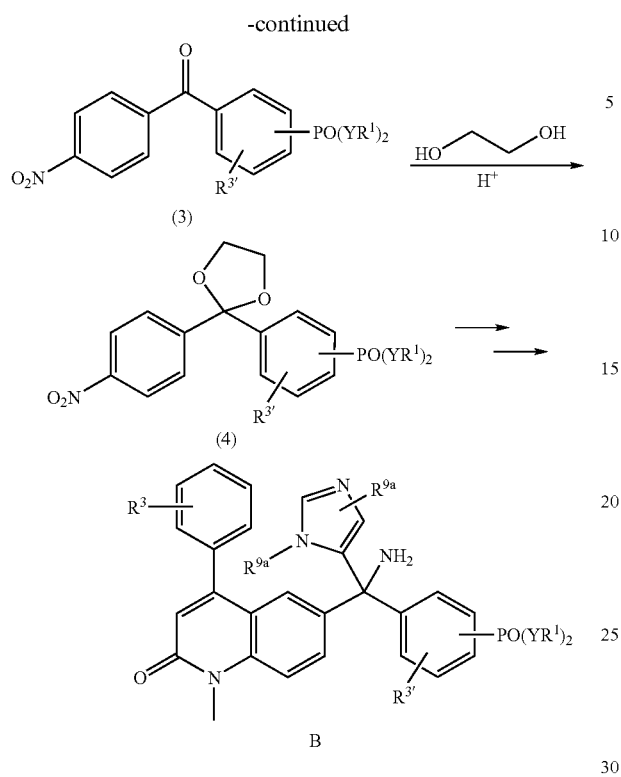
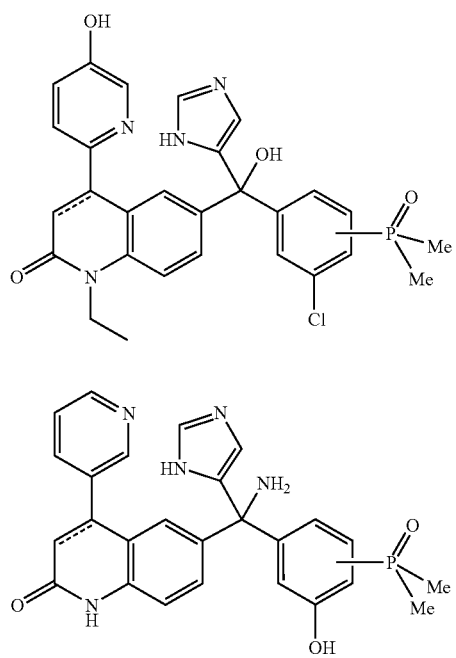
Exemplary compounds prepared according to this method include, but are not limited to:
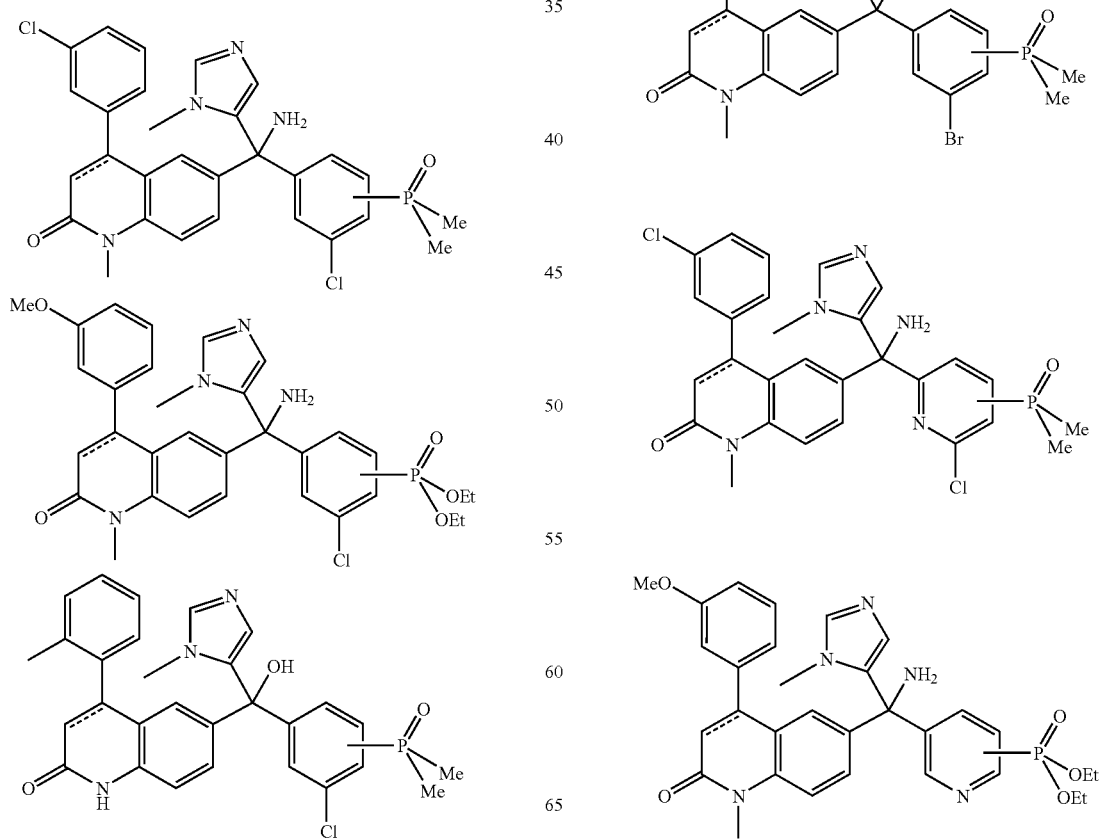

-continued

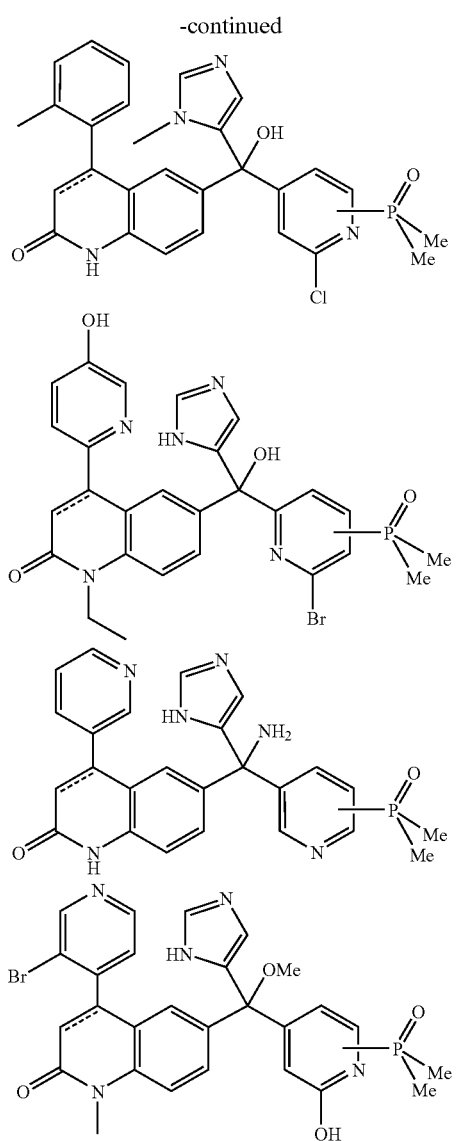

b) Scheme 5 depicts the synthesis of certain exemplary compounds having the general structure C, wherein Y, $R^1$, $R^3$, $R^{3'}$, $R^9$ and $R^{9a}$ are disclosed in classes and subclasses described herein (e.g., in the description of $R^B$ and $R^D$, or specific substituents, as further defined herein for $R^B$ and $R^D$).

C

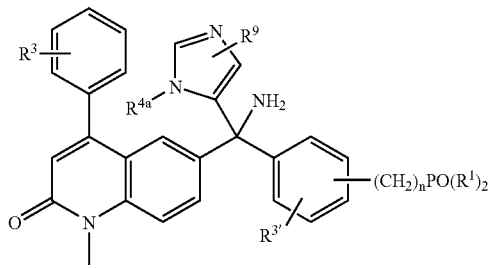

For example, the phosphorus-containing moiety $-(CH_2)_n-PO(YR^1)_2$ may be an alkyl phosphine oxide moiety where Y is a chemical bond linking $R^1$ to P and $R^1$ is alkyl or aryl. Alternatively, Y may be O and $R^1$ may be, for example, alkyl or aryl, and the phosphorus-containing moiety comprises an alkyl phosphonate group. Thus, coupling of protected phenyl carboxylic acid 9 with alkyl phosphine oxide (or phosphonate) zinc reagent 10 yields the corresponding phosphorus-containing phenyl carboxyl compound 11 (for exemplary experimental protocols, see Rieke et al., *J. Org. Chem.*, 56:1445–1453, 1991; Yokomatsu et al., *Tetrahedron*, 53:815–822, 1997; and Weigele et al., PCT/US00/34417 and PCT/US97/40653). After deprotection of the carboxylic moiety, followed by acid chloride formation, the resulting acid chloride 12 can be coupled with 4-nitrophenyl organozinc reagent 13 to yield a phosphorus-containing diphenylketone intermediate (for exemplary experimental protocols, see Rieke et al., *J. Org. Chem.*, 56:1445–1453, 1991). Dioxolane compound 14 may be obtained by protection of the diphenylketone with ethan-1, 2-diol, and can then be converted to the desired quinolinone C in several steps. With respect to the synthetic transformations of dioxolane 14 leading to the formation of compound C, an exemplary synthetic protocol may be found in Venet et al., WO 97/21701 and U.S. Pat. No. 6,169,096. Other synthetic methodologies for the preparation of analogues and derivatives of quinolinone C will be readily apparent to the person of ordinary skill in the art.

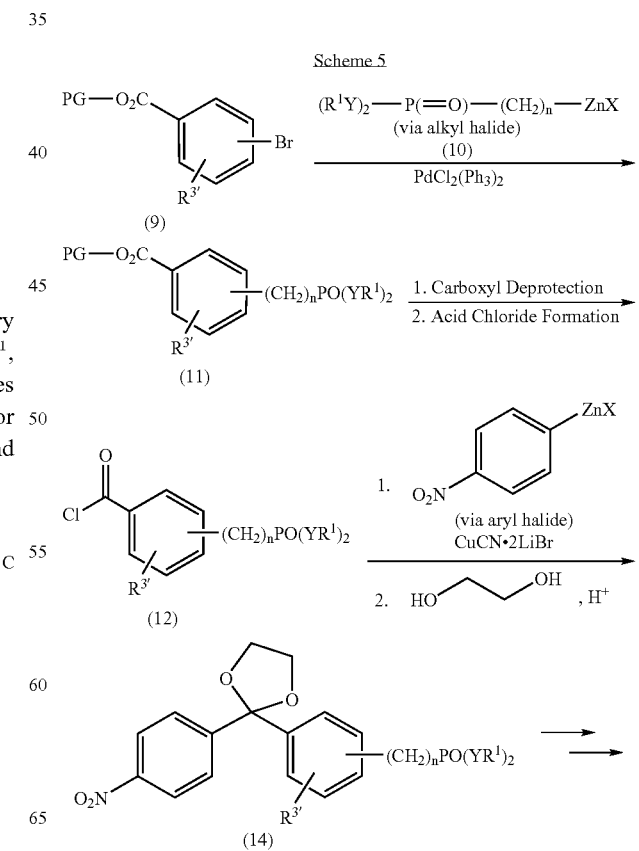

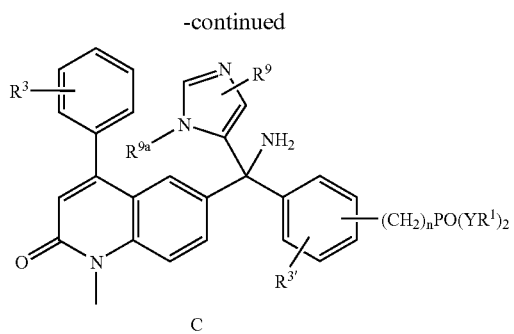
C
Exemplary compounds prepared according to this method include, but are not limited to:
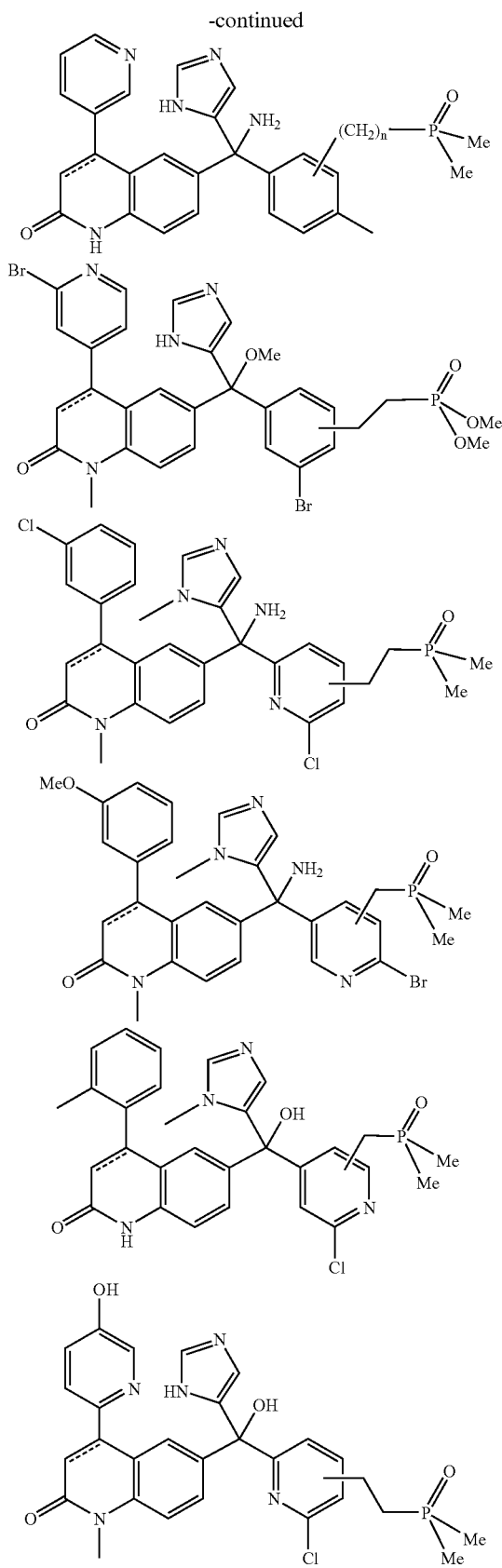

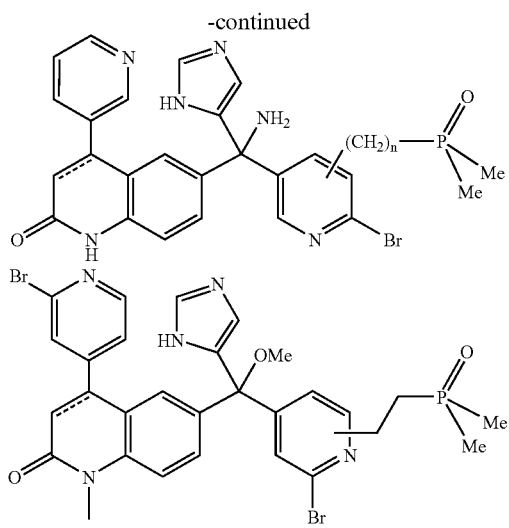

2) Preparation of Exemplar Quinolinones Having the General Structure D:

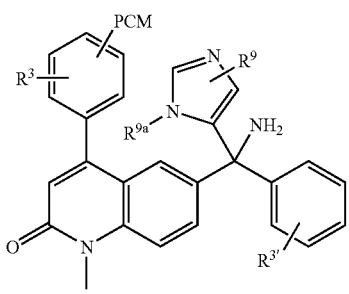

a) Scheme 6 depicts the synthesis of certain exemplary compounds having the general structure E, wherein Y, $R^1$, $R^3$, $R^{3'}$, $R^9$ and $R^{9a}$ are as disclosed in classes and subclasses described herein (e.g., in the description of $R^B$ and $R^D$, or specific substituents, as further defined herein for $R^B$ and $R^D$).

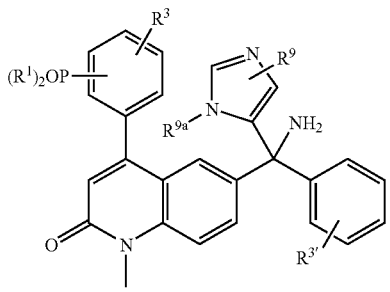

For example, the phosphorus-containing moiety —PO(YR1)$_2$ may be an aryl phosphine oxide moiety where Y is a chemical bond linking $R^1$ to P and $R^1$ is alkyl or aryl. Alternatively, Y may be O and $R^1$ may be, for example, alkyl or aryl, and the phosphorus-containing moiety comprises an aryl phosphonate group. Thus, phosphorylated bromobenzene 16 may be reacted with zinc bromide reagent 15 to give the corresponding adduct 17. Reaction of cyano compound 17 with dioxolane 18 in the presence of a base (e.g., NaOH) in a suitable solvent, such as an alcohol (e.g., MeOH) yields isoxazole 19, which can in turn be converted to the desired quinolinone E in several steps. With respect to the synthetic transformations of isoxazole 19 leading to the formation of compound E, an exemplary synthetic protocol may be found in Venet et al., WO 97/21701. Other synthetic methodologies for the preparation of analogues and derivatives of quinolinone E will be readily apparent to the person of ordinary skill in the art.

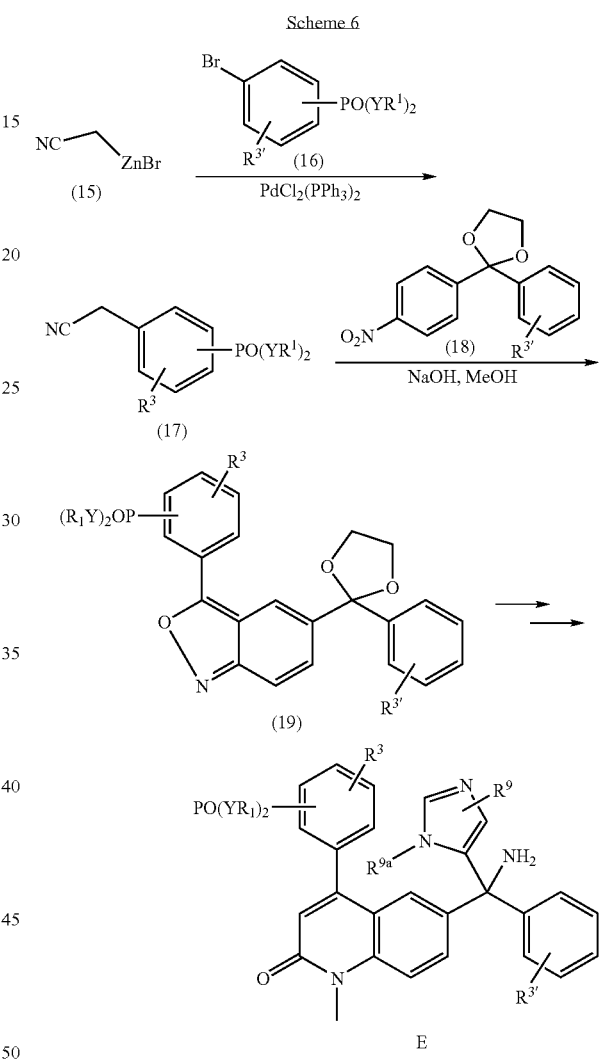

Exemplary compounds prepared according to this method include, but are not limited to:

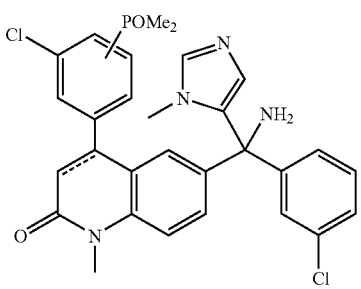

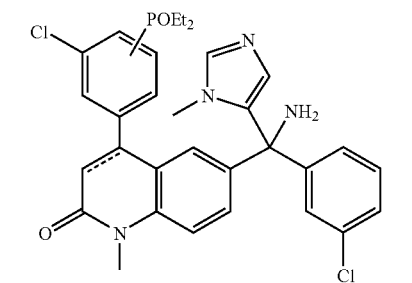
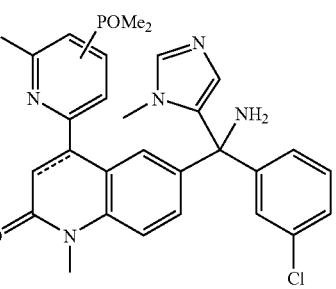
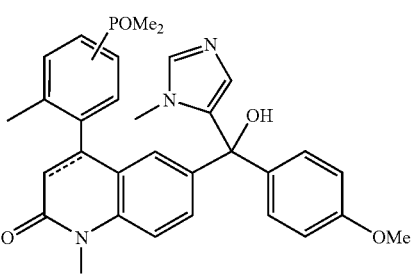
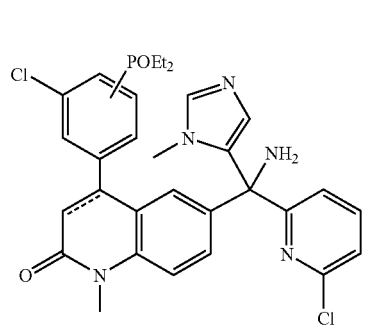
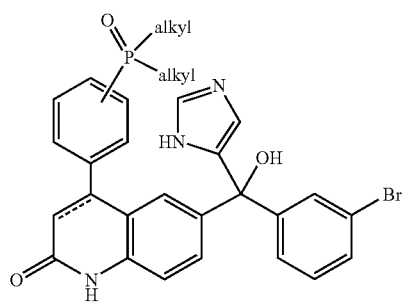
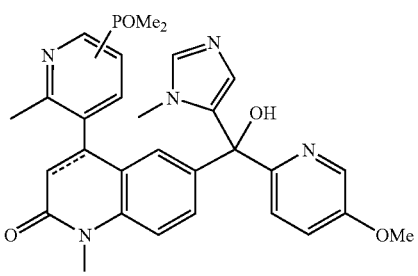
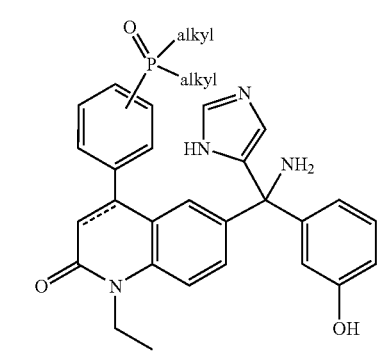
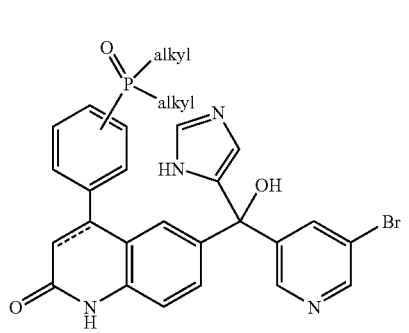
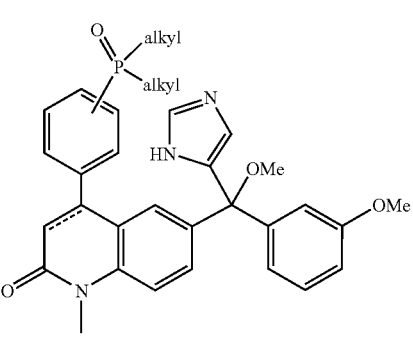
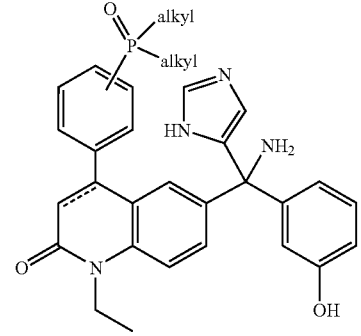

-continued

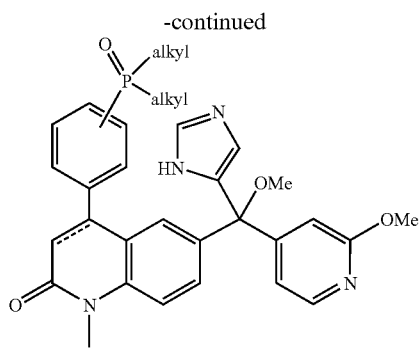

b) Scheme 7 depicts the synthesis of certain exemplary compounds having the general structure F, wherein Y, $R^1$, $R^3$, $R^{3'}$, $R^9$ and $R^{9a}$ are as disclosed in classes and subclasses described herein (e.g., in the description of $R^B$ and $R^D$, or specific substituents, as further defined herein for $R^B$ and $R^D$).

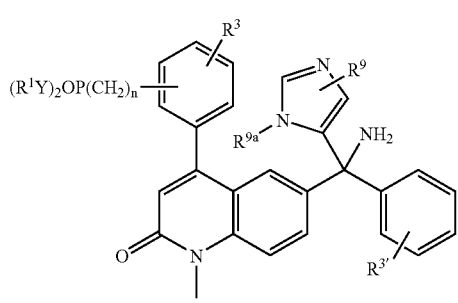

F

For example, the phosphorus-containing moiety $-(CH_2)_n-PO(YR^1)_2$ may be an alkyl phosphine oxide moiety where Y is a chemical bond linking P to $R^1$, and $R^1$ is alkyl or aryl. Alternatively, Y may be O and $R^1$ may be, for example, alkyl or aryl, and the phosphorus-containing moiety comprises an alkyl phosphonate group. Thus, coupling of bromo benzyl cyanide 20 with alkyl phosphine oxide (or phosphonate) zinc reagent 21 yields the corresponding phosphorus-containing benzyl cyanide 22 (for exemplary experimental protocols, see Rieke et al., *J. Org. Chem.*, 56:1445–1453, 1991; Yokomatsu et al., *Tetrahedron*, 53:815–822, 1997; and Weigele et al., PCT/US00/34417 and PCT/US97/40653). Reaction of cyano compound 22 with dioxolane 18 in the presence of a base (e.g., NaOH) in a suitable solvent, such as an alcohol (e.g., MeOH) yields isoxazole 23, which can in turn be converted to the desired quinolinone F in several steps. With respect to the synthetic transformations of isoxazole 23 leading to the formation of compound F, an exemplary synthetic protocol may be found in Venet et al., WO 97/21701. Other synthetic methodologies for the preparation of analogues and derivatives of quinolinone F will be readily apparent to the person of ordinary skill in the art.

Scheme 7

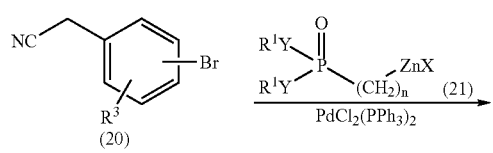

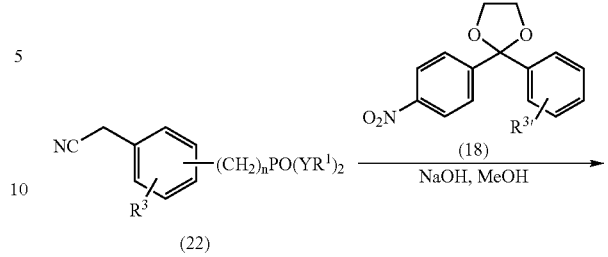

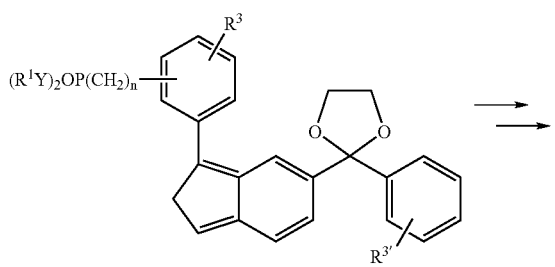

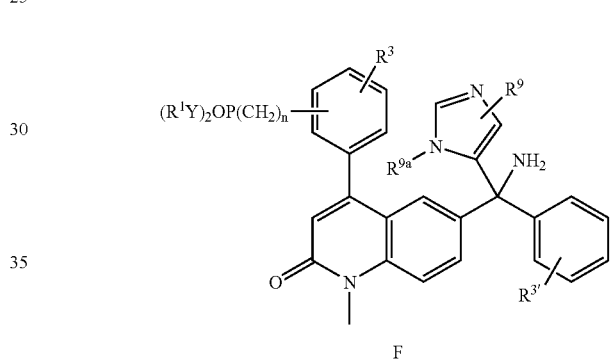

F

Exemplary compounds prepared according to this method include, but are not limited to:

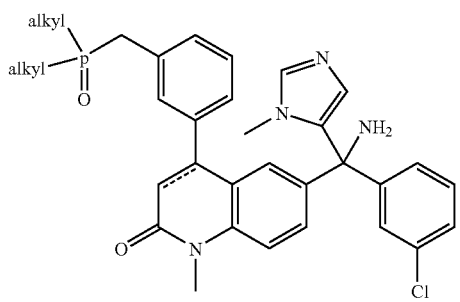

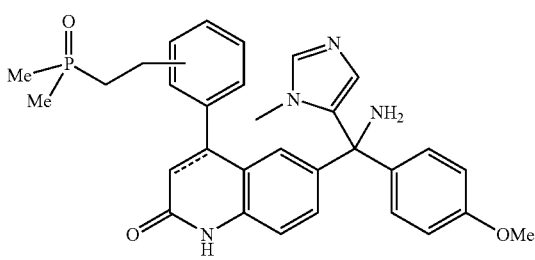

-continued

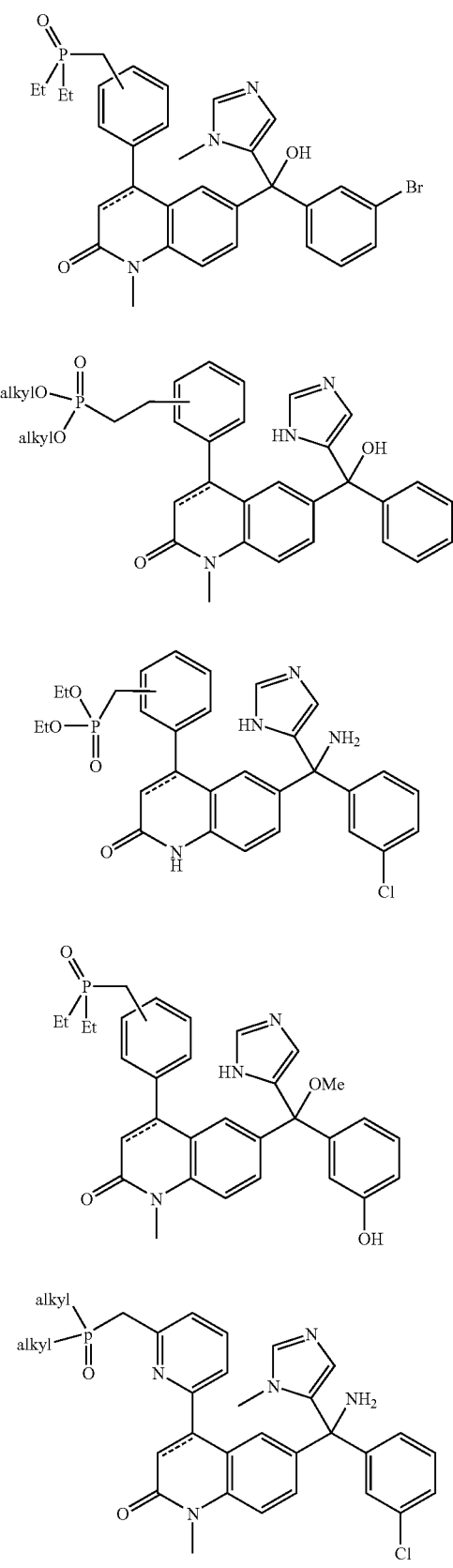
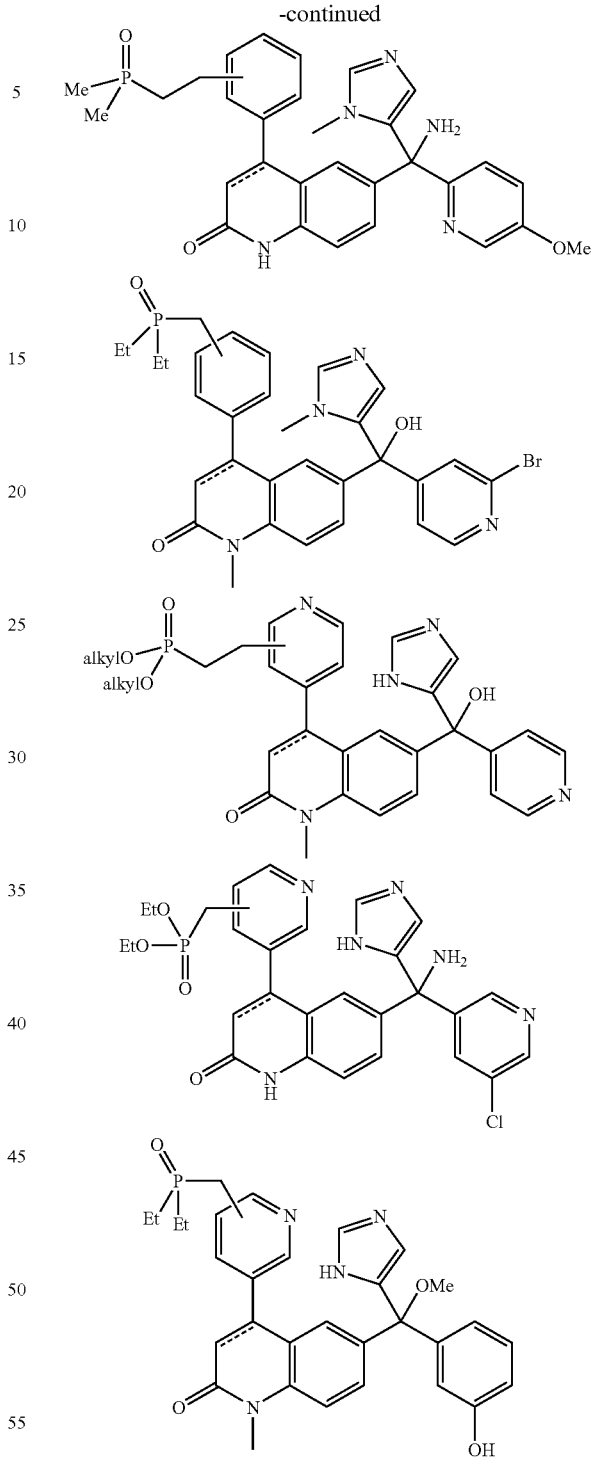

The synthetic methods described above are summarized and exemplified further in Scheme 8 below.

In Addition, it will be appreciated that the above-described methods may be used in combination to prepare quinolinones having two or more phosphorus-containing moieties.

Preparation of phosphorus-containing (imidazol-5-yl)methyl-2-quinolinones (R=alkyl, aryl, alkoxy, aryloxy, etc.)

Scheme 8
I.
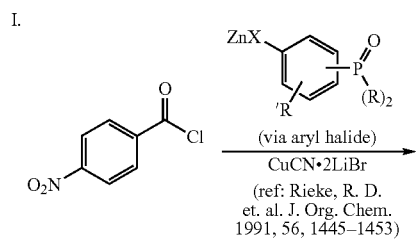
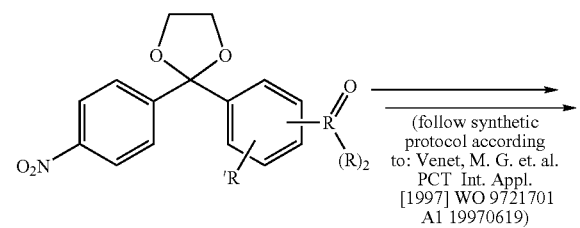
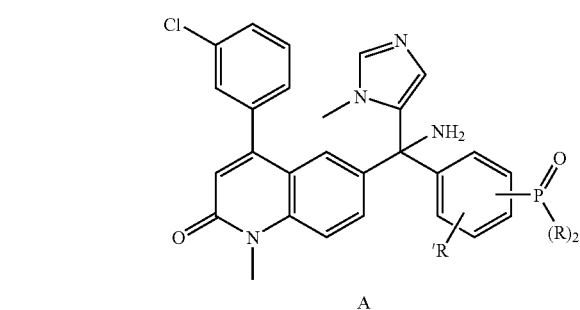
A
II.
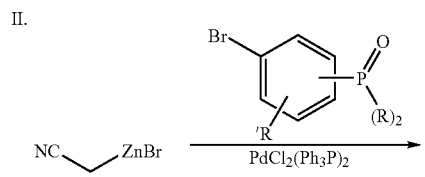
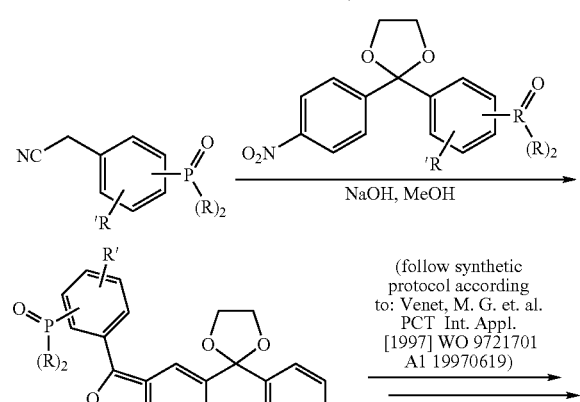
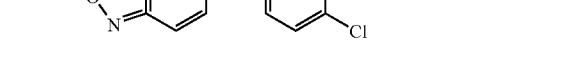
-continued
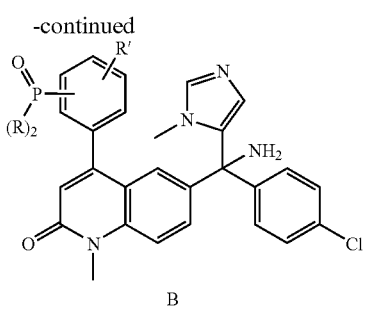
B
III.
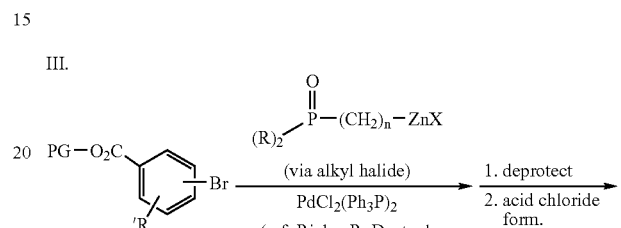
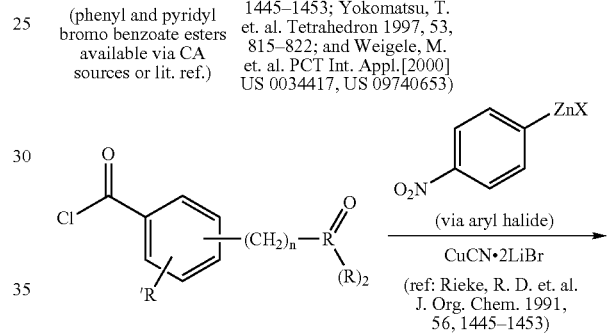
C
IV.
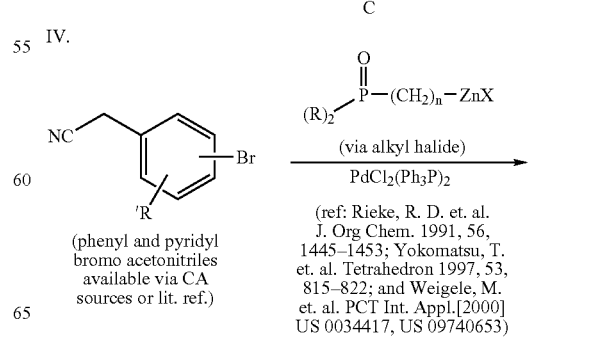

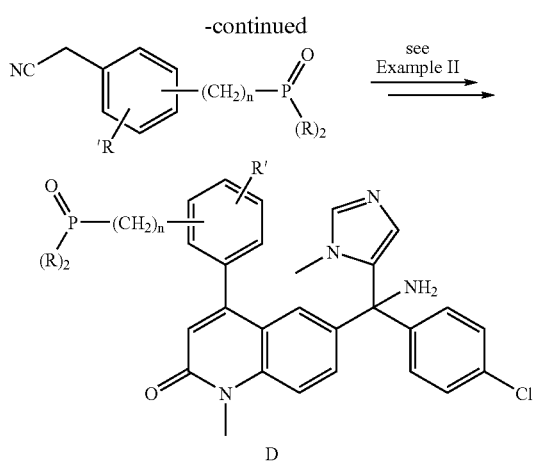

Solid Phase Synthesis and Combinatorial Libraries of Quinolinone Compounds

It will be appreciated that, in addition to preparing the inventive compounds using traditional solution phase techniques, the present invention contemplates the preparation of compounds and libraries of compounds using solid phase techniques. Thus, the desired components may be modified so that they may be attached to the solid support. The use of a solid support bound component enables the use of more rapid split and pool techniques to generate larger libraries (e.g., greater than 10,000 members) more easily. It will be appreciated that solid phase parallel synthesis techniques also can be utilized, such as those described in U.S. Pat. Nos. 5,712,171 and 5,736,412; incorporated herein by reference.

A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. Additionally, the use of a solid support also enables the use of specific encoding techniques to "track" the identity of the inventive compounds in the library. A solid support can be any material which is an insoluble matrix and can have a rigid or semi-rigid surface. Exemplary solid supports include, but are not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N-N'-bis-acryloylethylenediamine, and glass particles coated with a hydrophobic polymer. One of ordinary skill in the art will realize that the choice of particular solid support will be limited by the compatability of the support with the reaction chemistry being utilized. An exemplary solid support is a Tentagel amino resin, a composite of 1) a polystyrene bead crosslinked with divinylbenzene and 2) PEG (polyethylene glycol), is employed for use in the present invention. Tentagel is a particularly useful solid support because it provides a versatile support for use in on-bead or off-bead assays, and it also undergoes excellent swelling in solvents ranging from toluene to water.

Specific compounds may be attached directly to the solid support or may be attached to the solid support through a linking reagent. Direct attachment to the solid support may be useful if it is desired not to detach the library member from the solid support. For example, for direct on-bead analysis of biological/pharmacological activitiy or analysis of the compound structure, a stronger interaction between the library member and the solid support may be desirable. Alternatively, the use of a linking reagent may be useful if more facile cleavage of the inventive library members from the solid support is desired.

Furthermore, any linking reagent used in the present invention may comprise a single linking molecule, or alternatively may comprise a linking molecule and one or more spacer molecules. A spacer molecule is particularly useful when the particular reaction conditions require that the linking molecule be separated from the library member, or if additional distance between the solid support/linking unit and the library member is desired. In one particularly preferred embodiment, photocleavable linkers are employed to attach the solid phase resin to the component. Photocleavable linkers are advantageous because of the ability to use these linkers in in vivo screening strategies. Once the compound is released from the solid support via photocleavage, the compound is able to enter the cell. Exemplary photocleavable linkers include, but are not limited to ortho-Nitrobenzyl photolinkers and dithiane protected benzoin photolinkers. One of ordinary skill in the art will realize that the method of the present invention is not limited to the use of photocleavable linkers; rather other linkers may be employed, preferably those that are capable of delivering the desired compounds in vivo.

Thus, the synthesis of libraries of quinolinone compounds can be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., Chem. Rev. 1996, 96, 555, incorporated herein by reference.) One of ordinary skill in the art will realize that the choice of method will depend upon the specific number of compounds to be synthesized, the specific reaction chemistry, and the availability of specific instrumentation, such as robotic instrumentation for the preparation and analysis of the inventive libraries. In particularly preferred embodiments, the reactions to be performed on the inventive scaffolds to generate the libraries are selected for their ability to proceed in high yield, and in a stereoselective fashion, if applicable.

In one embodiment of the present invention, libraries are generated using a solution phase technique. Traditional advantages of solution phase techniques for the synthesis of combinatorial libraries include the availability of a much wider range of organic reactions, and the relative ease with which products can be characterized. In a preferred embodiment, for the generation of a solution phase combinatorial library, a parallel synthesis technique is utilized, in which all of the products are assembled separately in their own reaction vessels. In a particularly preferred parallel synthesis procedure, a microtitre plate containing n rows and m columns of tiny wells which are capable of holding a few milliliters of the solvent in which the reaction will occur, is utilized. It is possible to then use n variants of reactant A, and m variants of reactant B, to obtain n×m variants, in n×m wells. One of ordinary skill in the art will realize that this particular procedure is most useful when smaller libraries are desired, and the specific wells can provide a ready means to identify the library members in a particular well.

In another embodiment of the present invention, a solid phase synthesis technique is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, developed by Furka. (Furka et al., *Abstr. 14th Int. Congr. Biochem.*, Prague, Czechoslovakia, 1988, 5, 47; Furka et al., *Int. J. Pept. Protein Res.* 1991, 37, 487; Sebestyen et al., *Bioorg. Med. Chem. Lett.,* 1993, 3, 413) In this technique, a mixture of related compounds can be made in the same reaction vessel, thus substantially reducing the number of containers required for the synthesis of very large libraries, such as those containing as many as or more than one million library members. As an example, the solid support scaffolds can be divided into n vessels, where n represents the number species of reagent A to be reacted with the scaffold structures. After reaction, the contents from n vessels are combined and then split into m vessels, where m represents the number of species of reagent B to be reacted with the scaffold structures. This procedure is repeated until the desired number of reagents is reacted with the scaffold structures to yield the inventive library.

The use of solid phase techniques in the present invention may also include the use of a specific encoding technique. Specific encoding techniques have been reviewed by Czarnik. (Czarnik, A. W., *Current Opinion in Chemical Biology,* 1997, 1, 60) As used in the present invention, an encoding technique involves the use of a particular "identifying agent" attached to the solid support, which enables the determination of the structure of a specific library member without reference to its spatial coordinates. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. It is most preferred, however for large combinatorial libraries, to use an alternative encoding technique to record the specific reaction history.

Examples of alternative encoding techniques that can be utilized in the present invention include, but are not limited to, spatial encoding techniques, graphical encoding techniques, including the "tea bag" method, chemical encoding methods, and spectrophotometric encoding methods. Spatial encoding refers to recording a reaction's history based on its location. Graphical encoding techniques involve the coding of each synthesis platform to permit the generation of a relational database. Examples of preferred spectrophotometric encoding methods include the use of mass spectroscopy, fluorescence emission, and nuclear magnetic resonance spectroscopy. In a preferred embodiment, chemical encoding methods are utilized, which uses the structure of the reaction product to code for its identity. Decoding using this method can be performed on the solid phase or off of the solid phase. One of ordinary skill in the art will realize that the particular encoding method to be used in the present invention must be selected based upon the number of library members desired, and the reaction chemistry employed.

Subsequent characterization of the library members, or individual compounds, can be performed using standard analytical techniques, such as mass spectrometry, Nuclear Magnetic Resonance Spectroscopy, and gas chromatograpy.

Once specific libraries of compounds have been prepared, specific assay techniques, such as those described herein, may be utilized to test the activity of the inventive compounds. In certain preferred embodiments, high throughput assay techniques are utilized.

Example 2

In vitro and In vivo Assays

Compounds of the present invention may be evaluated in a variety of assays to determine or characterize their biological activities. For example, the compounds of the invention can be tested for their ability to inhibit Src kinase or other protein kinases, to bind to bone, to inhibit bone resorption or to otherwise improve the relative dynamics of bone homeostasis. The compounds can also be evaluated for their cytotoxic and growth inhibitory effects on tumor cells of interest. Furthermore, the compounds can be evaluated for their ability to act as vitronectin receptor antagonists and as inhibitors of cell adhesion.

A. Anti-Resorption Cell Assay (Rabbit Osteoclast):

Femurs, tibias, and scapulas are isolated from 3–4 day old New Zealand white rabbits (Millbrook Farms, Amherst, Mass.). Bones are chopped and minced in a-MEM (Gibco-BRL) containing 0.55 g/L $NaHCO_3$, 10 mM HEPES (Gibco-BRL), 50 units/ml penicillin, and 0.05 mg/ml streptomycin, pH 7.1. Bone fragments are allowed to settle by gravitation, supernatant was collected and centrifuged at 400 RPM (Beckman GS-6KR) for two minutes, and the cell pellet is resuspended in the same medium supplemented with 10% HIFBS (Hyclone). For prebinding experiments, 0.75 ml of cell suspension is added to wells containing sperm whale dentine discs preincubated for 2 hours with 0.75 ml culture medium containing a 2× concentration of test compound. Alternatively, 0.75 ml of cell suspension is added to each well containing dentine slices preincubated with 0.75 ml culture medium alone and test compound is added after the adhesion phase. Sperm whale dentine was cut as 1 mm×6 mm circular discs. The adhesion phase was carried out for 30 minutes at 37_C and 5% $CO_2$ and then the medium and non-adherent cells and debris were removed by aspiration. Fresh culture medium containing serially diluted test compounds is added and cells were incubated on dentine for 24 hours at 37_C and 5% $CO_2$. After the resorption phase, dentine slices are soaked for 30 seconds in 0.5% sodium hypochlorite, wiped clean of adherent cells, and then stained for 30–45 seconds with 1% toluidine blue. Resorption is measured using reflective light microscopy and automated image analysis. The resorbed area is measured on the entire 6 mm disc. Remaining cells in the 24-well plates are stained for tartrate resistant acid phosphatase (TRAP) and also assessed visually for the presence of fibroblasts. Experiments are carried out containing triplicate samples for each concentration of compound tested with five untreated control samples per plate. $IC_{50}$ values are calculated based on the % resorption in the presence of compound relative to vehicle alone treated control samples. Data are calculated from at least three independent experiments each containing triplicate samples.

Generally speaking, in this assay, $IC_{50}$ values below about 10_M are of particular interest, while scores below 500 nM or below are preferred, and scores below about 100 nM are particularly preferred.

B. Hydroxyapatite Assay:

Hydroxyapatite is the principal mineral component of bone. Hydroxyapatite adsorption chromatography is used as an assay to evaluate the bone-targeting potential of both individual bone-targeting moieties ("monomers") and of pharmaceuticals incorporating bone-targeting groups.

Method: The retention time of a test compound is measured using a linear gradient from 10 mM sodium phosphate, 0.15 N NaCl, pH=6.8 to 500 mM sodium phosphate, 0.15 N NaCl, pH=–6.8 on a TSK-Gel HA 1000 high pressure liquid chromatography column (7.5 mm×75 mm). The retention time of the compound is expressed in terms of K=(retention time-void time)/void. This K value is corrected using two reference compounds to correct from inter-column and inter-system variation to obtain a K' value.

Reference Compounds: K' values were determined for known bone targeted compounds, the bisphosphonate, alendronate and tetracycline. Alendronate gave a K' value of 3.7 and tetracycline gave a K' value of 2.0.

C. Hypercalcemic Mouse Model for Testing In Vivo Anti Resorptive Activity

A murine hypercalcemia model for determining the efficacy of Src kinase inhibitors was developed. This model exploits the intrinsic effects of PTH (1-34) to stimulate the resorptive activity of osteoclasts in vivo. Briefly, compounds are each injected into mice subcutaneously, once or twice per day for five consecutive days. On the third day of test compound treatments, PTH administration begins. PTH (20 μg/kg) is given four times per day, subcutaneously, until the end of the study. Control animals receive PTH but do not receive test compounds. Blood samples are collected from the animals to obtain baseline (pre-PTH treatment), 48 hour and 72 hour (after initiation of PTH treatment) serum samples. The serum samples are analyzed for calcium concentration using the quantitative colorimetric assay reagent Arsenazo III (Sigma). Calcium serum levels for treated groups are compared to calcium serum levels of control groups and a percentage of inhibition of hypercalcemia is calculated for each time point. When a compound is effective in inhibiting the activity of osteoclasts, observed serum calcium concentrations are lower than those in animals that receive only PTH in the absence of test compound.

D. Kinase Assays

In addition to their ability to inhibit bone resorption, the compounds of the present invention are also able to inhibit protein kinase activity. For example, inventive compounds can be assessed for their ability to inhibit the activity of receptor and non-receptor tyrosine protein kinases. For example, the present invention presents a general method for determining the ability inhibit the activity of non-receptor tyrosine protein kinases (e.g., members of the src family, abl kinase, and ZAP70 kinase) and receptor tyrosine protein kinases (e.g., EGF family (c-erbB2, c-erbB3, and c-erbB4), the PDGF family (e.g., PDGF receptor, CSF-1, Kit, VEGF and FGF). Thus, the inventive compounds can be used in the immunomodulation and in the treatment of diseases of the immune system, for example in the case of inflammations or organ transplants. They are also suitable for the treatment of hyperproliferative diseases, including, but not limited to psoriasis, tumors, carcinomas and leukemias, and in fibrosis and restenosis. Additionally, compounds can be utilized for the treatment of diseases of the central or the peripheral nervous system where signal transmission by at least one tyrosine protein kinase is involved. Furthermore, Src and certain other kinases are believed to mediate signaling activity in response to a variety of growth factors, including VEGF, vascular endothelial growth factor, which is an angiogenic factor that promotes vascular permeability, and thus certain inhibitors are useful as antiangiogenic agents. In addition to the kinase assays described in this section, certain other kinase assays are described in the context of anti-angiogenic agents below, for example.

The following Example presents a general method for determining the effect of the inventive compounds on the phosphorylation of a kinase's target, and use of certain exemplary assays will additionally be presented below. It will be appreciated that a number of additional assays for receptor and non-receptor tyrosine protein kinases are available in the art.

General Method: A purified or partially purified kinase is incubated with a peptide comprising the target sequence of the kinase under conditions suitable for the kinase to phosphorylate its target sequence of amino acids (i.e., protein, peptide). The particular requirements of the kinase may be determined empirically by one of skill in the art, or the conditions that have been published for a particular kinase (for example, see Table I in Boutin "Tyrosine protein kinase assays" *J. Chromatography B* 684:179–199, 1996; incorporated herein by reference) may be used. The extent of phosphorylation of the target peptide is determined in the presence and absence of the inventive compound and may be determined in the presence of varying concentrations of the inventive compound. The phosphorylation rate may be determined by any means known in the art including electrophorectic assays, chromatographic assays, phosphocellulose assays, etc.

In an electrophorectic assay, a radiolabled phosphate donor such as ATP or GTP is incubated with the peptide substrate in the presence of a kinase. The phosphorylated substrate versus the phosphate donor (e.g., ATP, GTP) are separated via thin-layer electrophoresis (Hunter *J. Biol. Chem.* 257:4843, 1982; incorporated herein by reference). Any matrix may be used in the electrophoresis step including polyacrylamide, cellulose, etc. The extent of phosphorylation may then be determined by autoradiography or scintillation counting.

The labeled phosphate donor may be separated from the phosphorylated amino acid sequence by standard chromatography techniques. Any matrix may be used to effect the separation including ion exchange resins, PEI cellulose, silica gel, etc. Standard column chromatography methods may be used, or HPLC methods may be used for faster cleaner separations. The radio-labeled peptides are detected by scintillation counting to determine the phosphorylation rate.

Another method which is historically the most popular is the phosphocellulose paper assay, first described by Witt et al. (Witt et al. *Anal. Biochem.* 66:253, 1975; incorporated herein by reference). This method is well adapted to the screening of inhibitors (Traxler et al. *J. Med. Chem.* 34:2328, 1991, incorporated herein by reference).

Immunological methods may also be used to detect the phosphorylation of a peptide or protein substrate. For example, anti-phosphotyrosine antibodies may be used in the detection or precipitation of phosphorylated amino acid sequences. The method has the advantage of not requiring the used of radio-labeled ATP.

In comparing the rates of phosphorylation in the presence and absence of the test compound, the compound should lead to at least a 25% decrease in the rate of phosphorylation, more preferably at least 50%, and most preferably at least 75%. These decreases are preferably obtained at micromolar concentrations of the compound and more preferably nanomolar concentrations (e.g., less than 100 nM).

In addition, a Quantitative Kinase Activity Assay Using a 96-Well Plate can be determined. The following Example has been adapted from the assay described by Asthagiri et al. (*Anal. Biochem.* 269:342–347, 1999; incorporated herein by reference). This assay allows high-throughput screening of a large number of potential kinase inhibitors.

The surface of a microtiter plate is coated with antibodies directed against the kinase to be studied. Reacti-Bind protein A-coated wells (Pierce, Rockford, Ill.) are incubated overnight at 4° C. with 50 μL of 10 μg/ml antibody in blocking buffer containing 1% BSA, 50 mM Tris (pH 7.5), 150 mM NaCl, and 0.05% Triton. Wells are then washed three times with blocking buffer. A cell lysate containing the kinase to be studied is diluted in lysis buffer to a total volume of 50 μl incubated for 3 hours at 4° C. to allow the antibody to capture the kinase. To measure background, an extra well is incubated with just lysis buffer and is handled throughout the assay in the same manner as other samples. Each well is then washed twice with 200 μl wash buffer containing 50 mM Tris (pH 7.5) and 150 mM NaCl and twice more with 200 μl kinase wash buffer containing 20 mM Tris (pH 7.5), 15 mM magnesium chloride, 5 mM β-glycerolphosphate (pH 7.3), 1 mM EGTA, 0.2 mM sodium orthovanadate, and 0.2 mM DTT. The contents of the well are then resuspended in 20 μl kinase wash buffer.

To each well is then added 20 μl of 2 mg/ml substrate containing the target amino acid sequence of the kinase. To initiate the in vitro reaction, 20 μl kinase assay buffer containing 20 mM Tris (pH 7.5), 15 mM magnesium chloride, 5 mM β-glycerophosphate (pH 7.3), 1 mM EGTA, 0.2 mM sodium orthovanadate, 0.2 mM DTT, 0.4 μM protein kinase A inhibitor peptide (Upstate Biotech, Lake Placid, N.Y.), 4 μM protein kinase C inhibitor peptide (Upstate Biotech), 4 μM calmidazolium (Upstate Biotech), 25 μM ATP, and 6 μCi [?-$^{32}$P]-ATP is added to two wells. To one of the wells is added the test compound at a concentration ranging from 1 mM to 1 nM. Reactions contents are maintained under agitation at 37° C. with the Jitterbug (Boekel, Feasterville, Pa.). After 10 minutes, the reactions are quenched with 60 μl of 75 mM phosphoric acid.

[$^{32}$P]-labeled substrate is separated from unreacted [$^{32}$P]-ATP by filtering 40 μl of the quenched reaction contents through a phosphocellulose filter using the Millipore Multiscreen system (Millipore, Bedford, Mass.). Each filter is washed five times with 200 μl 75 mM phosphoric acid and three times with 200 μl 70% ethanol. The filters are allowed to dry before punching out the filters into scintillation vials. $^{32}$P amounts on the filter paper are quantified using CytoScint (ICN Biomedicals, Costa Mesa, Calif.) scintillation fluid and a RackBeta (Wallac, Gaithersburg, Md.) scintillation counter. $^{32}$P measurements are adjusted by subtracting the radioactivity associated with the background sample, and measurements observed in presence and absence of the test compound are compared.

If desired one may use an assay involving immunoprecipitation of the kinase. The following such assay was adapted from the method by Bondzi et al. (*Oncogene* 19:5030–5033, 2000; incorporated herein by reference).

Cells expressing the kinase of interested are washed once in PBS and lysed in buffer containing 20 mM Tris (pH 7.9), 137 mM NaCl, 5 mM EDTA, 1 mM EGTA, 10 mM NaF, 1 mM sodium pyrophosphate, 100 μM β-glycerophosphate, 10 μg/ml aprotinin, 1 mM PMSF, 10% glycerol, and 1% v/v Triton X-100. The lysate is cleared by centrifugation at 10,000×g for 10 minutes at 4° C. Protein concentrations are determined using the BCA method (Pierce, Rockford, Ill., USA). Five hundred μg of the lysate protein is then added to 2 μg monoclonal anti-kinase antibody directed against a portion of the protein. Antibodies are prebound to 100 μl of protein A+G-agarose beads (Santa Cruz Biotechnology, Santa Cruz, Calif., USA) by incubation for one hour at 4° C. on a slow rotator. Increasing amounts of lysate protein (0, 50, 100, 200, 400, 800, and 1600 μg) or increasing amounts of anti-kinase antibody (0, 0.5, 1.0, 2.0, and 4.0 μg) are used in the immunoprecipitation step. The immunocomplex is washed three times in ice-cold lysis buffer, once in ice-cold washing buffer containing 10 mM HEPES (pH 7.4), 100 mM NaCl, 20 μg/ml aprotinin, and 0.5% NP-40, and once in ice-cold reaction buffer containing 20 mM Tris (pH 7.4), 20 mM NaCl, 1 mM DTT, 10 mM MgCl$_2$, and 1 mM MnCl$_2$. The kinase reaction is performed in the presence of 20 μM ATP and 500 ng of the peptide substrate in a total volume of 40 μl of reaction buffer at 30° C. for 30 minutes with gentle agitation. The kinase reaction may be performed using increasing incubation intervals (0, 5, 10, 15, 20, 25, and 30 minutes), increasing amounts of the substrate (0, 100, 200, 400, and 500 ng), and increasing concentrations of the test compound (0, 1, 10, 100, 1000, 10000, and 100000 ng). The kinase reaction is terminated by the addition of 40 μl 2×SDS sample buffer followed by boiling for 10 minutes. The samples are resolved by SDS-PAGE, transferred to Immobilon-P membrane (Millipore Corp., Bedford, Mass., USA), and probed with a polyclonal phospho-substrate antibody. The blot is stripped and reprobed sequentially for kinase and substrate with anti-kinase antibody and anti-substrate antibody, respectively. Dectection is accomplished using the ECL-Plus chemiluminescent system (Amersham, Arlington Heights, Ill., USA) and visualized using a Fuji cooled CCD camera and the Aida 2.0 software package (Raytest Inc., New Castle, Del., USA).

Certain Exemplary Kinase Assays:

a) Src Kinase Inhibition Assay:

Compounds are tested for their ability to inhibit Src kinase using the scintillation proximity assay (SPA) technology as developed by Amersham. Reagents include: Streptavidin SPA beads from Amersham, 2-[N-morpholino]ethanesulfonic acid from Sigma, ATP from Boerhinger Mannheim, [$^{33}$P]ATP: from NEN (NEG 602H), the substrate—biotinylated peptide substrate 1 (PKS1) (cdc2 peptide) from Pierce which is prepared at 12.5 μM (5× solution) in kinase buffer, and the enzyme, human recombinant c-Src at 135 μg/ml (stock solution) which is diluted 1/40 in kinase buffer (3.38 μg/ml) before use. Buffers include: (a) Kinase buffer which contains MES 30 mM pH 6.8, MgCl$_2$ 10 mM, Orthovanadate 0.25 mM, PMSF 0.1 mM, and DTT 1 mM; (b) ATP buffer which contains ATP 5 mM in MgCl$_2$ 50 mM buffer (stock solution). Note that before each use dilute in MES to 100 μM (5× solution) add 100 μCi/mL [$^{33}$P]ATP; and (c) PBS Stop buffer which contains ATP 0.1 mM, EDTA 40 mM, Triton 0.1%. Streptavidin beads are suspended at 3.3 mg/ml in stop buffer and mixed by shaking. The Kinase reaction proceeds by stepwise addition to wells on the 96 well-plate of the following: (a) 10 μL kinase buffer+10% DMSO or compound to be tested at different concentration in MES+10% DMSO, (b) 10 μL kinase buffer, (c) 10 μL substrate 12.5 μM, (d) 10 μL enzyme 3.38 μg/ml, and (e) 10 μL ATP 100 μM containing 0.2 μCi [$^{33}$P]ATP. Incubation for 2 hours at 30 degrees C. is followed by addition of 150 μL Stop buffer containing 500 μg streptavidin beads. Incubation proceeds for 30 min at room temperature, followed by centrifugation for 5 min at 2000 rpm, and reading on a Wallac Microbeta Scintillation counter.

b) Inhibition of Epidermal Growth Factor Receptor Kinase (EGF-R, Membrane Extract):

Representative compounds of the invention are evaluated for their ability to inhibit the phosphorylation of the tyrosine residue of a peptide substrate catalyzed by the enzyme epidermal growth factor receptor kinase in the standard pharmacological test procedure described below. The peptide substrate (RR-SRC) has the sequence arg-arg-leu-ile-glu-asp-ala-glu-tyr-ala-ala-arg-gly. The enzyme is obtained as a membrane extract of A431 cells (American Type Culture Collection, Rockville, Md.). A431 cells are grown in T175 flasks to 80% confluency. The cells are washed twice with phosphate buffered saline (PBS) with 1.0 mM ethylenediamine tetraacetic acid (EDTA) at room temperature and centrifuged at 600 g for 10 minutes. The cells were solubilized in 1 ml per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/ml aprotinin, 10 mg/ml leupeptin, 0.1 mM sodium orthovanadate} in a Dounce homogenizer with 10 strokes on ice. The lysate was centrifuged at 600 g for 10 minutes first to clear cell debris and the supernatant further centrifuged at 100,000 g for min at 4° C. The membrane pellet was suspended in 1.5 ml HNG buffer (50 mM HEPES, pH 7.6, 125 mM NaCl, 10% glycerol). The membrane extract was divided into aliquots, immediately frozen in liquid nitrogen and stored at −70° C.

Compounds to be evaluated are made into 10 mg/ml stock solutions in 100% dimethylsulfoxide (DMSO). Prior to experiment, stock solutions are diluted to 500 mM with buffer (30 mM Hepes pH 7.4) and then serially diluted to the desired concentration.

An aliquot of the A431 membrane extract (10 mg/ml) is diluted in 30 mM HEPES (pH 7.4) to give a protein concentration of 50 μg/ml. To 4 μl of enzyme preparation, EGF (1 μl at 12 μg/ml) is added and incubated for 10 minutes on ice followed by 4 μl of the test compound or buffer; this mix is incubated on ice for 30 minutes. To this is added the 33P-ATP (10 mCi/ml) diluted 1:10 in assay buffer along with the substrate peptide at a concentration of 0.5 mM (control reactions get no test compound) and the reaction is stopped with 10% TCA and left on ice for at least 10 minutes after which tubes are microcentrifuged at full speed for 15 minutes. A portion of the supernatants are spotted on P81 phosphocellulose discs and washed twice in 1% acetic acid then water for 5 minutes each followed by scintillation counting, and analyzed according to standard methods to determine percent inhibition.

c). Inhibition of Kinase Insert Domain Containing Receptor (KDR; the Catalytic Domain of the VEGF Receptor):

In this standard pharmacological test procedure, KDR protein is mixed, in the presence or absence of an inhibitor compound, with a substrate peptide to be phosphorylated (a copolymer of glutanic acid and tyrosine, E:Y::4:1) and other cofactors such as $Mg^{++}$ and sodium vanadate (a protein tyrosine phosphatase inhibitor) in an appropriate buffer to maintain pH (7.2). ATP and a radioactive tracer (either $^{32}P$- or $^{33}P$-labeled ATP) is then added to initiate phosphorylation. After incubation, the radioactive phosphate associated with the acid-insoluble fraction of the assay mixture is then qualified as reflection of substrate phosphorylation. This radioactive format is used to identify inhibitors of KDR tyrosine kinase activity where the $IC_{50}$ is the concentration of the drug that inhibits the substrate phosphorylation by 50%.

E. Cytoxicity and Inhibition of Tumor Growth:

Certain compounds of this invention have also demonstrated cytotoxic and antitumor activity and thus may be useful in the treatment of cancer and other cell proliferative diseases. Compounds are assayed for anti-tumor activity using in vivo and in vitro assays which are well known to those skilled in the art. Generally, initial screens of compounds to identify candidates for anti-cancer drugs are performed in cellular in vitro assays. Compounds identified as having anti-cell proliferative activity can then be subsequently assayed in whole organisms for anti-tumor activity and toxicity. The initial screens are preferably cellular assays which can be performed rapidly and cost-effectively relative to assays that use whole organisms. For purposes of the present invention, the term "anti-proliferative compound" is used to mean compounds having the ability to impede or stop cells from progressing through the cell cycle and dividing. For purposes of the present invention, the terms "anti-tumor" and "anti-cancer" activity are used interchangeably.

Methods for determining cell proliferation are well known and can be used to identify compounds with anti-proliferative activity. In general, cell proliferation and cell viability assays are designed to provide a detectable signal when cells are metabolically active. Compounds are tested for anti-cell proliferation activity by assaying for a decrease in metabolic activity. Commonly used methods for determining cell viability depend upon, for example, membrane integrity (e.g. trypan blue exclusion) or incorporation of nucleotides during cell proliferation (e.g. BrdU or $^3$H-thymidine).

Preferred methods of assaying cell proliferation utilize compounds that are converted into a detectable compound during cell proliferation. Particularly preferred compounds are tetrazolium salts and include without limitation MTT (3-(4,5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. *Biochim Biophys Acta* 1451(1): 73–81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. *J. Immunol. Methods*. 65:55–63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

Any cultured cell line may be used to screen compounds for antiproliferative activity. In certain embodiments of the invention cell lines utilized include, but are not limited to, Exemplary cell lines utilized for the determination of the ability of inventive compounds to inhibit cellular proliferation include, but are not limited to COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

Preferably, the cell line is a mammalian, but is not limited to mammalian cells since lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, the present invention does not limit the use of mammalians cells lines to only the ones listed.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38, and CV-1I/EBNA-1.

Other in vitro cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541–51; incorporated herein by reference) used HeLa cells containing an inducible variant of GFP to detect compounds that inhibited expression of the GFP, and thus inhibited cell proliferation.

Compounds identified by in vitro cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (*Cancer Metastasis Rev.* 17:301–304, 1998–99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g., at intrapertoneal sites) and survival is the measured endpoint. Parameters to be assayed with routine screening include different tumor models, various tumor and drug routes, and doses amounts and schedule. For a review of the use of mice in detecting anti-tumor compounds see Corbett et al. (Invest New Drugs. 15:207–218, 1997; incorporated herein by reference)

F. Vascular Permeability:

As mentioned above, certain kinases are believed to mediate signaling activity in response to a variety of growth factors, including VEGF, vascular endothelial growth factor, which is an angiogenic factor that promotes vascular permeability. For example, certain compounds are tested for the ability to inhibit the tyrosine kinase activity associated with the VEGF receptors such as Flt and/or KDR and for their ability to inhibit angiogenesis and/or increased vascular permeability. Additionally, these compounds can be tested for the ability to inhibit the tyrosine kinase activity associated with Src and for their ability to inhibit angiogenesis and/or increased vascular permeability. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which are obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5:519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(*Sf*21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, *Sf*21 cells are infected with plaque-pure cFlt recombinant virus at a multiplicity of infection of 3 and are harvested 48 hours later. Harvested cells are washed with ice cold phosphate buffered saline solution (PBS) 10 mM sodium phosphate pH 7.4, 138 mM NaCl, 2.7 mM KCl) then resuspended in ice cold HNTG/PMSF (20 mM Hepes pH7.5, 150 mM NaCl, 10% v/v glycerol, 1% v/v Triton X100, 1.5 mM $MgCl_2$, 1 mM ethylene glycol-bis(.beta.aminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension is centrifuged for 10 minutes at 13,000 rpm at 4° C., the supernatant (enzyme stock) was removed and stored in aliquots at −70° C. Each new batch of stock enzyme is titrated in the assay by dilution with enzyme diluent (100 mM Hepes pH 7.4, 0.2 mM $Na_3VO_4$, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution is prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution is dispensed into all wells of assay plates (Nunc maxisorp 96-well immunoplates) which are sealed and left overnight at 4° C. On the day of the assay the substrate solution is discarded and the assay plate wells are washed once with PBST (PBS containing 0.05% v/v Tween 20) and once with 50 mM Hepes pH7.4.

Test compounds are diluted with 10% dimethylsulphoxide (DMSO) and 25 µl of diluted compound is transferred to wells in the washed assay plates. "Total" control wells contained 10% DMSO instead of compound. Twenty five microliters of 40 mM $MnCl_2$ containing 8 µM adenosine-5'-triphosphate (ATP) are added to all test wells except "blank" control wells which contained $MnCl_2$ without ATP. To start the reactions 50 µl of freshly diluted enzyme is added to each well and the plates are incubated at room temperature for 20 minutes. The liquid is then discarded and the wells are washed twice with PBST. One hundred microliters of mouse IgG anti-phosphotyrosine antibody (Upstate Biotechnology Inc. product 05-321), diluted 1 in 6000 with PBST containing 0.5%, v/v bovine serum albumin (BSA), is added to each well and the plates are incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, is added and the plates are incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), is added to each well. Plates are then incubated for 20–60 minutes at room temperature until the optical density value of 30 the "total" control wells, measured at 405 nm using a plate reading spectrophotometer, is approximately 1.0. "Blank" (no ATP) and "total" (no compound) control values are used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells are isolated in MCDB 131 (Gibco BRL)+7.5% v/v foetal calf serum (FCS) and are plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they are dosed with the appropriate growth factor (i.e. VEGF 3 ng/ml, EGF 3 ng/ml or β-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells are harvested using a 96-well plate harvester (Tomtek) and then are assayed for incorporation of tritium with a Beta plate counter. Incorporation of radioactivity into cells, expressed as cpm, is used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. It has been found that prior treatment of the rats with a neutralising monoclonal antibody to VEGF significantly reduces the acute increase in uterine weight, confirming that the increase in weight is substantially mediated by VEGF.

Groups of 20 to 22-day old rats are treated with a single subcutaneous dose of oestradiol benzoate (2.5 .mu.g/rat) in a solvent, or solvent only. The latter served as unstimulated controls. Test compounds are orally administered at various times prior to the administration of oestradiol benzoate. Five hours after the administration of oestradiol benzoate the rats are humanely sacrificed and their uteri are dissected, blotted and weighed. The increase in uterine weight in groups treated with test compound and oestradiol benzoate and with oestradiol benzoate alone is compared using a Student T test. Inhibition of the effect of oestradiol benzoate is considered significant when $p<0.05$.

G. Inhibition of Farnesyl Protein Transferase:

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known, ras, which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzyme that catalyzes this modification, farnesyl protein transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to the transformation. Since mutated, oncogenic forms of ras are frequently found in many human cancers, most notably in more than 50% of colon and pancreatic carcinomas (Kohl et al., *Science*, vol. 260, 1834–1837, 1993), it has been suggested that farnesyl transferase inhibitors can be very useful against these types of cancer. Accordingly, exemplary methods are presented below:

(a) In vitro Assay for Inhibition of Farnesyl Protein Transferase

Human farnesyl protein tranferase is prepared essentially as described (Y. Reiss et al., Methods: A Companion to Methods in Enzymology vol 1, 241–245 (1990). Kirsten virus transformed human osteosarcoma (KHOS) cells (American Type Culture Collection, Rockville, Md., USA) grown as solid tumors in nude mice or grown as monolayer cell cultures are used as a source of human enzyme. Briefly, cells or tumors are homogenized in buffer containing 50 mM Tris, 1 mM EDTA, 1 mM EGTA and 0.2 mM phenylmethylsulfonylfluoride (pH 7.5). The homogenates are centrifuged 28,000×g for 60 minutes and the supernatants are collected. A 30–50% ammonium sulfate fraction is prepared, and the resulting precipitate is resuspended in a small (10 to 20 ml) volume of dialysis buffer containing 20 mM Tris, 1 mM dithiothreitol and 20 µM $ZnCl_2$. The ammonium sulfate fraction was dialyzed overnight against two changes of the same buffer. The dialyzed material is applied to a 10×1 cm Q Fast Flow Sepharose (Pharmacia LKB Biotechnology Inc., Piscataway, N.J., USA) which is preequilibrated with 100 ml of dialysis buffer supplemented with 0.05 M NaCl. The column is then washed with an additional 50 ml of dialysis buffer plus 0.05 M NaCl followed by a gradient from 0.05 M to 0.25 M NaCl prepared in dialysis buffer. The enzyme activity is then eluted with a linear gradient of 0.25 to 1.0 M NaCl prepared in the dialysis buffer. Fractions containing 4 to 5 ml volumes of column eluate are then collected and analyzed for farnesyl protein transferase activity. Fractions with enzyme activity are pooled and supplemented with 100 µM $ZnCl_2$. Enzyme samples are stored frozen at −70° C.

The activity of farnesyl protein transferase is measured using the Farnesyl Transferase [$^3$H] Scintillation Proximity Assay (Amersham International plc., England) under the conditions specified by the manufacturer. To assay for inhibitors of the enzyme, 0.20 µCi of the [$^3$H]-farnesylpyrophosphate substrate and the biotinylated lamin B peptide substrate (biotin-YRANSNRSCAIM) are mixed with test compounds in a raction buffer consisting of 50 mM HEPES, 30 mM $MgCl_2$, 20 mM KCl, 5 mM dithiothreitol, 0.01% Triton X-100. Test compounds are delivered in a 10 µl volume of dimethylsulfoxide (DMSO) to achieve concentrations of 1 and 10 µg/ml in a final volume of 100 µl. The reaction mixture is then warmed to 37° C. The enzyme reaction is started by adding 20 µl of diluted human farnesyl protein transferase. Sufficient enzyme preparation is added to produce between 4000 to 15000 cpm of reaction product during the 60 minutes of reaction incubation at 37° C. Reactions are terminated by the addition of STOP/scintillation proximity bead reagent (Amersham). The reaction product [$^3$H]-farnesyl-(Cys)-biotin lamin B peptide synthesized in the presence of absence of test compounds is quantified as cpm by counting on a Wallac Model 1480 Microbeta Liquid Scintillation Counter. The cpm of product is considered to be farnesyl protein transferase activity. The protein farnesyl transferase activity observed in the presence of test compound is normalized to farnesyl transferase activity in the presence of 10% DMSO and expressed as percent inhibition. In separate studies, those test compounds exhibiting 50% or greater inhibition of farnesyl protein transferase activity are evaluated for concentration-dependent inhibition of enzyme activity. The effects of test compounds in those studies are calculated as $IC_{50}$ (concentration of test compound producing 50% inhibition of enzyme activity) using the LGIC50 computer program written by the Science Information Division of R.W. Johnson Pharmaceutical Research Institute (Spring House, Pa., USA) on a VAX computer.

(b) Ras-transformed Cell Phenotype Reversion Assay:

Insertion of activated oncogenes such as the mutant ras gene into mouse NIH 3T3 cells converts the cells into a transformed phenotype. The cells become tumorigenic, display anchorage independent growth in semi-solid medium and lost contact inhibition. Loss of contact inhibition produces cell cultures which no longer form uniform monolayers. Rather the cells pile up into multicellular nodules and grow to very high saturation densities in plastic tissue culture dishes. Agents such as protein farnesyl transferase inhibitors that revert the ras transformed phenotype restore the uniform monolayer growth pattern to cells in culture. This reversion is easily monitored by counting the number of cells in tissue culture plates. Transformed cells will achieve higher cell numbers than cells that have reverted to an untransformed phenotype. Compounds that revert the transformed phenotype should produce antitumor effects in tumors bearing ras gene mutations:

Methods:

Compounds are screened in tissue culture in NIH 3T3 cells transformed by the T24 activated human H-ras gene. Cells are seeded at an initial density of 200,000 cells per well (9.6 cm2 surface area) in six-well cluster tissue culture plates. Test compounds are immediately added to 3.0 ml cell growth medium in a 3.0 µl volume of DMSO, with a final concentration of DMSO in the cell growth medium of 0.1%. The test compounds are run at concentrations of 5, 10, 50, 100 and 500 nM along with a DMSO treated vehicle control. (In case a high activity is observed at 5 nM, the test compound is tested at even lower concentrations). The cells are allowed to proliferate for 72 hours. The cells are then detached in 1.0 ml trypsin-EDTA cell dissociation medium and counted on a Coulter particle counter.

Measurements:

Cell numbers expressed as cells per well are measured using a Coulter Particle Counter. All cell counts are corrected for the initial cell input density by subtracting 200,000.

Control cell counts=[cell counts from cells incubated with DMSO vehicle−200,000]

Test compound cell counts=[cell counts from the cells incubated with test compound−200,000].

Test compound % inhibition=[1−(test compound cell counts/control cell counts)]×100%

$IC_{50}$ (i.e. the test compound concentration required to inhibit enzyme activity by 50%) is calculated if sufficient data are available.

(c) Farnesyl Protein Transferase Inhibitor Secondary Tumor Model:

The enzyme farnesyl protein transfersase catalyzes the covalent attachment of a farnesyl moiety derived from farnesyl pyrophosphate to the oncogene product $p21^{ras}$. This directs $p21^{ras}$ to attach to plasma membranes. Once attached to plasma membranes, mutant or oncogenic forms of $p21^{ras}$ will provide a signal for the transformation and uncontrolled growth of malignant tumor cells. Therefore, inhibitors of protein farnesyltransferase will prevent the membrane attachment of $p21^{ras}$ and inhibit growth of fas-transformed tumors. Nude mice are innoculated with $1 \times 10^6$ of T24 activated human H-ras gene transformed NIH 3T3 fibroblast cells (T24 cells), subcutaneously in the inguinal region. After three days to allow tumors to become established, treatment with test compounds is begun via the oral route. The test compounds are dissolved in a 20% β-cyclodextrin in 0.1 N HCl solution and administered orally as 0.1 ml of compound solution per 10 gram mouse body weight. Routinely used doses are 6.25, 12.5 and 25 mg/kg. Body weights and tumor sizes are monitored during the ensuing 15 days of treatment. At the end of treatment, animals are sacrificed and tumors are weighed.

The mean vehicle treated tumor weight" is defined as the mean tumor weight from 10 to 15 mice treated with test compound.

The "mean tumor weight" is defined as the mean tumor weight from 10 to 15 mice not treated with the test compound.

% reduction final tumor weight=[1−(mean tumor weight/mean vehicle treated tumor weight)]× 100%

H. Vitronectin Receptor Assays:

a) Kistrin Binding Assay

The inhibition of the binding of kistrin to human vitronectin receptor (VnR) described below is a test method by which the antagonistic action of the compounds of the invention on the vitronectin receptor $\alpha_{v\_3}$ can be determined ($\alpha_{v\_3}$ ELISA Test; the test method is abbreviated as "K/VnR" in the listing of the test results).

Purification of Kistrin

Kistrin is purified according to the methods of Dennis et al., as described in Proc. Natl. Acad. Sci. USA 87 (1989) 2471 and Proteins: Structure, Function and Genetics 15 (1993) 312.

Purification of Human Vitronectin Receptor ($\alpha_{v\_3}$)

Human vitronectin receptor is obtained from the human placenta according to the method of Pytela et al., Methods Enzymol. 144 (1987) 475. Human vitronectin Receptor $\alpha_{v\_3}$ can also be obtained from some cell lines (for example from 293 cells, a human embryonic kidney cell line) which are co-transfected with DNA sequences for both subunits $\alpha_v$ and _3 of the vitronectin receptor. The subunits are extracted with octyl glycoside and then chromatographed through concanavalin A, heparin-Sepharose and S-300.

Monoclonal Antibodies.

Murine monoclonal antibodies which are specific for the _3 subunits of the vitronectin receptor, are prepared according to the method of Newman et al., Blood, 1985, 227, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates are coated with a solution of kistrin (0.002 mg/ml) according to the method of Dennis et al., as described in Proteins: Structure, Function and Genetics 15 (1993) 312. The plates are then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), MgCl$_2$ (1 MM), CaCl$_2$ (1 mM), MnCl$_2$ (1 mM), pH 7). Solutions of known inhibitors and of the test substances are prepared in concentrations from $2\times10^{-12}$ to $2\times10^{-6}$ mol/l in assay buffer (BSA (0.5%, RIA grade or better); Tris-HCl (50 mM), NaCl (100 mM), MgCl$_2$ (1 mM), CaCl$_2$ (1 mM), MnCl$_2$ (1 mM), pH 7). The blocked plates are emptied, and in each case 0.025 ml of this solution which contains a defined concentration ($2\times10^{-12}$ to $2\times10^{-6}$ mol/l) either of a known inhibitor or of a test substance, are added to each well. 0.025 ml of a solution of the vitronectin receptor in assay buffer (0.03 mg/ml) is pipetted into each well of the plate and the plate is incubated at room temperature for 60–180 min on a shaker. In the meantime, a solution (6 ml/plate) of a murine monoclonal antibody specific for the _3 subunit of the vitronectin receptor is prepared in assay buffer (0.0015 mg/ml). A second rabbit antibody (0.001 ml of stock solution/6 ml of the murine monoclonal anti-_3 antibody solution) which is an anti-mouse Fc HRP antibody conjugate is added to this solution, and this mixture of murine anti-_3 antibody and rabbit anti-mouse Fc HRP antibody conjugate is incubated during the time of the receptor-inhibitor incubation. The test plates are washed four times with PBS solution which contains 0.05% Tween-20, and in each case 0.05 ml/well of the antibody mixture is pipetted into each well of the plate and incubated for 60–180 min.

The plate is washed four times with PBS/0.05% Tween-20 and then developed with 0.05 ml/well of a PBS solution which contains 0.67 mg/ml of o-phenylenediamine and 0.012% of H$_2$O$_2$. Alternatively to this, o-phenylenediamine can be employed in a buffer (pH 5) which contains Na$_3$PO$_4$ and citric acid. The color development is stopped using 1 N H$_2$SO$_4$ (0.05 ml/well). The absorption for each well is measured at 492–405 nm and the data are evaluated by standard methods.

b) Vitronectin/293 Cell Test

In this test the inhibition of binding of 293 cells to human vitronectin (Vn) by the compounds of the invention is determined (the test method is abbreviated as Vn/293 cell test in the listing of the test results).

Purification of Human Vitronectin

Human vitronectin is isolated from human plasma and purified by affinity chromatography according to the method of Yatohgo et al., Cell Structure and Function 23 (1988) 281.

Cell Test 293 cells, a human embryonic kidney cell line, which are cotransfected with DNA sequences for the $\alpha_v$ and _3 subunits of the vitronectin receptor $\alpha_{v\_3}$, are selected for a high rate of expression (>500,000 $\alpha_{v\_3}$ receptors/cell) according to the FACS method. The selected cells are cultured and sorted again by means of FACS in order to obtain a stable cell line (15 D) with expression rates>1,000,000 copies of $\alpha_{v\_3}$ per cell.

A Linbro 96-well tissue culture plate with a flat bottom is coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2\times10^{-3}$ mol/l in glucose-containing DMEM medium are prepared and 0.05 ml/well of the solution were added to the plate in each case. The cells which express high levels of $\alpha_{v\_3}$ (for example 15 D) are suspended in glucose-containing DMEM medium and the suspension is adjusted to a content of 25,000 cells/0.05 ml of medium. 0.05 ml of this cell suspension is added to each well and the plate was incubated at 37° C. for 90 min. The plate is washed 3 times with warm PBS in order to remove unbound cells. The bound cells are lyzed in citrate buffer (25 mM, pH 5.0) which contained 0.25% Triton X-100. The hexoseamidase substrate p-nitrophenyl-N-acetyl-_-D-glucosaminide is then added and the plate is incubated at 37° C. for 90 min. The reaction is stopped with a glycine (50 mM)/EDTA (5 mM)

buffer (pH 10.4) and the absorption of each well is measured at 405 to 650 nm. The data are analyzed according to standard methods.

Example 3

Pharmaceutical Formulations

The following formulations exemplify typical pharmaceutical compositions in dosage unit form suitable for systemic or topical administration to warm-blooded animals in accordance with the present invention.

"Active ingredient" (A.I.), as used herein, relates to a compound of formula (I) and all classes and subsets as described herein, a pharmaceutically acceptable derivative thereof, or a stereochemically isomeric form thereof.

A. Oral Solutions: 9 g of methyl 4-hydroxybenzoate and 1 g of propyl 4-hydroxybenzoate are dissolved in 4 l of bioling purified water. In 3 l of this solution are dissolved first 10 g of 2,3-dihydroxybutanedioic acid and thereafter 20 grams of the active ingredient. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the active ingredient per teaspoonfull (5 ml). The resulting solution is filled in suitable containers.

B. Capsules:

20 grams of the active ingredient, 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the active ingredient.

C. Film-coated Tablets:

Preparation of tablet core: A mixture of 100 g of the active ingredient, 570 g lactose and 200 g starch is mixed well and thereafter humidified with a solution of 5 g sodium dodecyl sulfate and 10 g polyvinyl pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10,000 tablets, each comprising 10 mg of the active ingredient.

Coating: To a solution of 10 g methyl cellulose in 75 ml of denatrurated ethanol is added a solution of 5 g of ethyl cellulose in 150 ml of dichloromethane. Then there are added 75 ml of dichloromethane and 2.0 ml 1,2,3-propanetriol. 10 g of polyethylene glycol is molten and dissolved in 75 ml of dichloromethane. The latter solution is added to the former and then 2.5 g of magnesium octadecoanoate, 5 g polyvinylpyrrolidone and 30 ml of concentrated color suspension is added and the mixture is homogenated. The tablet cores are coated with the mixture in a coating apparatus.

D. Injectable solution: 1.8 g methyl 4-hydroxybenzoate and 0.2 g propyl 4-hydroxybenzoate were dissolved in about 0.5 l of boiling water for injection. After cooling to about 50 C, 4 g lactic acid. 0.05 g propylene glycol, and 4 grams of the active ingredient were added while stirring. The solution was then cooled to room temperature and supplemented with water for injection q.s. ad 1 l volume, giving a solution of 4 mg/ml of active ingredient. The solution was sterilized by filtration and filled in sterile containers.

The invention claimed is:

1. A compound chosen from the following:

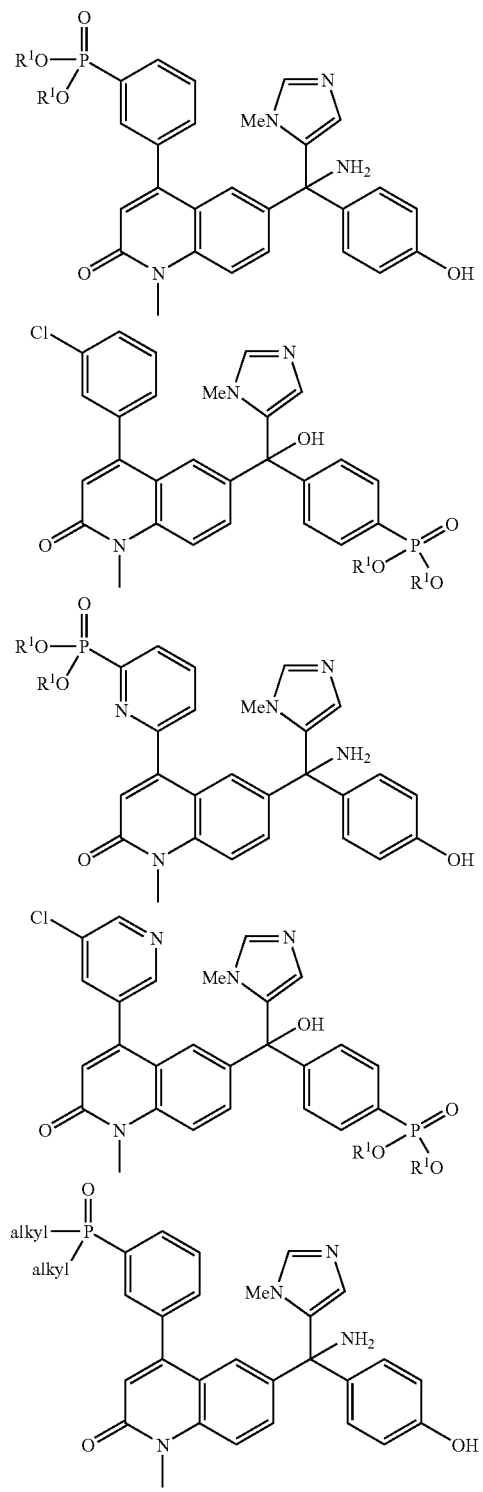

-continued
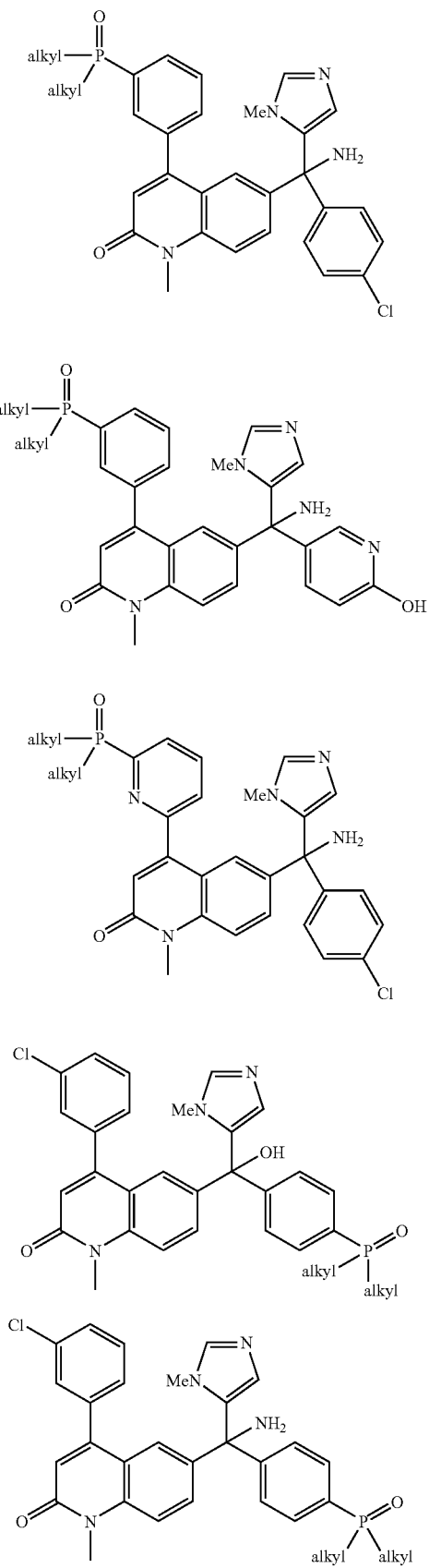
-continued
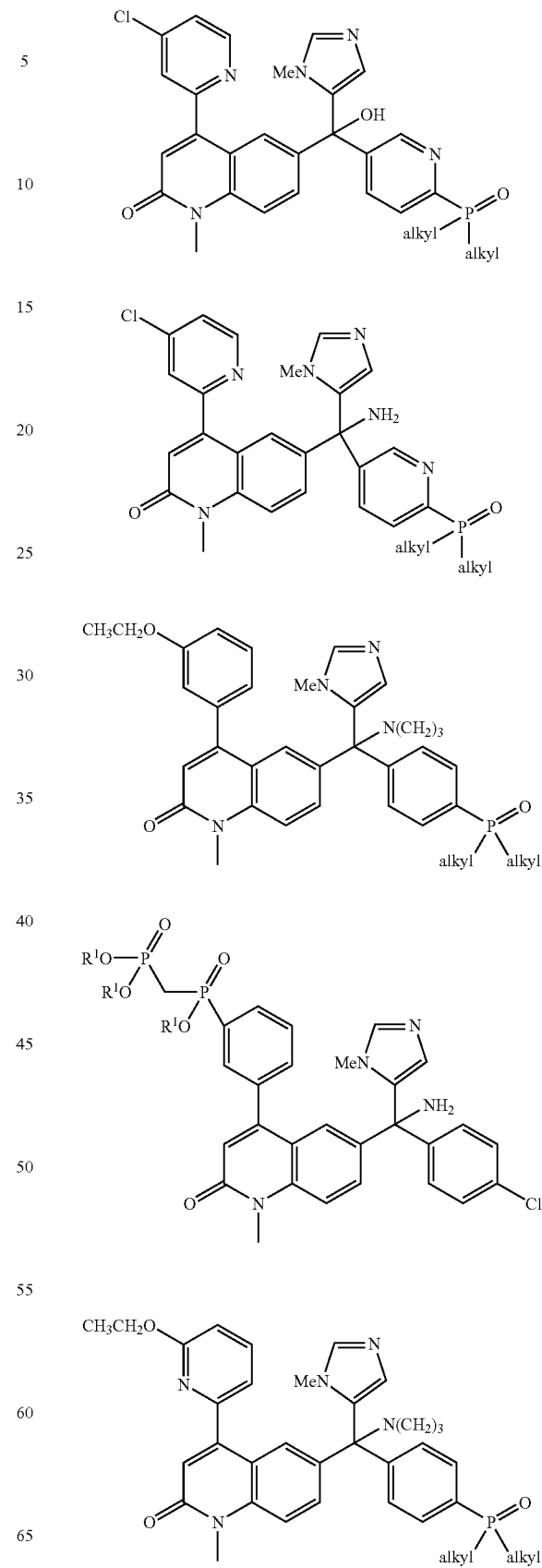

-continued
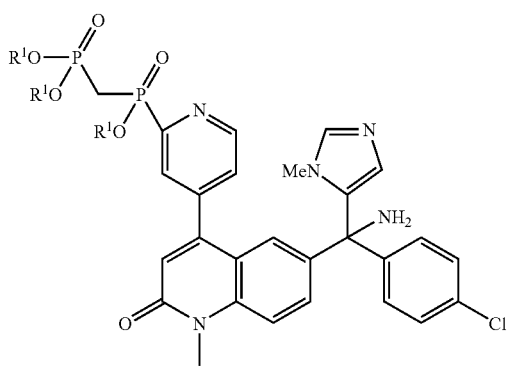
each occurrence of $R^1$ is independently a substituted or unsubstituted aliphatic, heteroaliphatic, aryl or heteroaryl moiety, or, except in $YR^1$ moieties in which Y is a covalent bond, $R^1$ may also be H; and
each alkyl and aryl group may be substituted or unsubstituted.
2. A compound chosen from the following:
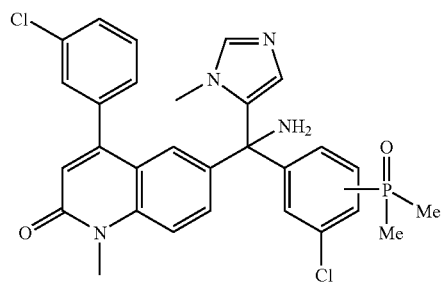
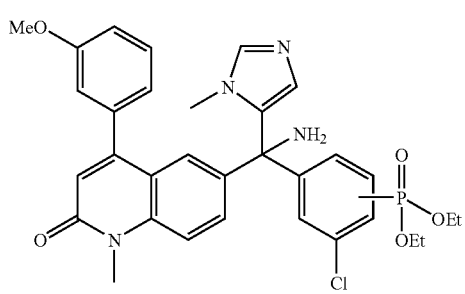
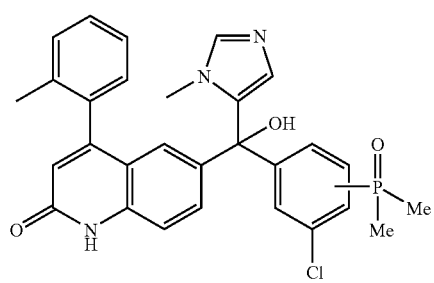
-continued
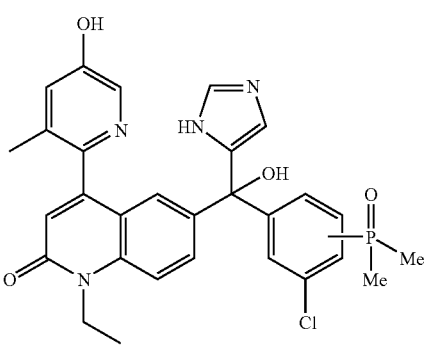
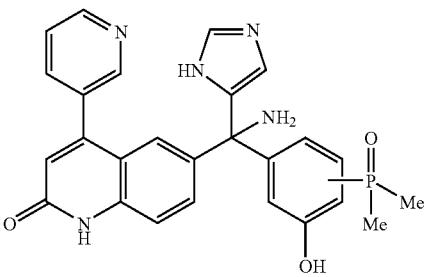
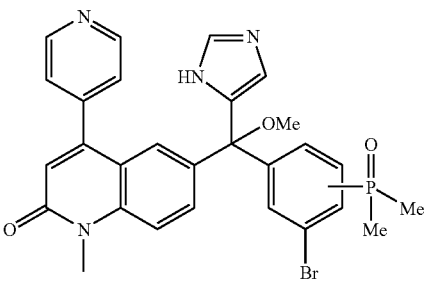
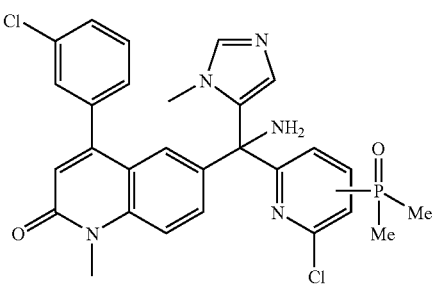
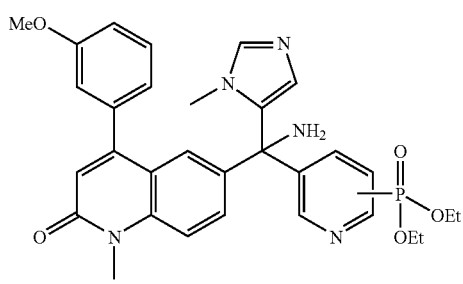

-continued
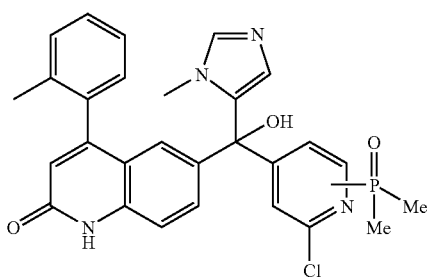
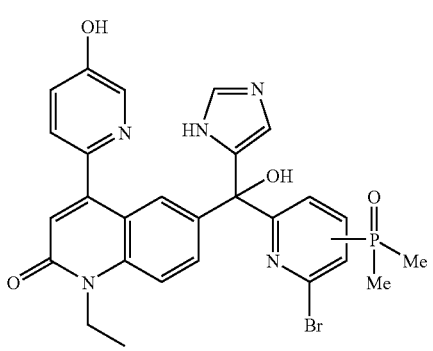
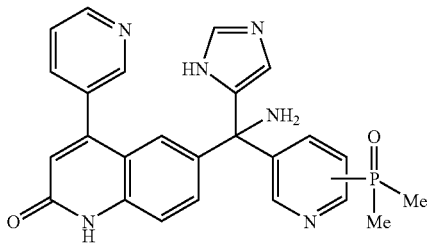
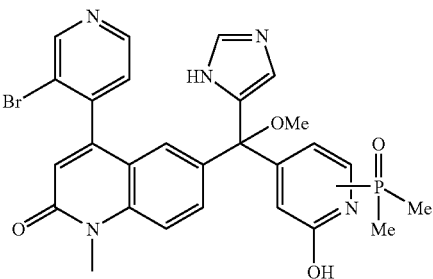
3. A compound chosen from:
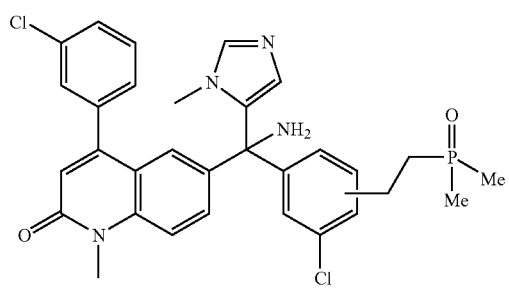
-continued
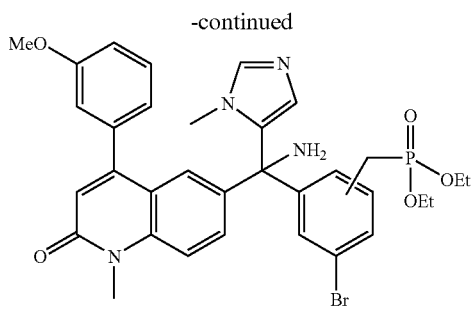
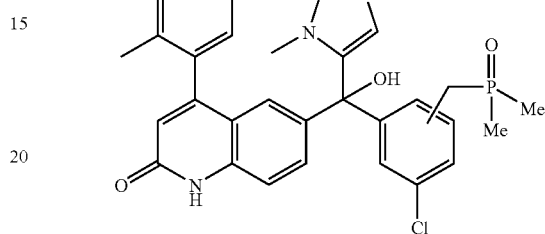
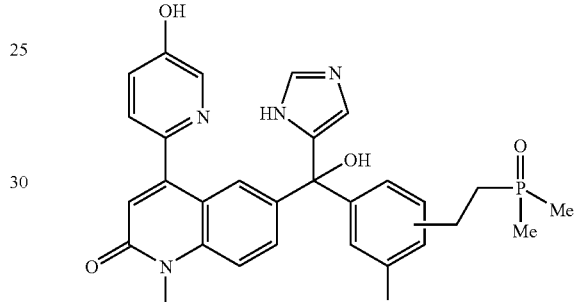
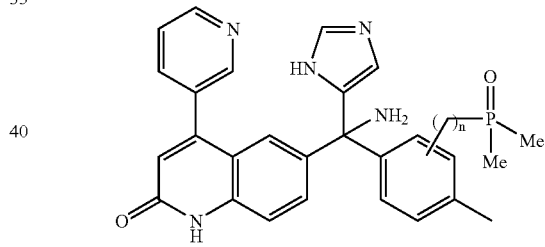
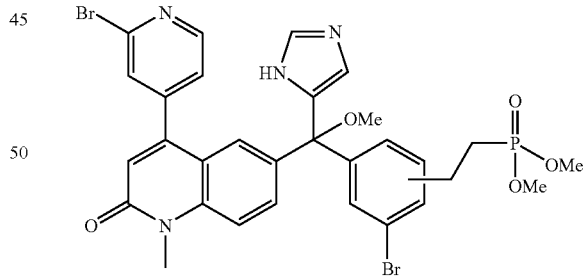
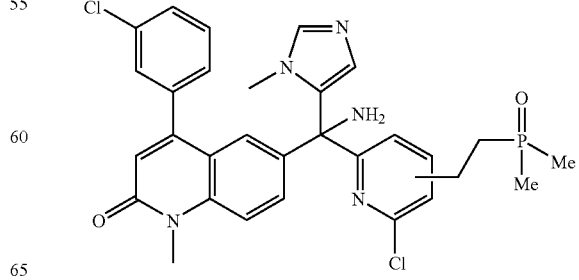

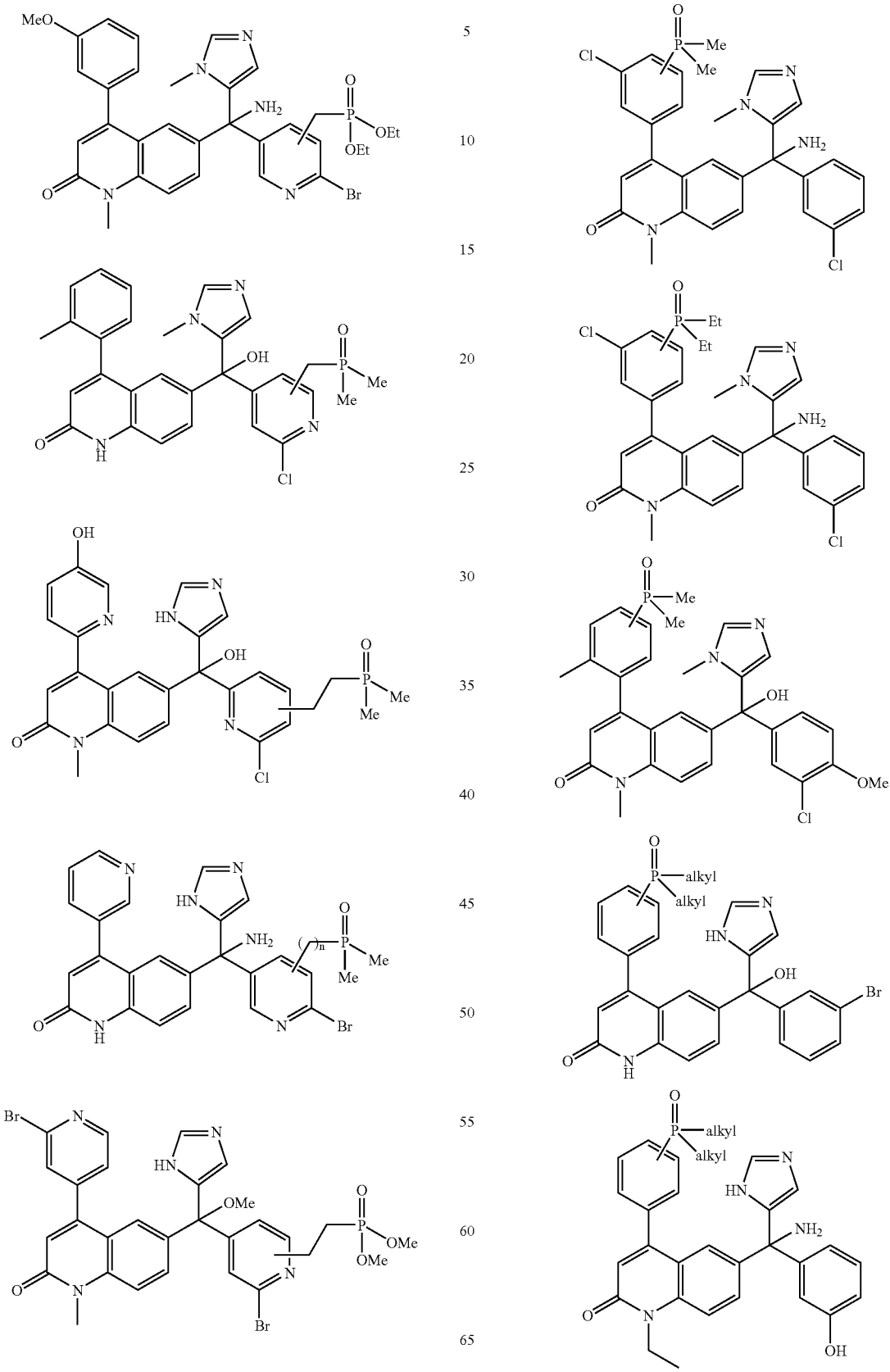
wherein n is an integer from 0 to 6.
4. A compound chosen from the following:

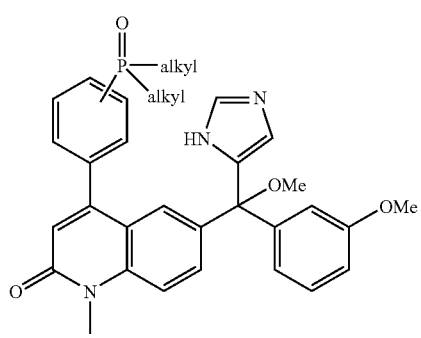
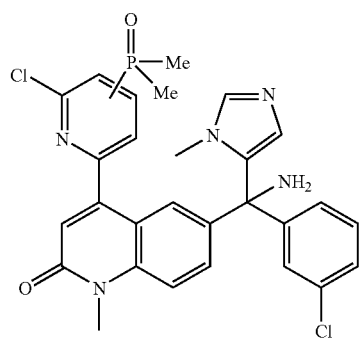
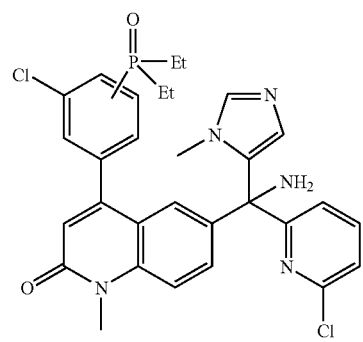
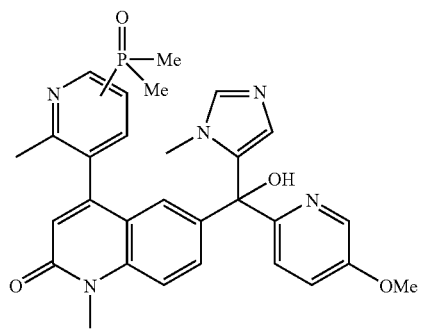
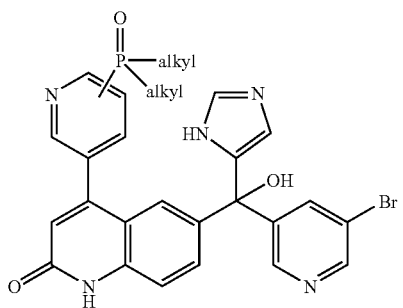
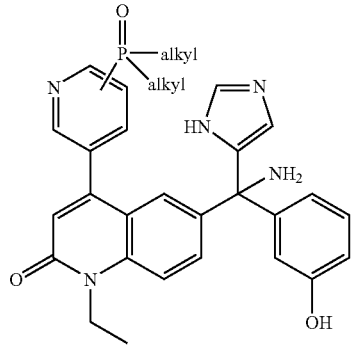
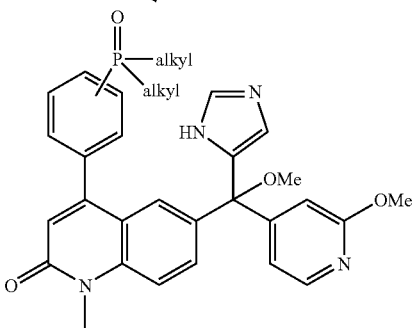
wherein each alkyl group may be substituted or unsubstituted.
5. A compound chosen from the following:
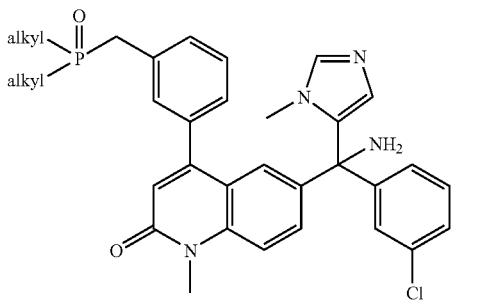
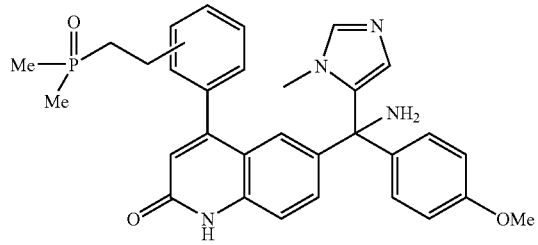
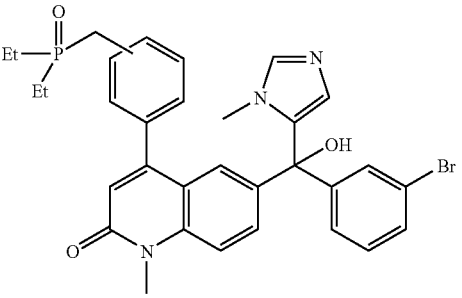

-continued

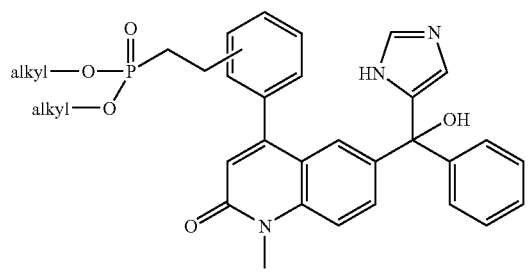
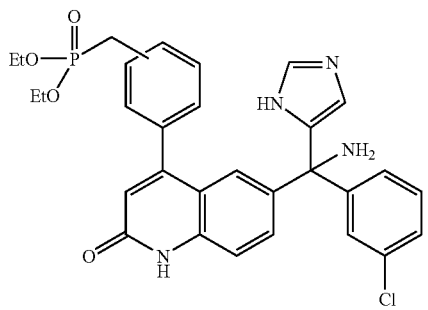
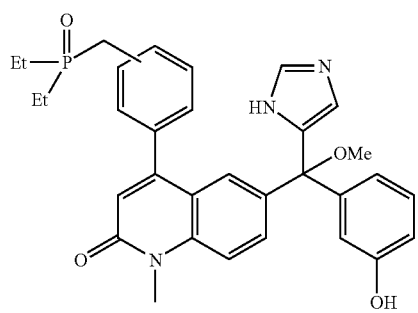
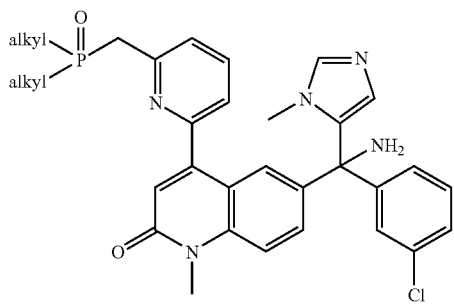
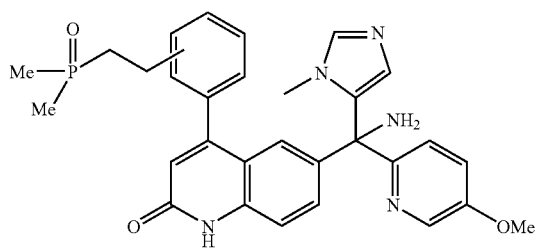

-continued

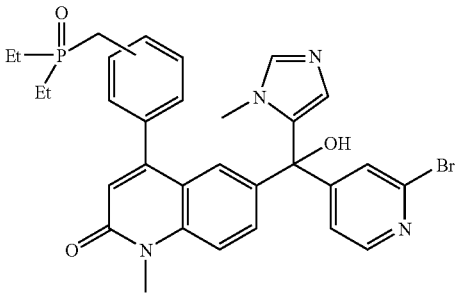
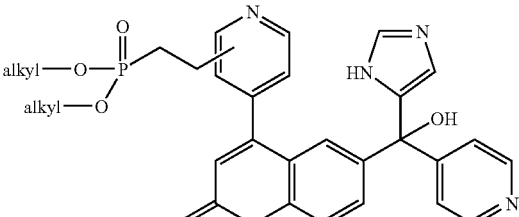
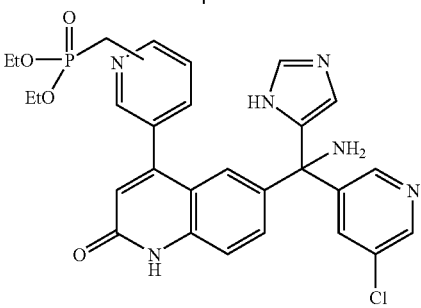
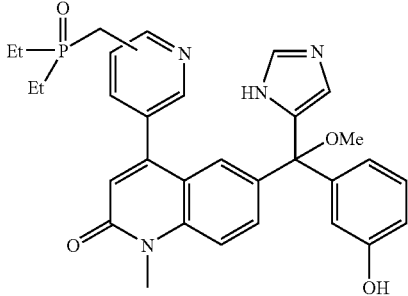

wherein each alkyl group may be substituted or unsubstituted.

6. The compound of any of claims 1–5 in which each alkyl group is a substituted or unsubstituted methyl, ethyl, n-propyl, isopropyl, cyclopropyl, —CH$_2$-cyclopropyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, or —CH$_2$-cyclohexyl moiety; or a benzyl or phenethyl moiety or a heteroaromatic or substituted derivative thereof.

* * * * *